United States Patent
Reich et al.

(10) Patent No.: US 10,420,314 B2
(45) Date of Patent: Sep. 24, 2019

(54) LOW LIGNIN NON-TRANSGENIC ALFALFA VARIETIES AND METHODS FOR PRODUCING THE SAME

(71) Applicant: Alforex Seeds LLC, Indianapolis, IN (US)

(72) Inventors: Jonathan M. Reich, Woodland, CA (US); David W. Johnson, La Crosse, WI (US); Mark E. Darling, Lansing, IA (US); Tracy A. Engh, Westby, WI (US)

(73) Assignee: ALFOREX SEEDS LLC, Indianapolis, IN (US)

( * ) Notice: Subject to any disclaimer, the term of this patent is extended or adjusted under 35 U.S.C. 154(b) by 0 days.

(21) Appl. No.: 16/177,528

(22) Filed: Nov. 1, 2018

(65) Prior Publication Data

US 2019/0069502 A1 Mar. 7, 2019

Related U.S. Application Data

(62) Division of application No. 15/915,985, filed on Mar. 8, 2018, which is a division of application No. 15/483,358, filed on Apr. 10, 2017, now Pat. No. 9,949,452, which is a division of application No. 14/869,567, filed on Sep. 29, 2015, now Pat. No. 9,648,826.

(60) Provisional application No. 62/057,022, filed on Sep. 29, 2014.

(51) Int. Cl.
*A01H 6/54* (2018.01)
*A01H 5/10* (2018.01)

(52) U.S. Cl.
CPC .............. *A01H 6/544* (2018.05); *A01H 5/10* (2013.01); *A01H 6/54* (2018.05)

(58) Field of Classification Search
None
See application file for complete search history.

(56) References Cited

U.S. PATENT DOCUMENTS

| | | |
|---|---|---|
| 4,535,060 A | 8/1985 | Comai |
| 4,769,061 A | 9/1988 | Comai |
| 4,940,835 A | 7/1990 | Shah et al. |
| 4,971,908 A | 11/1990 | Kishore et al. |
| 4,975,374 A | 12/1990 | Goodman et al. |
| 5,145,783 A | 9/1992 | Kishore et al. |
| 5,188,642 A | 2/1993 | Shah et al. |
| 5,188,960 A | 2/1993 | Payne et al. |
| 5,310,667 A | 5/1994 | Eichholtz et al. |
| 5,312,910 A | 5/1994 | Kishore et al. |
| 5,463,175 A | 10/1995 | Barry et al. |
| 5,489,520 A | 2/1996 | Adams et al. |
| 5,491,288 A | 2/1996 | Chaubet et al. |
| 5,510,471 A | 4/1996 | Lebrun et al. |
| 5,550,318 A | 8/1996 | Adams et al. |
| 5,559,223 A | 9/1996 | Falco et al. |
| 5,561,236 A | 10/1996 | Leemans et al. |
| 5,633,435 A | 5/1997 | Barry et al. |
| 5,633,436 A | 5/1997 | Wandelt |
| 5,633,448 A | 5/1997 | Lebrun et al. |
| 5,646,024 A | 7/1997 | Leemans et al. |
| 5,648,477 A | 7/1997 | Leemans et al. |
| 5,689,052 A | 11/1997 | Brown et al. |
| 5,776,760 A | 7/1998 | Barry et al. |
| 5,804,425 A | 9/1998 | Barry et al. |
| 5,850,016 A | 12/1998 | Jung et al. |
| 5,866,775 A | 2/1999 | Eichholtz et al. |
| 5,874,265 A | 2/1999 | Adams et al. |
| 5,879,903 A | 3/1999 | Strauch et al. |
| 5,880,275 A | 3/1999 | Fischhoff et al. |
| 5,885,801 A | 3/1999 | Rao |
| 5,885,802 A | 3/1999 | Rao |
| 5,912,414 A | 6/1999 | Falco et al. |
| 5,919,675 A | 7/1999 | Adams et al. |
| 5,939,599 A | 8/1999 | Chui et al. |
| 5,962,213 A | 10/1999 | Adams et al. |
| 5,990,389 A | 11/1999 | Rao et al. |
| RE36,449 E | 12/1999 | Lebrun et al. |
| 6,040,497 A | 3/2000 | Spencer et al. |
| 6,063,947 A | 5/2000 | DeBonte et al. |
| 6,127,600 A | 10/2000 | Beach et al. |
| 6,130,366 A | 10/2000 | Herrera-Estrella et al. |
| 6,177,616 B1 | 1/2001 | Bartsch et al. |
| 6,194,638 B1 | 2/2001 | Dhugga et al. |
| 6,197,561 B1 | 3/2001 | Martino-Catt et al. |
| 6,225,114 B1 | 5/2001 | Eichholtz et al. |
| 6,232,529 B1 | 5/2001 | Singletary et al. |
| 6,248,876 B1 | 6/2001 | Barry et al. |
| RE37,287 E | 7/2001 | Lebrun et al. |
| 6,291,224 B1 | 9/2001 | Martino-Catt et al. |
| 6,323,392 B1 | 11/2001 | Charne |

(Continued)

FOREIGN PATENT DOCUMENTS

| | | |
|---|---|---|
| CN | 1209958 | 3/1999 |
| WO | 2014/004683 | 1/2014 |

OTHER PUBLICATIONS

AOSCA application for variety CW 099079, dated Nov. 29, 2016.
(Continued)

*Primary Examiner* — Vinod Kumar

(57) ABSTRACT

Disclosed are alfalfa varieties with low or reduced lignin content, including an alfalfa seed designated CW 096043 deposited as ATCC Accession Number PTA-122473, an alfalfa seed designated CW 103009 deposited as ATCC Accession Number PTA-122475, an alfalfa seed designated CW 099079 deposited as ATCC Accession Number PTA-122474, an alfalfa seed designated CW 090075 deposited as ATCC Accession Number PTA-122471, an alfalfa seed designated CW 054004 deposited as ATCC Accession Number PTA-122470, an alfalfa seed designated CW 093009 deposited as ATCC Accession Number PTA-122472, and an alfalfa seed designated CW 104015 deposited as ATCC Accession Number PTA-122476. Also disclosed are plants, or parts thereof, grown from the seed of the cultivar, plants having the morphological and physiological characteristics of these alfalfa varieties, such as CW 096043, CW 103009, CW 099079, CW 090075, CW 054004, CW 093009, or CW 104015 and methods of using the plant or parts thereof in alfalfa breeding and alfalfa transformation.

20 Claims, 7 Drawing Sheets

(56) References Cited

U.S. PATENT DOCUMENTS

| | | |
|---|---|---|
| 6,338,961 B1 | 1/2002 | DeRose et al. |
| 6,346,403 B1 | 2/2002 | Rafalski et al. |
| 6,372,965 B1 | 4/2002 | Lightner et al. |
| 6,391,348 B1 | 5/2002 | Stillborn et al. |
| 6,399,859 B1 | 6/2002 | Nichols et al. |
| 6,423,886 B1 | 7/2002 | Singletary et al. |
| 6,441,274 B1 | 8/2002 | Cahoon et al. |
| 6,459,019 B1 | 10/2002 | Falco et al. |
| 6,531,648 B1 | 3/2003 | Lanahan et al. |
| 6,566,587 B1 | 5/2003 | Lebrun et al. |
| 6,652,195 B2 | 11/2003 | Vickars et al. |
| 6,664,445 B1 | 12/2003 | Falco et al. |
| 6,787,683 B1 | 9/2004 | Penna et al. |
| 6,803,498 B2 | 10/2004 | Dhugga et al. |
| 6,825,397 B1 | 11/2004 | Lowe et al. |
| 7,288,697 B2 | 10/2007 | Johnson et al. |
| 7,939,721 B2 | 5/2011 | Arnevik et al. |
| 8,685,677 B2 | 4/2014 | Novak et al. |
| 8,748,700 B2 | 6/2014 | Hanger et al. |
| 8,785,728 B2 | 7/2014 | Cui et al. |
| 2003/0009011 A1 | 1/2003 | Shi et al. |
| 2003/0079247 A1 | 4/2003 | Shi et al. |
| 2003/0150014 A1 | 8/2003 | Dhugga et al. |
| 2003/0163838 A1 | 8/2003 | Dhugga et al. |
| 2003/0204870 A1 | 10/2003 | Allen et al. |
| 2004/0025203 A1 | 2/2004 | Singletary et al. |
| 2004/0034886 A1 | 2/2004 | Cahoon et al. |
| 2004/0068767 A1 | 4/2004 | Dhugga et al. |
| 2006/0206969 A1* | 9/2006 | Johnson ............ A01H 5/10 800/295 |
| 2009/0044294 A1 | 2/2009 | Dixon et al. |

OTHER PUBLICATIONS

Reddy et al. "Targeted down-regulation of cytochrome P450 enzymes for forage quality improvement in alfalfa (*Medicago sativa* L.)," PNAS, vol. 102, No. 46, Nov. 15, 2005, pp. 16573-16578.
Jung et al., "Modifying crops to increase cell wall digestibility," Plant science 185-186 (2012) pp. 65-77.
ATCC Accession No. PTA-122473, date of receipt Aug. 14, 2015.
ATCC Accession No. PTA-122475, date of receipt Aug. 14, 2015.
ATCC Accession No. PTA-122474, date of receipt Aug. 14, 2015.
ATCC Accession No. PTA-122471, date of receipt Aug. 14, 2015.
ATCC Accession No. PTA-122470, date of receipt Aug. 14, 2015.
ATCC Accession No. PTA-122472, date of receipt Aug. 14, 2015.
ATCC Accession No. PTA-122476, date of receipt Aug. 14, 2015.
International Search Report and Written Opinion for Application No. PCT/US2015/052988 dated Jan. 5, 2016 (13 pages).

* cited by examiner

LOW LIGNIN NON-TRANSGENIC ALFALFA VARIETIES AND METHODS FOR PRODUCING THE SAME

CROSS-REFERENCE TO RELATED APPLICATIONS

This application is a divisional of U.S. patent application Ser. No. 15/915,985, which is a divisional of U.S. patent application Ser. No. 15/483,358, filed on Apr. 10, 2017, now U.S. Pat. No. 9,949,452, which is a divisional of U.S. patent application Ser. No. 14/869,567, now U.S. Pat. No. 9,648,826, which claims the benefit of U.S. Provisional Application No. 62/057,022, filed Sep. 29, 2014, the disclosures of each of which are incorporated herein by reference in their entireties.

TECHNICAL FIELD

This present disclosure relates to the field of alfalfa (*Medicago sativa*) breeding, specifically relating to alfalfa varieties with low or reduced lignin content.

BACKGROUND

Alfalfa (*Medicago sativa*) has often been referred to as the "Queen of Forages" because it is an excellent source of protein and digestible fiber, and because of its wide adaptation. Alfalfa has a high mineral content and contains at least 10 different vitamins and is an important source of vitamin A. It is grown for hay, pasture and silage, and is valued highly as a livestock feed. Increasing alfalfa fiber digestibility by decreasing lignin content is known to improve forage quality, ration formulation flexibility, and enhance feed value. Doing so while not adversely affecting yield and without having to introduce transgenes to develop stable, high yielding cultivars with low or reduced lignin content has long been a goal of alfalfa breeders.

SUMMARY

The present invention is directed to an alfalfa variety that has at least about 5.0% less lignin content as a percent of dry matter, compared to a control alfalfa variety grown under the same field growing conditions. The alfalfa variety may have at least about 5.0% to at least about 25.0% less total lignin content. The alfalfa variety may have about 5.0% to about 25% less acid detergent lignin content. The alfalfa variety may have at least about 6.0% to at least about 10.0% less acid detergent lignin content. The lignin content may be measured about 21 days after clipping, about 22 days after clipping, about 28 days after clipping, about 29 days after clipping, about 35 days after clipping, or about 42 days after clipping. The lignin content may be measured in the lower stems or in the whole plant of the alfalfa plant. The alfalfa variety may have at least about 5.0% to about 25.0% more total digestible nutrient, 5.0% to about 25.0% more relative forage quality, 5.0% to about 25.0% more relative forage value, or 5.0% to about 25.0% more milk per ton of dry mass compared to the commercial alfalfa variety grown under the same field growing conditions. The total digestible nutrient may be measured as in vitro total dry matter digestibility, neutral detergent fiber digestibility, or total tract neutral detergent fiber digestibility. The total digestibility nutrient may be measured about 21 days after clipping, about 22 days after clipping, about 28 days after clipping, about 29 days after clipping, about 35 days after clipping, or about 42 days after clipping. The control alfalfa variety may be a commercial alfalfa variety. The commercial alfalfa variety may be selected from the group consisting of 55V12, 56S82, Althea, Cisco II, Cornerstone, CW 1010, Del Rio, Fertilac 10, HybriForce 2600, HybriForce 700, HybriForce-2400, HybriForce-3400, Keystone II, Magnum 7, Magnum 7-Wet, Mecca III, N-R-Gee, P58N57, PGI 212, VR TOTAL, PGI 529 (DOMINATOR), PGI 557 (LELIA), PGI 608, PGI 709, PGI 801, PGI 909, PILLAR ST, ROBUST, Sedona, Star-Gold, SW7410, WL 319 HQ, and WL 440HQ. The alfalfa variety may comprise about 50% germplasm from (i) alfalfa variety CW 10-017 and about 50% germplasm from alfalfa variety CW10-018 or (ii) about 12.5% germplasm from alfalfa variety PCI 608, 12.5% germplasm from alfalfa variety CW 26071, 12.5% germplasm from alfalfa variety CW 056080, 37.5% germplasm from alfalfa variety CW 066081, 12.5% germplasm from alfalfa variety 06-7-514, 12.5% germplasm from alfalfa variety 06-7-525.

The present invention is directed to a seed of said alfalfa variety or regenerable parts of said seed.

The present invention is directed to a plant, or a part thereof, produced by growing said seed.

The present invention is directed to a pollen from said plant.

The present invention is directed to an ovule from said plant.

The present invention is directed to an alfalfa plant having all the physiological and morphological characteristics of said plant.

The present invention is directed to a tissue culture of regenerable cells from said plant, or the part thereof. The regenerable cells may be selected from the group consisting of protoplasts and calli, and wherein the regenerable cells are from a leaf, pollen, ovule, cotyledon, hypocotyl, embryo, root, pod, flower, shoot or stalk.

The present invention is directed to a protoplast produced from said tissue culture. The culture may be a callus culture.

The present invention is directed to an alfalfa plant regenerated from said tissue culture, wherein the alfalfa plant has all of the physiological and morphological characteristics of a plant produced by growing a seed designated CW096043 and deposited under ATCC Accession No. PTA-122473 or a plant produced by growing a seed designated CW103009 and deposited under ATCC Accession No. PTA-122475.

The present invention is directed to a tissue culture of regenerable cells from said plant, or the part thereof. The regenerable cells may be selected from the group consisting of protoplasts and calli, and wherein the regenerable cells are from a leaf, pollen, ovule, cotyledon, hypocotyl, embryo, root, pod, flower, shoot or stalk.

The present invention is directed to a protoplast produced from said tissue culture. The culture may be a callus culture.

The present invention is directed to an alfalfa plant regenerated from said tissue culture, wherein the plant has all of the physiological and morphological characteristics of a plant produced by growing a seed designated CW096043 and deposited under ATCC Accession No. PTA-122473 or a plant produced by growing a seed designated CW103009 and deposited under ATCC Accession No. PTA-122475.

The present invention is directed to a method for producing an alfalfa cultivar CW096043-derived alfalfa plant. The method comprises: (a) crossing CW096043 plants grown from CW096043 seed, representative seed of which has been deposited under ATCC Accession No: PTA-122473, with a second alfalfa plant to yield progeny alfalfa seed; and (b) growing the progeny seed to yield an alfalfa cultivar CW096043-derived alfalfa plant. The method may further comprise: (c) crossing the alfalfa cultivar CW096043-derived alfalfa plant of (b) with itself or a third alfalfa plant to yield a second alfalfa CW096043-derived alfalfa progeny seed; and (d) growing the second alfalfa progeny seed of (c) to yield a second alfalfa cultivar CW096043-derived alfalfa plant. Steps (c) and (d) may be repeated at least one time to generate an additional alfalfa cultivar CW096043-derived alfalfa plant.

The present invention is directed to a method for producing an alfalfa cultivar CW103009-derived alfalfa plant. The method comprises: (a) crossing CW103009 plants grown from CW103009 seed, representative seed of which has been deposited under ATCC Accession No: PTA-122475, with a second alfalfa plant to yield progeny alfalfa seed; and (b) growing the progeny seed to yield an alfalfa cultivar CW103009-derived alfalfa plant. The method may further comprise: (c) crossing the alfalfa cultivar CW103009-derived alfalfa plant of (b) with itself or a third alfalfa plant to yield a second alfalfa CW103009-derived alfalfa progeny seed; and (d) growing the second alfalfa progeny seed of (c) to yield a second alfalfa cultivar CW103009-derived alfalfa a plant. Steps (c) and (d) may be repeated at least one time to generate an additional alfalfa cultivar CW103009-derived alfalfa plant.

The present invention is directed to a method of introducing a desired trait into alfalfa CW096043 or CW103009. The method comprises: (a) crossing CW096043 or CW103009 plants grown from CW096043 seed, representative seed of which has been deposited under ATCC Accession No: PTA-122473, or CW103009 seed, representative seed of which has been deposited under ATCC Accession No: PTA-122475, with plants of a second alfalfa variety that comprise a desired trait to produce F1 progeny plants, wherein the desired trait is selected from the group consisting of male sterility, site-specific recombination, increased transformability, abiotic stress tolerance, herbicide resistance, insect resistance, disease resistance, altered phosphorus, altered antioxidants, altered fatty acids, altered essential amino acids and altered carbohydrates; (b) selecting F1 progeny plants that have the desired trait to produce selected F1 progeny plants; (c) crossing the selected progeny plants with the CW096043 or CW103009 plants to produce backcross progeny plants; (d) selecting for backcross progeny plants that have the desired trait and physiological and morphological characteristics of alfalfa variety CW096043 or CW103009 to produce selected backcross progeny plants; and (e) repeating steps (c) and (d) three or more times in succession to produce selected fourth or higher backcross progeny plants that comprise the desired trait and all the physiological and morphological characteristics of alfalfa variety CW096043 or CW103009.

The present invention is directed to a plant produced by said method. The plant may have the desired trait and all of the physiological and all morphological characteristics of alfalfa variety CW096043 or CW103009.

The present invention is directed to a method for producing an alfalfa plant having an altered agronomic trait. The method comprises introducing a polynucleotide into a CW096043 plant grown from CW096043 seed, representative seed of which has been deposited under ATCC Accession No: PTA-122473, or CW103009 plant grown from CW103009 seed, representative seed of which has been deposited under ATCC Accession No: PTA-122475, wherein the polynucleotide confers an altered agronomic trait to the plant selected from the group consisting of insect resistance, disease resistance, herbicide resistance, abiotic stress resistance, fatty acid metabolism, starch metabolism, carbohydrate metabolism, amino acid metabolism, phosphorus metabolism, antioxidant metabolism, male sterility, site specific DNA integration, plant growth, forage yield and flowering, and wherein the polynucleotide is expressed in the plant.

The present invention is directed to an alfalfa plant produced by said method.

The present invention is directed to a composition comprising a mixture of alfalfa seed. The mixture of alfalfa seed comprises between about 75% to about 95% of CW096043 seed, representative seed of CW096043 has been deposited under ATCC Accession No: PTA-122473, or between about 75% to about 95% of CW103009 seed, representative seed of CW103009 has been deposited under ATCC Accession No: PTA-122475.

The present invention is directed to a *Medicago sativa* seed designated as CW096043. A sample of said seed has been deposited as ATCC Accession Number PTA-122473.

The present invention is directed to a *Medicago sativa* seed designated as CW103009. A sample of said seed has been deposited as ATCC Accession Number PTA-122475.

The present invention is directed to a plant, or a part thereof, produced by growing said seed.

The present invention is directed to a pollen from said plant.

The present invention is directed to an ovule from said plant.

The present invention is directed to an alfalfa plant having all the physiological and morphological characteristics of said plant.

The present invention is directed to a tissue culture of regenerable cells from said plant, or the part thereof. The regenerable cells may be selected from the group consisting of protoplasts and calli, and wherein the regenerable cells are from a leaf, pollen, ovule, cotyledon, hypocotyl, embryo, root, pod, flower, shoot or stalk.

The present invention is directed to a protoplast produced from said tissue culture. The culture may be a callus culture.

The present invention is directed to an alfalfa plant regenerated from said tissue culture, wherein the alfalfa plant has all of the physiological and morphological characteristics of a plant produced by growing a seed designated CW096043 and deposited under ATCC Accession No. PTA-122473 or a plant produced by growing a seed designated CW103009 and deposited under ATCC Accession No. PTA-122475.

The present invention is directed to a tissue culture of regenerable cells from said plant, or the part thereof. The regenerable cells may be selected from the group consisting of protoplasts and calli, and wherein the regenerable cells are from a leaf, pollen, ovule, cotyledon, hypocotyl, embryo, root, pod, flower, shoot or stalk.

The present invention is directed to a protoplast produced from said tissue culture. The culture may be a callus culture.

The present invention is directed to an alfalfa plant regenerated from said tissue culture, wherein the plant has all of the physiological and morphological characteristics of a plant produced by growing a seed designated CW096043 and deposited under ATCC Accession No. PTA-122473 or a plant produced by growing a seed designated CW103009 and deposited under ATCC Accession No. PTA-122475.

The present invention is directed to a *Medicago sativa* seed designated as CW096043, wherein a sample of said seed has been deposited as ATCC Accession Number PTA-122473.

The present invention is directed to a *Medicago sativa* seed designated as CW103009, wherein a sample of said seed has been deposited as ATCC Accession Number PTA-122475.

The present invention is directed to a *Medicago sativa* seed designated as CW099079, wherein a sample of said seed has been deposited as ATCC Accession Number PTA-122474.

The present invention is directed to a *Medicago sativa* seed designated as CW090075, wherein a sample of said seed has been deposited as ATCC Accession Number PTA-122471.

The present invention is directed to a *Medicago sativa* seed designated as CW054004, wherein a sample of said seed has been deposited as ATCC Accession Number PTA-122470.

The present invention is directed to a *Medicago sativa* seed designated as CW093009, wherein a sample of said seed has been deposited as ATCC Accession Number PTA-122472.

The present invention is directed to a *Medicago sativa* seed designated as CW104015, wherein a sample of said seed has been deposited as ATCC Accession Number PTA-122476.

The present invention is directed to a method for producing an alfalfa cultivar-derived alfalfa plant of the disclosed low-lignin alfalfa variety, the method comprising: (a) crossing a plant grown from the seed of the disclosed low-lignin alfalfa variety with a second alfalfa plant to yield progeny alfalfa seed; and (b) growing the progeny seed to yield an alfalfa-derived alfalfa plant of the low-lignin alfalfa variety.

The present invention is directed to a method of introducing a desired trait into the disclosed low-lignin alfalfa varieties, the method comprising:

(a) crossing plants grown from seed of the low-lignin alfalfa varieties with plants of a second alfalfa variety that comprise a desired trait to produce F1 progeny plants, wherein the desired trait is selected from the group consisting of male sterility, site-specific recombination, increased transformability, abiotic stress tolerance, herbicide resistance, insect resistance, disease resistance, altered phosphorus, altered antioxidants, altered fatty acids, altered essential amino acids and altered carbohydrates;

(b) selecting F1 progeny plants that have the desired trait to produce selected F1 progeny plants;

(c) crossing the selected progeny plants with the plants of the low-lignin alfalfa varieties to produce backcross progeny plants;

(d) selecting for backcross progeny plants that have the desired trait and physiological and morphological characteristics of the low-lignin alfalfa varieties to produce selected backcross progeny plants; and (e) repeating steps (c) and (d) three or more times in succession to produce selected fourth or higher backcross progeny plants that comprise the desired trait and all the physiological and morphological characteristics of the low-lignin alfalfa varieties.

The present invention is directed to a method for producing an alfalfa plant having an altered agronomic trait, the method comprising introducing a polynucleotide into a plant grown from seed of the low-lignin alfalfa variety, wherein the polynucleotide confers an altered agronomic trait to the plant selected from the group consisting of insect resistance, disease resistance, herbicide resistance, abiotic stress resistance, fatty acid metabolism, starch metabolism, carbohydrate metabolism, amino acid metabolism, phosphorus metabolism, antioxidant metabolism, male sterility, site specific DNA integration, plant growth, forage yield and flowering, and wherein the polynucleotide is expressed in the plant.

The present invention is directed to a composition comprising a mixture of alfalfa seed, the mixture of alfalfa seed comprises between about 75% to about 95% of CW096043 seed, representative seed of CW096043 has been deposited under ATCC Accession No: PTA-122473, between about 75% to about 95% of CW103009 seed, representative seed of CW103009 has been deposited under ATCC Accession No: PTA-122475, between about 75% to about 95% of CW099079 seed, representative seed of CW099079 has been deposited under ATCC Accession No: PTA-122474, between about 75% to about 95% of CW090075 seed, representative seed of CW090075 has been deposited under ATCC Accession No: PTA-122471, between about 75% to about 95% of CW054004 seed, representative seed of CW054004 has been deposited under ATCC Accession No: PTA-122470, between about 75% to about 95% of CW093009 seed, representative seed of CW093009 has been deposited under ATCC Accession No: PTA-122472, or between about 75% to about 95% of CW104015 seed, representative seed of CW104015 has been deposited under ATCC Accession No: PTA-122476.

DETAILED DESCRIPTION

Figure 1:
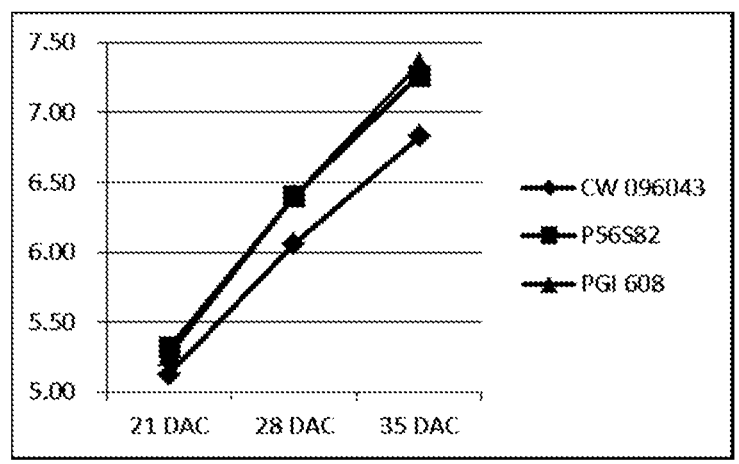
FIG. 1 shows the lignin content ("% ADL") after 21, 28, or 35 DAC of CW096043 compared to commercial varieties harvested in Year 3.

The present disclosure provides novel, high yielding alfalfa varieties, such as alfalfa varieties designated CW096043 and CW103009 that have low or reduced lignin content compared to commercial alfalfa varieties, and processes for making these novel alfalfa varieties. The novel, high yielding alfalfa varieties have low or reduced lignin content compared to commercial alfalfa varieties in the same fall dormancy group and/or a more dormant fall dormancy group. This disclosure relates to seed of these low-lignin alfalfa varieties, to the plants of these low-lignin alfalfa varieties, to plant parts these low-lignin alfalfa varieties, and to processes for making an alfalfa variety plant that comprise crossing these low-lignin alfalfa varieties with another alfalfa plant. This disclosure also relates to processes for making the claimed alfalfa variety containing in its genetic material one or more traits unrelated to low lignin introgressed into the low-lignin alfalfa varieties through backcross conversion and/or transformation, and to the alfalfa seed, plant and plant part produced by said introgression. This invention further relates to alfalfa seed, plant or plant part produced by crossing the low-lignin alfalfa varieties or an introgressed trait conversion of the low-lignin alfalfa varieties with another alfalfa population. This disclosure also relates to alfalfa populations derived from the low-lignin alfalfa varieties to processes for making other alfalfa populations derived from the low-lignin alfalfa varieties and to the alfalfa populations and their parts derived by the use of those processes.

This disclosure also relates to seed of alfalfa varieties CW096043 and CW103009, to the plants of alfalfa varieties CW096043 and CW103009, to plant parts of alfalfa varieties CW096043 and CW103009, and to processes for making an alfalfa variety plant that comprise crossing alfalfa varieties CW096043 or CW103009 with another alfalfa plant. This disclosure also relates to processes for making an alfalfa variety plant containing in its genetic material one or more traits introgressed into CW096043 or CW103009 through backcross conversion and/or transformation, and to the alfalfa seed, plant and plant part produced by said introgression. This invention further relates to alfalfa seed, plant or plant part produced by crossing the alfalfa varieties CW096043 or CW103009 or an introgressed trait conversion of CW096043 or CW103009 with another alfalfa population. This disclosure also relates to alfalfa populations derived from alfalfa varieties CW096043 or CW103009 to processes for making other alfalfa populations derived from varieties CW096043 or CW103009 and to the alfalfa populations and their parts derived by the use of those processes.

This disclosure also relates to seed of alfalfa varieties CW099079, CW090075, CW054004, CW093009, and CW104015, to the plants of alfalfa varieties CW099079, CW090075, CW054004, CW093009, and CW104015, to plant parts of alfalfa varieties CW099079, CW090075, CW054004, CW093009, and CW104015, and to processes for making an alfalfa variety plant that comprise crossing alfalfa varieties CW099079, CW090075, CW054004, CW093009, or CW104015 with another alfalfa plant. This disclosure also relates to processes for making an alfalfa variety plant containing in its genetic material one or more traits introgressed into CW099079, CW090075, CW054004, CW093009, or CW104015 through backcross conversion and/or transformation, and to the alfalfa seed, plant and plant part produced by said introgression. This invention further relates to alfalfa seed, plant or plant part produced by crossing the alfalfa varieties CW099079, CW090075, CW054004, CW093009, or CW104015 or an introgressed trait conversion of CW099079, CW090075, CW054004, CW093009, or CW104015 with another alfalfa population. This disclosure also relates to alfalfa populations derived from alfalfa varieties CW099079, CW090075, CW054004, CW093009, or CW104015 to processes for making other alfalfa populations derived from varieties CW099079, CW090075, CW054004, CW093009, or CW104015 and to the alfalfa populations and their parts derived by the use of those processes.

1. DEFINITIONS

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

Terms used in the descriptions and tables that follow are defined as follows:

Acid Detergent Fiber ("ADF"). Acid detergent fiber approximates the amount of cellulose fiber and ash present in a feed. Forages with high ADF values are less digestible than forages with low ADF values and, therefore, provide fewer nutrients to the animal through digestion. Because of this relationship, ADF serves as an estimate of digestibility and can be used by nutritionists to predict the energy that will be available from a forage.

Acid Detergent Lignin ("ADL"). Acid detergent lignin is the lignin in the residue determined following extraction with acid detergent. ADL is an estimate of lignin content. Lignin is an indigestible component of forage fiber (NDF) that is believed to limit the extent to which forage fiber can be digested by ruminant animals.

Crude Protein ("CP"). Crude Protein ("CP") is determined in part by measuring the total nitrogen concentration of a forage. This technique measures not only the nitrogen present in true proteins, but also that present in non-protein forms such as ammonia, urea and nitrate. Because most of the non-protein forms of nitrogen are converted to true protein by the rumen microorganisms, CP is considered by nutritionists to provide an accurate measure of the protein that will be available to ruminant animals from a given forage.

DM. DM is the abbreviation for Dietary Dry Matter and used to calculate yield.

Digestible Neutral Detergent Fiber ("dNDF"). Digestible Neutral Detergent Fiber is the digestible fraction expressed as % of DM.

Enhance feed value and Relative Feed Value ("RFV"). Enhance feed value refers to the forage quality, such as fiber content, digestibility, and available carbohydrate resources available to livestock. Enhanced feed value or alfalfa quality is determined by the Relative Feed Value (RFV) expressed as a percentage of alfalfa at 100% bloom and is used as a predictor of feed value in the field. Components that effect feed value are acid detergent lignin concentration and G lignin and neutral detergent fiber digestibility. The measurement of these feed value components is an aspect of the invention.

Dyn Kd. Dyn Kd refers to the rate of fiber digestion or the digestibility rate.

Fall dormancy (FD). Most alfalfa plants go dormant in the fall in preparation for winter. The onset of dormancy is triggered by a combination of day length and temperature and is genotype dependent. Fall dormancy scores measure the dormancy response of alfalfa genotypes by quantifying how early dormancy is triggered. The standard fall dormancy test requires that plants are cut off in early September with plant height measured in mid-October. Early fall dormant types show very little growth after the September clipping, later fall dormant type demonstrate substantial growth. Alfalfa is classified into fall dormancy groups or classes numbered 1 through 11, where fall dormancy group 1 is very early fall dormant suited for cold climates and fall dormancy group 11 is very non-dormant and suited for very hot climates in which the plant would grow throughout the winter months. FD 1 is considered Very Dormant, FD 2 and FD3 are considered Dormant, FD 4, FD 5 and FD 6 are considered Moderately Dormant, FD7 and FD 8 are considered Non-Dormant, and FD 9, FD 10 and FD 11 are considered Very-Non-Dormant.

Forage yield. Forage yield is measured by harvesting herbage for part of or the entire life of the stand.

In Vitro True Digestibility ("IVTD"). In Vitro True Digestibility is a measurement of digestibility utilizing actual rumen microorganisms.

In Vitro True Dry Matter Digestibility ("IVTDMD"). In Vitro True Dry Matter Digestibility measures the digestibility of the entire forage plant by incubating samples of the plant in rumen fluid taken from a cow, then boiling the incubated samples in neutral detergent to ensure that all non-fiber portions of the sample are removed. This procedure estimates how much of the total dry matter in a forage plant is actually digestible by the cow.

Milk Per Acre ("MA") and Milk Per Ton ("MT"). Milk Per Ton is an estimate of forage quality and milk production that could be supported by a given forage when fed as part of a total mixed ration. Milk per ton (lb/ton) is primarily driven by starch content, starch digestibility, and NDF digestibility. The equation for calculating milk per ton uses Neutral-Detergent Fiber ("NDF") and Acid-Detergent Fiber ("ADF") to calculate total energy intake possible from the forage. After subtracting the amount of energy required for daily maintenance of the cow, the quantity of milk that could be produced from the remaining energy is calculated. The ratio of milk produced to forage consumed is then reported in the units of pounds of milk produced per ton of forage consumed. Milk per ton is useful because it characterizes forage quality in two terms that a dairy farmer is familiar with: pounds of milk and tons of forage. "Milk Per Acre" is determined by combining milk per ton and dry matter yield per acre (lb/acre). Milk per acre is calculated by multiplying milk per ton times dry matter yield per acre. These terms are widely used to estimate the economic value of a forage.

Neutral-Detergent Fiber ("NDF"). Neutral-Detergent Fiber represents the total amount of fiber present in the alfalfa. "aNDF" refers to amylase-treated neutral detergent fiber.

"Neutral Detergent Fiber Digestibility" (NDFD). Neutral Detergent Fiber Digestibility (NDFD) refers to the content of forage is a measure of the digestibility of a forage fiber as % of NDF, and can be measured in vitro and predicted using Near Infrared Reflectance Spectroscopy (NIRS). NDFD is the digestible fraction expressed as % of NDF. The higher the NDFD value the more digestible the forage. NDFD represents the indigestible and slowly digestible components in plant cell wall (cellulose, hemicellulose, lignin (units=% of dry matter)). dNDF may be used to calculate NDFD.

Persistence. The ability of the cultivar to last over a minimum of two years. This measurement is documented in the visual percent stand remaining at the time of observation.

Relative Forage Quality ("RFQ"). Relative Forage Quality ("RFQ") is a numeric value that estimates the energy content of forage for total digestible nutrients as recommended by the National Research Council. Values are assigned to forages based upon the actual fiber digestibility (NDFD) and Total Digestible Nutrients (TDN). By combining these two relationships, an estimate of how the forage will perform in animal rations is predicted. Relative forage quality has been accepted in many areas as a means of estimating forage feeding value and is commonly used in determining the price of alfalfa at tested hay auctions or for on farm use.

Synthetic variety ("SYN"). SYN variety is developed by intercrossing a number of genotypes with specific favorable characteristics and/or overall general favorable qualities. SYN variety can be developed by using clones, inbreds, open pollinated varieties, and/or individual heterozygous plants.

TA. TA is the abbreviation for Tons per Acre and is used to calculate yield.

Total Digestible Nutrients. Total Digestible Nutrients ("TDN") is an estimate of the energy content of a feedstuff based on its relative proportions of fiber, fat, carbohydrate, crude protein, and ash. Because it is expensive to measure each of these components, TDN is usually estimated from ADF or IVTD. TDN may overestimate the energy content of low quality forages and thus may not accurately reflect the nutritional value of all forage samples.

Total Tract NDF Digestibility ("TTNDFD"). Total Tract NDF Digestibility ("TTNDFD") is a tool that combines feed (feed fiber—potentially digestible NDF rate of fiber digestion) and cow (fiber digestion—rate of passage) factors to measure energy from fiber. It is a calculation that uses several time points of NDFD, for example, after 24, 30, or 48 hours, combined with the rate of fiber digestion, the rate of fiber passage and also indigestible fiber, therefore giving a better picture of fiber digestibility as a whole. The calculation is calibrated to a cow producing 85 pounds of milk. A 2-3 unit change in ration TTNDFD corresponds to a one pound change in milk yield.

Weighted mean. Weighted mean is similar to an arithmetic mean where instead of each of the data points contributing equally to the final average, some data points contribute more than others.

2. ALFALFA VARIETIES WITH LOW OR REDUCED LIGNIN

The present disclosure relates to alfalfa varieties having low or reduced lignin content that does not result from introducing one or more transgenes. Lignin is an insoluble polymer which occurs in the secondary thickening of plant cell walls and is primarily responsible for the rigidity of plant stems. Although lignin is essential for vascular function in plants, and may be involved in disease resistance in cereals, there is much interest in producing plants with reduced lignin content.

The digestibility of forage grasses by cattle decreases with increasing lignin content. Lignin concentration is an important measurable factor limiting the in vitro digestibility of other constituents including cellulose, hemicellulose, and neutral detergent fiber. Small increases (approximately 1%) in lignin content can result in relatively large decreases (approximately 7%) in digestibility of plant dry matter. For example, an increase in one percentage unit NDFD results in a 0.37-pound increase in forage dry matter intake per day (lb/d), and a 0.55 lb/d increase in 4% fat corrected milk (FCM) yield. Cows fed forages with greater NDFD are able to obtain more total energy and nutritive value from the forages. As a result, the energy requirements can be fulfilled with less grain provided in the diet. Lower NDFD in forage legumes is most often related to the maturity of the forage plant, which is accompanied by an increase in lignin concentrations and associated with an increase in cellulose fibers.

Fall dormancy influences stand persistence, adaptation, and performance. Yield and quality are related to fall dormancy and maturity. Non-dormant varieties (FD 7-9) mature faster and typically yield more compared to dormant varieties, yet dormant varieties have more quality and lower lignin. Non-dormant alfalfa varieties (higher fall dormancy groups) typically have higher lignin content compared to more dormant alfalfa varieties (lower fall dormancy groups). The disclosed alfalfa varieties have low or reduced lignin content compared to control alfalfa varieties in the same fall dormancy group and/or control alfalfa varieties that are more dormant.

a) Acid Detergent Lignin (ADL)

The low-lignin alfalfa varieties may have reduced levels of acid detergent lignin (ADL) as compared to a control alfalfa variety grown under the same field conditions. The low-lignin alfalfa variety may have at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 20%, at least about 25%, at least about 30%, at least about 40%, at least about 50%, or from about 1% to about 50%, about 1% to about 40%, about 1% to about 30%, about 1% to about 25%, about 1% to about 20%, about 1% to about 15%, about 1% to about 10%, about 5% to about 50%, about 5% to about 40%, about 5% to about 30%, about 5% to about 25%, about 5% to about 20%, about 5% to about 15%, about 5% to about 10%, about 6% to about 50%, about 6% to about 40%, about 6% to about 30%, about 6% to about 25%, about 6% to about 20%, about 6% to about 15%, about 6% to about 10%, about 7% to about 50%, about 7% to about 40%, about 7% to about 30%, about 7% to about 25%, about 7% to about 20%, about 7% to about 15%, about 7% to about 10%, about 10% to about 50%; about 10% to about 40%, about 10% to about 30%, about 10% to about 25%, about 10% to about 20%, or about 10% to about 15% less ADL compared to a control alfalfa variety grown under the same field conditions.

The low-lignin alfalfa varieties may have reduced levels of acid detergent lignin (ADL) as compared to a control alfalfa variety in the same fall dormancy group or a control alfalfa variety that is more dormant and is grown under the same field conditions. The low-lignin alfalfa variety may have at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 20%, at least about 25%, at least about 30%, at least about 40%, at least about 50%, or from about 1% to about 50%, about 1% to about 40%, about 1% to about 30%, about 1% to about 25%, about 1% to about 20%, about 1% to about 15%, about 1% to about 10%, about 5% to about 50%, about 5% to about 40%, about 5% to about 30%, about 5% to about 25%, about 5% to about 20%, about 5% to about 15%, about 5% to about 10%, about 6% to about 50%, about 6% to about 40%, about 6% to about 30%, about 6% to about 25%, about 6% to about 20%, about 6% to about 15%, about 6% to about 10%, about 7% to about 50%, about 7% to about 40%, about 7% to about 30%, about 7% to about 25%, about 7% to about 20%, about 7% to about 15%, about 7% to about 10%, about 10% to about 50%; about 10% to about 40%, about 10% to about 30%, about 10% to about 25%, about 10% to about 20%, or about 10% to about 15% less ADL compared to a control alfalfa variety in the same fall dormancy group or a control alfalfa variety that is more dormant and is grown under the same field conditions.

I. Lower Stems

The "lower stem" of the alfalfa plant is described as the lower 12 inches of the alfalfa plant that has been harvested 1.75" above ground level with the leaves completely removed. The lower stem is the most lignified part of the alfalfa plant, and the least digestible. The low-lignin alfalfa varieties may have reduced levels of acid detergent lignin (ADL) in the lower stem as compared to the lower stem of a control alfalfa variety grown under the same field conditions. The low-lignin alfalfa variety may have at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 20%, at least about 25%, at least about 30%, at least about 40%, at least about 50%, or from about 1% to about 50%, about 1% to about 40%, about 1% to about 30%, about 1% to about 25%, about 1% to about 20%, about 1% to about 15%, about 1% to about 10%, about 5% to about 50%, about 5% to about 40%, about 5% to about 30%, about 5% to about 25%, about 5% to about 20%, about 5% to about 15%, about 5% to about 10%, about 6% to about 50%, about 6% to about 40%, about 6% to about 30%, about 6% to about 25%, about 6% to about 20%, about 6% to about 15%, about 6% to about 10%, about 7% to about 50%, about 7% to about 40%, about 7% to about 30%, about 7% to about 25%, about 7% to about 20%, about 7% to about 15%, about 7% to about 10%, about 10% to about 50%; about 10% to about 40%, about 10% to about 30%, about 10% to about 25%, about 10% to about 20%, or about 10% to about 15% less ADL in the lower stem compared to the lower stem of a control alfalfa variety grown under the same field conditions.

The low-lignin alfalfa varieties may have reduced levels of acid detergent lignin (ADL) in the lower stem as compared to the lower stem of a control alfalfa variety in the same fall dormancy group or a control alfalfa variety that is more dormant and is grown under the same field conditions. The low-lignin alfalfa variety may have at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 20%, at least about 25%, at least about 30%, at least about 40%, at least about 50%, or from about 1% to about 50%, about 1% to about 40%, about 1% to about 30%, about 1% to about 25%, about 1% to about 20%, about 1% to about 15%, about 1% to about 10%, about 5% to about 50%, about 5% to about 40%, about 5% to about 30%, about 5% to about 25%, about 5% to about 20%, about 5% to about 15%, about 5% to about 10%, about 6% to about 50%, about 6% to about 40%, about 6% to about 30%, about 6% to about 25%, about 6% to about 20%, about 6% to about 15%, about 6% to about 10%, about 7% to about 50%, about 7% to about 40%, about 7% to about 30%, about 7% to about 25%, about 7% to about 20%, about 7% to about 15%, about 7% to about 10%, about 10% to about 50%; about 10% to about 40%, about 10% to about 30%, about 10% to about 25%, about 10% to about 20%, or about 10% to about 15% less ADL in the lower stem compared to the lower stem of a control alfalfa variety in the same fall dormancy group or a control alfalfa variety that is more dormant and is grown under the same field conditions.

II. Whole Plant

The low-lignin alfalfa varieties may have reduced levels of acid detergent lignin (ADL) in the whole plant as compared to the whole plant of a control alfalfa variety grown under the same field conditions. The low-lignin alfalfa variety may have at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 20%, at least about 25%, at least about 30%, at least about 40%, at least about 50%, or from about 1% to about 50%, about 1% to about 40%, about 1% to about 30%, about 1% to about 25%, about 1% to about 20%, about 1% to about 15%, about 1% to about 10%, about 5% to about 50%, about 5% to about 40%, about 5% to about 30%, about 5% to about 25%, about 5% to about 20%, about 5% to about 15%, about 5% to about 10%, about 6% to about 50%, about 6% to about 40%, about 6% to about 30%, about 6% to about 25%, about 6% to about 20%, about 6% to about 15%, about 6% to about 10%, about 7% to about 50%, about 7% to about 40%, about 7% to about 30%, about 7% to about 25%, about 7% to about 20%, about 7% to about 15%, about 7% to about 10%, about 10% to about 50%; about 10% to about 40%, about 10% to about 30%, about 10% to about 25%, about 10% to about 20%, or about 10% to about 15% less ADL in the whole plant compared to the whole plant of a control alfalfa variety grown under the same field conditions.

The low-lignin alfalfa varieties may have reduced levels of acid detergent lignin (ADL) in the whole plant as compared to the whole plant of a control alfalfa variety in the same fall dormancy group or a control alfalfa variety that is more dormant and is grown under the same field conditions. The low-lignin alfalfa variety may have at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 20%, at least about 25%, at least about 30%, at least about 40%, at least about 50%, or from about 1% to about 50%, about 1% to about 40%, about 1% to about 30%, about 1% to about 25%, about 1% to about 20%, about 1% to about 15%, about 1% to about 10%, about 5% to about 50%, about 5% to about 40%, about 5% to about 30%, about 5% to about 25%, about 5% to about 20%, about 5% to about 15%, about 5% to about 10%, about 6% to about 50%, about 6% to about 40%, about 6% to about 30%, about 6% to about 25%, about 6% to about 20%, about 6% to about 15%, about 6% to about 10%, about 7% to about 50%, about 7% to about 40%, about 7% to about 30%, about 7% to about 25%, about 7% to about 20%, about 7% to about 15%, about 7% to about 10%, about 10% to about 50%; about 10% to about 40%, about 10% to about 30%, about 10% to about 25%, about 10% to about 20%, or about 10% to about 15% less ADL in the whole plant compared to the whole plant of a control alfalfa variety grown in the same fall dormancy group or a control alfalfa variety that is more dormant and is under the same field conditions.

b) Total Digestible Nutrients

The low-lignin alfalfa varieties may have increased levels of total digestible nutrients. The total digestible nutrients may be measured as Total Digestible Nutrients (TDN), In Vitro True Dry Matter Digestibility (IVTDMD), Neutral Detergent Fiber Digestibility (NDFD), Total Tract NDF Digestibility (TTNDFD), rate of digestibility (Dyn Kd), relative forage quality (RFQ), milk per ton of dry mass (mile/ton), and milk per acre (milk/acre). The low-lignin alfalfa varieties may have at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 20%, at least about 25%, at least about 30%, at least about 40%, at least about 50%, or from about 1% to about 50%, about 1% to about 40%, about 1% to about 30%, about 1% to about 25%, about 1% to about 20%, about 1% to about 15%, about 1% to about 10%, about 5% to about 50%, about 5% to about 40%, about 5% to about 30%, about 5% to about 25%, about 5% to about 20%, about 5% to about 15%, about 5% to about 10%, about 6% to about 50%, about 6% to about 40%, about 6% to about 30%, about 6% to about 25%, about 6% to about 20%, about 6% to about 15%, about 6% to about 10%, about 7% to about 50%, about 7% to about 40%, about 7% to about 30%, about 7% to about 25%, about 7% to about 20%, about 7% to about 15%, about 7% to about 10%, about 10% to about 50%; about 10% to about 40%, about 10% to about 30%, about 10% to about 25%, about 10% to about 20%, or about 10% to about 15% more total digestible nutrients compared to a control alfalfa variety grown under the same field conditions.

The low-lignin alfalfa varieties may have at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 20%, at least about 25%, at least about 30%, at least about 40%, at least about 50%, or from about 1% to about 50%, about 1% to about 40%, about 1% to about 30%, about 1% to about 25%, about 1% to about 20%, about 1% to about 15%, about 1% to about 10%, about 5% to about 50%, about 5% to about 40%, about 5% to about 30%, about 5% to about 25%, about 5% to about 20%, about 5% to about 15%, about 5% to about 10%, about 6% to about 50%, about 6% to about 40%, about 6% to about 30%, about 6% to about 25%, about 6% to about 20%, about 6% to about 15%, about 6% to about 10%, about 7% to about 50%, about 7% to about 40%, about 7% to about 30%, about 7% to about 25%, about 7% to about 20%, about 7% to about 15%, about 7% to about 10%, about 10% to about 50%; about 10% to about 40%, about 10% to about 30%, about 10% to about 25%, about 10% to about 20%, or about 10% to about 15% more total digestible nutrients compared to a control alfalfa variety in the same fall dormancy group or a control alfalfa variety that is more dormant and is grown under the same field conditions.

c) Leaf:Stem Ratio

The Leaf:stem ratio reflects plant and canopy architecture and is an indirect determinant of forage quality, including lignin content. The low-lignin alfalfa varieties may have an increased leaf:stem ratio compared to a control alfalfa variety grown under the same field conditions. The low-lignin alfalfa varieties may have an increased number of leaves in the lower canopy compared to a control alfalfa variety grown under the same field conditions.

The low-lignin alfalfa varieties may have at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 20%, at least about 25%, at least about 30%, at least about 40%, at least about 50%, or from about 1% to about 50%, about 1% to about 40%, about 1% to about 30%, about 1% to about 25%, about 1% to about 20%, about 1% to about 15%, about 1% to about 10%, about 5% to about 50%, about 5% to about 40%, about 5% to about 30%, about 5% to about 25%, about 5% to about 20%, about 5% to about 15%, about 5% to about 10%, about 6% to about 50%, about 6% to about 40%, about 6% to about 30%, about 6% to about 25%, about 6% to about 20%, about 6% to about 15%, about 6% to about 10%, about 7% to about 50%, about 7% to about 40%, about 7% to about 30%, about 7% to about 25%, about 7% to about 20%, about 7% to about 15%, about 7% to about 10%, about 10% to about 50%; about 10% to about 40%, about 10% to about 30%, about 10% to about 25%, about 10% to about 20%, or about 10% to about 15% more leaves compared to a control alfalfa variety grown under the same field conditions.

The low-lignin alfalfa varieties may have increased leaf to stem ratio compared to a control alfalfa variety in the same fall dormancy group or a control alfalfa variety that is more dormant and is grown under the same field conditions. The low-lignin alfalfa varieties may have at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 20%, at least about 25%, at least about 30%, at least about 40%, at least about 50%, or from about 1% to about 50%, about 1% to about 40%, about 1% to about 30%, about 1% to about 25%, about 1% to about 20%, about 1% to about 15%, about 1% to about 10%, about 5% to about 50%, about 5% to about 40%, about 5% to about 30%, about 5% to about 25%, about 5% to about 20%, about 5% to about 15%, about 5% to about 10%, about 6% to about 50%, about 6% to about 40%, about 6% to about 30%, about 6% to about 25%, about 6% to about 20%, about 6% to about 15%, about 6% to about 10%, about 7% to about 50%, about 7% to about 40%, about 7% to about 30%, about 7% to about 25%, about 7% to about 20%, about 7% to about 15%, about 7% to about 10%, about 10% to about 50%; about 10% to about 40%, about 10% to about 30%, about 10% to about 25%, about 10% to about 20%, or about 10% to about 15% more leaves compared to a control alfalfa variety in the same fall dormancy group or a control alfalfa variety that is more dormant and is grown under the same field conditions.

d) Plant Selection Characteristics

The low-lignin alfalfa varieties may have other plant characteristics that are related to the reduced levels of lignin and contribute to digestibility. The low-lignin alfalfa varieties may have an increased leaf contribution to biomass, a higher forage dry matter yield, a higher foliage, a higher output, allow for an increase number of cuttings per season, have increased winter hardiness, and/or may be resistant to one or more of the following pests: bacterial wilt, Fusarium Wilt, Verticillium wilt, Phytophthora root rot, Aphanomyces root rot, anthracnose (race 1), cowpea aphid (*Aphis craccivora*), pea aphid (*Acyrthosiphon pisum*), blue alfalfa aphid (*Acyrthosiphon kondoi*), spotted alfalfa aphid (*Therioaphis trifolii*), stem nematode (*Ditylenchus dipsaci*), root knot nematode (*Meloidogyne* sp.), and Leptosphaerulina leaf spot.

e) Control Variety

The low-lignin alfalfa variety may be compared to a control alfalfa variety. The control alfalfa variety may be a commercially available alfalfa variety grown in the same field conditions. For example, the commercially available alfalfa variety may be 55V12 (Pioneer Hi-Bred), 56S82 (Pioneer Hi-Bred, also referred to as "P56S82"), Althea (Alforex Seeds), Cisco II (Dairyland Seed, Inc.), Cornerstone (Winfield Solutions, LLC), CW 1010 (Alforex Seeds), Del Rio (Alforex Seeds), Fertilac 10 (Fertizona), HybriForce 2600 (Dairyland Seed, Inc.), HybriForce 700 (Dairyland Seed, Inc.), HybriForce-2400 (Dairyland Seed, Inc.), HybriForce-3400 (Dairyland Seed, Inc.), Keystone II (Alforex Seeds), Magnum 7 (Dairyland Seed, Inc.), Magnum 7-Wet (Dairyland Seed, Inc.), Mecca III (PGI Alfalfa, Inc.), N-R-Gee (Cornell University), P58N57 (Pioneer Hi-Bred), PGI 212, VR TOTAL (Alforex Seeds), PGI 529 (DOMINATOR) (Alforex Seeds), PGI 557 (LELIA) (Alforex Seeds), PGI 608 (Alforex Seeds), PGI 709 (Alforex Seeds), PGI 801 (Alforex Seeds), PGI 909 (Alforex Seeds), ROBUST (Alforex Seeds), PILLAR ST (Alforex Seeds), Sedona (NK Brand Alfalfa), StarGold (Alforex Seeds), SW7410 (S&W Seed Co.), WL 319 HQ (W-L Research), and WL 440HQ (W-L Research). The commercially available alfalfa variety may also be 5010 (Alforex Seeds), 243 STEALTH II (Alforex Seeds), 4N900 (Dairyland Seed, Inc.), 53Q6 (Pioneer Hi-Bred Int.) 54H11 (Pioneer Hi-Bred Int.), 54H91 (Pioneer Hi-Bred Int.), 54V46 (Pioneer Hi-Bred Int.), 55V50 (Pioneer Hi-Bred Int.), 59N59 (Pioneer Hi-Bred Int.), A 30-06 (ABI Alfalfa), A 4330 (Alforex Seeds), A 5225 (Alforex Seeds), Adrenalin (Alforex Seeds), Ameristand 403T (ABI Alfalfa), Ameristand 407TQ (ABI Alfalfa), Ascend (Alforex Seeds), Assalt ST (PickSeed), Barricade SLT (Alforex Seeds), Caliber (Alforex Seeds), Contender (Alforex Seeds), Croplan 9 (Winfield), CUF 101 (Univ. of California), CW 054004 (Alforex Seeds), CW 090075 (Alforex Seeds), CW 093009 (Alforex Seeds), CW 096043 (Alforex Seeds), CW 099079 (Alforex Seeds), CW 103009 (Alforex Seeds), CW 104015 (Alforex Seeds), CW 197 (Alforex Seeds), DS 1020 (Dairyland Seed, Inc.), DS 598 (Dairyland Seed, Inc.), Exalt (Alforex Seeds), eXclaim (Alforex Seeds), ForageGold (Alforex Seeds), Foremost II, Valid (Alforex Seeds), GH 717 (Dairyland Seed, Inc.), HybriForce-400 (Dairyland Seed, Inc.), Legend Extra (Alforex Seeds), Magna 995 (Dairyland Seed, Inc.), Optimus (Alforex Seeds), P59N59 (Pioneer Seeds), PERFORMER (Alforex Seeds), PGI 1007 BA (Alforex Seeds), PGI 215, Velvet (Alforex Seeds), PGI 437 (Alforex Seeds), PGI 437, Tower ST, PGI 459 (Alforex Seeds), PGI 459, Quest, PGI 459, Qwest, PGI 908S (Alforex Seeds), Pillar, Actis (Alforex Seeds), Rugged (Alforex Seeds), SHOWDOWN (Quality Seeds), SolarGold, CORNERSTONE (Alforex Seeds), SpringGold (Alforex Seeds), SummerGold (Alforex Seeds), Summit (Alforex Seeds), Sundance II, Sansar (Alforex Seeds), Super 10 (Alforex Seeds), SW 10 (S & W Seed Company), SW 9720 (S & W Seed Company), TS 4006 (Alforex Seeds), TS 4007 (Alforex Seeds), TS 4010 (Alforex Seeds), TS 4013 (Alforex Seeds), TS 4027 (Alforex Seeds), WinterKing II, Megan (Alforex Seeds), WinterKing III (Alforex Seeds), WL 357 HQ (W-L Research), WL 363 HQ (W-L Research), WL440 (W-L Research)

The control alfalfa variety may be in the same fall dormancy group as the low-lignin alfalfa variety. The control alfalfa variety may be in a different fall dormancy group as the low-lignin alfalfa variety. The control alfalfa variety may be a more dormant alfalfa variety compared to the low-lignin alfalfa variety.

3. CW096043

The present invention includes the seed of hybrid alfalfa variety CW096043 (also referred to as "CW 096043"). A deposit of CW096043 seeds has been made under the Budapest Treaty and in accordance with 37 C.F.R. §§ 1.801-1.809 on Aug. 14, 2015 with the American Type Culture Collection (ATCC), 10801 University Boulevard, Manassas, Va. 20110. The deposited seed has been granted Accession Number PTA-122473. The deposit will be maintained in the depository for a period of 30 years, or 5 years after the last request, or for the effective life of the patent, whichever is longer, and will be replaced as necessary during that period. Seeds, plants or plant parts derived from the seed deposited as Accession Number PTA-122473 are provided.

By "a plant derived from the seed deposited as Accession Number PTA-122473", it is meant a plant that is grown directly from the seed deposited as Accession Number PTA-122473, or a plant that is obtained indirectly from a plant grown from the seed deposited as Accession Number PTA-122473. Plants obtained indirectly from a plant grown from the seed deposited as Accession Number PTA-122473 may be grown from a vegetative cutting, seed, callus or tissue culture obtained from a plant or plant part grown from the seed deposited as Accession Number PTA-122473 or a clonal plant thereof.

CW 096043 is an advanced generation synthetic variety with 215 parents selected from a polycross among 8 clones selected for reduced lignin and increased digestibility. Parentage of CW 096043 traces to PGI 608 (12.5%), CW 26071 (12.5%), CW 056080 (12.5%), CW 066081 (37.5%), 06-7-514 (12.5%), and 06-7-525 (12.5%). CW 096043 was developed by choosing low ADL parent plants from a spaced plant nursery in fall 2008 and establishing cage 43 in 2009 from polycross progeny that survived cowpea aphid (*Aphis craccivora*) selection. CW096043 is a fall dormancy group 6 alfalfa variety.

4. CW103009

The present invention includes the seed of synthetic alfalfa variety designated CW103009 (also referred to as "CW 103009"). A deposit of CW103009 seeds has been made under the Budapest Treaty and in accordance with 37 C.F.R. §§ 1.801-1.809 on Aug. 14, 2015 with the American Type Culture Collection (ATCC), 10801 University Boulevard, Manassas, Va. 20110. The deposited seed has been granted Accession Number PTA-122475. The deposit will be maintained in the depository for a period of 30 years, or 5 years after the last request, or for the effective life of the patent, whichever is longer, and will be replaced as necessary during that period. Seeds, plants or plant parts derived from the seed deposited as Accession Number PTA-122475 are provided.

By "a plant derived from the seed deposited as Accession Number PTA-122475", it is meant a plant that is grown directly from the seed deposited as Accession Number PTA-122475, or a plant that is obtained indirectly from a plant grown from the seed deposited as Accession Number PTA-122475. Plants obtained indirectly from a plant grown from the seed deposited as Accession Number PTA-122475 may be grown from a vegetative cutting, seed, callus or tissue culture obtained from a plant or plant part grown from the seed deposited as Accession Number PTA-122475 or a clonal plant thereof.

CW 103009 is a synthetic variety with 12 parent plants selected for low acid detergent lignin (ADL), high RFQ (NDFD), high forage dry matter yield, and high forage milk per acre using Milk 2000. Parent plants were selected from a three year old Wisconsin selection nursery, crossed in the greenhouse, and bulk harvested as Synthetic generation 1. Nursery source plants composed of various populations that were developed by phenotypic recurrent selection for winter hardiness, high forage dry matter yield, low ADL and high NDFD (using Near Infrared Reflectance Spectroscopy), and for resistance to one or more of the following pests: bacterial wilt, Fusarium Wilt, Verticillium wilt, Phytophthora root rot, Aphanomyces root rot, anthracnose (race 1), and Leptospaherulina leaf spot. Parentage of CW 103009 traces to the following germplasm sources: CW 10-017 (Cal West) (50%), and CW10-018 (Cal West) (50%). Breeder seed was produced under cage isolation near Woodland, Calif. in 2010. Seed was bulk harvested from all parent plants as Synthetic generation 2. CW103009 is a fall dormancy group 3 alfalfa variety.

5. CW099079

The present invention includes the seed of synthetic alfalfa variety designated CW099079 (also referred to as "CW 099079"). A deposit of CW099079 seeds has been made under the Budapest Treaty and in accordance with 37 C.F.R. §§ 1.801-1.809 on Aug. 14, 2015 with the American Type Culture Collection (ATCC), 10801 University Boulevard, Manassas, Va. 20110. The deposited seed has been granted Accession Number PTA-122474. Access to this deposit will be available during the pendency of the application to the Commissioner of Patents and Trademarks and persons determined by the Commissioner to be entitled thereto upon request. All restrictions upon availability to the public will be irrevocably removed upon granting of the patent. The deposit will be maintained in the ATCC Depository, which is a public depository, for a period of 30 years, or 5 years after the most recent request, or for the enforceable life of the patent, whichever is longer. The viability of the deposit will be tested and will be replaced if it becomes nonviable during that period. Upon allowance of any claims in the application, the Applicant(s) will maintain and will make this deposit available to the public pursuant to the Budapest Treaty. Seeds, plants or plant parts derived from the seed deposited as Accession Number PTA-122474 are provided.

By "a plant derived from the seed deposited as Accession Number PTA-122474", it is meant a plant that is grown directly from the seed deposited as Accession Number PTA-122474, or a plant that is obtained indirectly from a plant grown from the seed deposited as Accession Number PTA-122474. Plants obtained indirectly from a plant grown from the seed deposited as Accession Number PTA-122474 may be grown from a vegetative cutting, seed, callus or tissue culture obtained from a plant or plant part grown from the seed deposited as Accession Number PTA-122474 or a clonal plant thereof.

CW 099079 is a synthetic variety with 209 parent plants which were selected for resistance to Blue Alfalfa Aphid, Stem Nematode, and Phytophthora root rot from a polycross among fifteen plants which were selected for low Acid Detergent Lignin (ADL) from spaced plant breeding nurseries. This pedigree is derived from various diverse populations which were developed by a combination of phenotypic recurrent selection and strain crossing with selection for resistance to one or more of the following pests: Fusarium wilt, Verticillium wilt, Phytophthora root rot, anthracnose (race 1), spotted alfalfa aphid, blue alfalfa aphid, stem nematode, and cowpea aphid and for low ADL. Parentage of CW 099079 traces to DK 194 (9%), SPS9000 (9%), WL 625 (4%), SW9628 (4%), CW 195 (3%), Millenia (1%), CW 194 Premium (1%), and miscellaneous Alforex Seeds breeding populations (69%). CW099079 is a fall dormancy group 9 alfalfa variety.

6. CW090075

The present invention includes the seed of synthetic alfalfa variety designated CW090075 (also referred to as "CW 090075"). A deposit of CW090075 seeds has been made under the Budapest Treaty and in accordance with 37 C.F.R. §§ 1.801-1.809 on Aug. 14, 2015 with the American Type Culture Collection (ATCC), 10801 University Boulevard, Manassas, Va. 20110. The deposited seed has been granted Accession Number PTA-122471. The deposit will be maintained in the depository for a period of 30 years, or 5 years after the last request, or for the effective life of the patent, whichever is longer, and will be replaced as necessary during that period. Seeds, plants or plant parts derived from the seed deposited as Accession Number PTA-122471 are provided.

By "a plant derived from the seed deposited as Accession Number PTA-122471", it is meant a plant that is grown directly from the seed deposited as Accession Number PTA-122471, or a plant that is obtained indirectly from a plant grown from the seed deposited as Accession Number PTA-122471. Plants obtained indirectly from a plant grown from the seed deposited as Accession Number PTA-122471 may be grown from a vegetative cutting, seed, callus or tissue culture obtained from a plant or plant part grown from the seed deposited as Accession Number PTA-122471 or a clonal plant thereof.

CW 090075 is a synthetic variety with 209 parent plants which were selected for resistance to Cowpea Aphid and Phytophthora root rot from a polycross among twenty plants which were selected for low Acid Detergent Lignin (ADL) from spaced plant breeding nurseries. This pedigree is derived from various diverse populations which were developed by a combination of phenotypic recurrent selection and strain crossing with selection for resistance to one or more of the following pests: Fusarium wilt, Verticillium wilt, Phytophthora root rot, anthracnose (race 1), spotted alfalfa aphid, blue alfalfa aphid, stem nematode, and cowpea aphid and for low ADL. Parentage of CW 090075 traces to PGI 1007BA (26%), Mirage (10%), CW 1010 (9%), DK 189 (4%), Super 10 (2%), Millenia (2%), DK 194 (2%), DK 191 (1%), and miscellaneous Alforex Seeds breeding populations (44%). CW090075 is a fall dormancy group 10 alfalfa variety.

7. CW054004

The present invention includes the seed of synthetic alfalfa variety designated CW054004 (also referred to as "CW 054004"). A deposit of CW054004 seeds has been made under the Budapest Treaty and in accordance with 37 C.F.R. §§ 1.801-1.809 on Aug. 14, 2015 with the American Type Culture Collection (ATCC), 10801 University Boulevard, Manassas, Va. 20110. The deposited seed has been granted Accession Number PTA-122470. The deposit will be maintained in the depository for a period of 30 years, or 5 years after the last request, or for the effective life of the patent, whichever is longer, and will be replaced as necessary during that period. Seeds, plants or plant parts derived from the seed deposited as Accession Number PTA-122470 are provided.

By "a plant derived from the seed deposited as Accession Number PTA-122470", it is meant a plant that is grown directly from the seed deposited as Accession Number PTA-122470, or a plant that is obtained indirectly from a plant grown from the seed deposited as Accession Number PTA-122470. Plants obtained indirectly from a plant grown from the seed deposited as Accession Number PTA-122470 may be grown from a vegetative cutting, seed, callus or tissue culture obtained from a plant or plant part grown from the seed deposited as Accession Number PTA-122470 or a clonal plant thereof.

CW 054004 is a synthetic variety with 11 parent plants selected for low Acid Detergent Lignin (ADL), high forage dry matter yield, high forage milk per acre using Milk 2000, and/or high forage NDFD. Parent plants were selected from a three year old Wisconsin selection nursery, crossed in the greenhouse, and bulk harvested as Synthetic generation 1. Nursery source plants composed of various populations that were developed by phenotypic recurrent selection for low Acid Detergent Lignin (ADL), winter hardiness, high forage dry matter yield, high NDFD (using Near Infrared Reflectance Spectroscopy), and for resistance to one or more of the following pests: bacterial wilt, Fusarium Wilt, Verticillium wilt, Phytophthora root rot, Aphanomyces root rot (race 1), Aphanomyces root rot (race 2), Anthracnose (race 1), and Leptosphaerulina leaf spot. Parentage of CW 054004 traces to the following germplasm sources: CW D4-005 (100%). Breeder seed was produced under cage isolation near Woodland, Calif. in 2005. Seed was bulk harvested from all parent plants as Synthetic generation 2. CW054004 is a fall dormancy group 4 alfalfa variety.

8. CW093009

The present invention includes the seed of synthetic alfalfa variety designated CW093009 (also referred to as "CW 093009"). A deposit of CW093009 seeds has been made under the Budapest Treaty and in accordance with 37 C.F.R. §§ 1.801-1.809 on Aug. 14, 2015 with the American Type Culture Collection (ATCC), 10801 University Boulevard, Manassas, Va. 20110. The deposited seed has been granted Accession Number PTA-122472. The deposit will be maintained in the depository for a period of 30 years, or 5 years after the last request, or for the effective life of the patent, whichever is longer, and will be replaced as necessary during that period. Seeds, plants or plant parts derived from the seed deposited as Accession Number PTA-093009 are provided.

By "a plant derived from the seed deposited as Accession Number PTA-093009", it is meant a plant that is grown directly from the seed deposited as Accession Number PTA-093009, or a plant that is obtained indirectly from a plant grown from the seed deposited as Accession Number PTA-093009. Plants obtained indirectly from a plant grown from the seed deposited as Accession Number PTA-093009 may be grown from a vegetative cutting, seed, callus or tissue culture obtained from a plant or plant part grown from the seed deposited as Accession Number PTA-093009 or a clonal plant thereof.

CW 093009 is a synthetic variety with 13 parent plants selected for low Acid Detergent Lignin (ADL), high forage dry matter yield, high forage milk per acre using Milk 2000, and/or high forage NDFD. Parent plants were selected from a three year old Wisconsin selection nursery, crossed in the greenhouse, and bulk harvested as Synthetic generation 1. Nursery source plants composed of various populations that were developed by phenotypic recurrent selection for low Acid Detergent Lignin (ADL), winter hardiness, high forage dry matter yield, high NDFD (using Near Infrared Reflectance Spectroscopy), and for resistance to one or more of the following pests: bacterial wilt, Fusarium Wilt, Verticillium wilt, Phytophthora root rot, Aphanomyces root rot (race 1), Aphanomyces root rot (race 2), Anthracnose (race 1), and Leptosphaerulina leaf spot. Parentage of CW 093009 traces to the following germplasm sources: CW 09-014 (50%), CW 09-015 (50%). Breeder seed was produced under cage isolation near Woodland, Calif. in 2009. Seed was bulk harvested from all parent plants as Synthetic generation 2. CW093009 is a fall dormancy group 3 alfalfa variety.

9. CW104015

The present invention includes the seed of synthetic alfalfa variety designated CW104015 (also referred to as "CW 104015"). A deposit of CW104015 seeds has been made under the Budapest Treaty and in accordance with 37 C.F.R. §§ 1.801-1.809 on Aug. 14, 2015 with the American Type Culture Collection (ATCC), 10801 University Boulevard, Manassas, Va. 20110. The deposited seed has been granted Accession Number PTA-122476. The deposit will be maintained in the depository for a period of 30 years, or 5 years after the last request, or for the effective life of the patent, whichever is longer, and will be replaced as necessary during that period. Seeds, plants or plant parts derived from the seed deposited as Accession Number PTA-122476 are provided.

By "a plant derived from the seed deposited as Accession Number PTA-122476", it is meant a plant that is grown directly from the seed deposited as Accession Number PTA-122476, or a plant that is obtained indirectly from a plant grown from the seed deposited as Accession Number PTA-122476. Plants obtained indirectly from a plant grown from the seed deposited as Accession Number PTA-122476 may be grown from a vegetative cutting, seed, callus or tissue culture obtained from a plant or plant part grown from the seed deposited as Accession Number PTA-122476 or a clonal plant thereof.

CW 104015 is a synthetic variety with 17 parent plants selected for low Acid Detergent Lignin (ADL), high forage dry matter yield, high forage milk per acre using Milk 2000, and/or high forage NDFD. Parent plants were selected from a three year old Wisconsin selection nursery, crossed in the greenhouse, and bulk harvested as Synthetic generation 1. Nursery source plants composed of various populations that were developed by phenotypic recurrent selection for low Acid Detergent Lignin (ADL), winter hardiness, high forage dry matter yield, high NDFD (using Near Infrared Reflectance Spectroscopy), and for resistance to one or more of the following pests: bacterial wilt, Fusarium Wilt, Verticillium wilt, Phytophthora root rot, Aphanomyces root rot (race 1), Aphanomyces root rot (race 2), Anthracnose (race 1), and Leptosphaerulina leaf spot. Parentage of CW 104015 traces to the following germplasm sources: Adrenalin (6%), WinterKing III (6%), SolarGold (18%), CW 09-039 (35%), CW 09-040 (35%). Breeder seed was produced under cage isolation near Woodland, Calif. in 2010. Seed was bulk harvested from all parent plants as Synthetic generation 2. CW104015 is a fall dormancy group 4 alfalfa variety.

10. USES OF LOW-LIGNIN ALFALFA PLANT

The present invention contemplates using the low-lignin alfalfa plant, or part thereof, or an alfalfa plant having the physiological and morphological characteristics of the low-lignin alfalfa plant, as a source of breeding material for developing or producing an alfalfa plant in an alfalfa breeding program using plant breeding techniques. Plant breeding techniques useful in the developing or producing alfalfa plants include, but are not limited to, single seed descent, modified single seed descent, recurrent selection, reselection, mass selection, bulk selection, backcrossing, pedigree breeding, mutation breeding, restriction fragment length polymorphism enhanced selection, genetic marker enhanced selection, and transformation. Plant breeding techniques are known to the art and have been described in the literature.

Methods are provided for introducing or introgres sing a desired trait into alfalfa low-lignin. High yield alfalfa plants are inter-mated to produce the next generation of seed. Seed from the first cycle, is re-selected, and inter-mated to produce the next generation of high yield plants. This process of selection and inter-mating is conducted until desired level of yield is achieved. Plants are produced that have the desired trait and all the physiological and morphological characteristics of alfalfa variety low-lignin.

As used herein, the term "plant" includes, but is not limited to, plant cells, plant protoplasts, plant cell tissue cultures from which alfalfa plants can be regenerated, plant calli, plant clumps, and plant cells that are intact in plants or parts thereof. "Plant part" includes, but is not limited to, embryos, pollen (pollen grains), ovules, seeds, flowers, pods, leaves, roots, root tips, anthers, and the like.

One may obtain alfalfa plants according to the present invention by directly growing the seed low-lignin or by any other means. An alfalfa plant having all of the physiological and morphological characteristics of low-lignin can be obtained by any suitable methods, including, but not limited to, regenerating plants or plant parts from tissue culture or cuttings. The scope of the present invention is not limited by the method by which the plant is obtained.

The present invention contemplates genetic transformation of the low-lignin alfalfa plants. Polynucleotides may be introduced into a plant cell of alfalfa low-lignin to produce a transgenic low-lignin alfalfa plant. At least one, two, three, four, five, six, seven, eight, nine or ten polynucleotides may be introduced. As used herein, "introduced into a plant" with respect to polynucleotides encompasses the delivery of a polynucleotide into a plant, plant tissue, or plant cell using any suitable polynucleotide delivery method. Methods suitable for introducing polynucleotides into a plant useful in the practice of the present invention are well known in the art and include, but are not limited to, freeze-thaw method, microparticle bombardment, direct DNA uptake, whisker-mediated transformation, electroporation, sonication, microinjection, plant virus-mediated, and Agrobacterium-mediated transfer to the plant. Any suitable Agrobacterium strain, vector, or vector system for transforming the plant may be employed according to the present invention.

In some embodiments, a plant may be regenerated or grown from the plant, plant tissue or plant cell. Any suitable methods for regenerating or growing a plant from a plant cell or plant tissue may be used, such as, without limitation, tissue culture or regeneration from protoplasts. Suitably, plants may be regenerated by growing transformed plant cells on callus induction media, shoot induction media and/or root induction media. The regenerated plants have substantially all the morphological and physiological characteristics of the alfalfa variety named low-lignin that are described in the attached tables.

In certain embodiments, the polynucleotides to be introduced into the plant are operably linked to a promoter sequence and may be provided as a construct. As used herein, a polynucleotide is "operably linked" when it is placed into a functional relationship with a second polynucleotide sequence. For instance, a promoter is operably linked to a coding sequence if the promoter is connected to the coding sequence such that it may effect transcription of the coding sequence. In various embodiments, the polynucleotides may be operably linked to at least one, at least two, at least three, at least four, at least five, or at least ten promoters.

Promoters that may be used include, but are not limited to, constitutive, inducible, temporally-regulated, developmentally regulated, chemically regulated, tissue-preferred and tissue-specific promoters. Suitably, the promoter causes sufficient expression in the plant to produce the phenotypes described herein. Suitable promoters include, without limitation, the 35S promoter of the cauliflower mosaic virus, ubiquitin, tCUP cryptic constitutive promoter, the Rsyn7 promoter, pathogen-inducible promoters, the maize In2-2 promoter, the tobacco PR-1a promoter, glucocorticoid-inducible promoters, and tetracycline-inducible and tetracycline-repressible promoters.

Polynucleotides may also be provided in a vector. Suitable vectors include plasmids and virus-derived vectors. Vectors known in the art that are suitable for transformation into plants, cloning, and protein expression may be used.

The present invention relates to transformed versions of the claimed alfalfa variety with low-lignin as well as hybrid combinations thereof.

Polynucleotides that may be used include, but are not limited to, those that alter an agronomic trait such as conferring resistance to insects, disease, herbicides, or abiotic stress, or by altering fatty acid metabolism, carbohydrate metabolism, starch metabolism, amino acid metabolism, phosphorus metabolism, antioxidant metabolism, male sterility, site specific DNA integration, plant growth, forage yield and flowering. Examples of such traits are described in U.S. Pat. No. 6,652,195, the entire disclosure of which is herein incorporated by reference.

Polynucleotides that may be introduced include those that confer resistance to insects or disease, including, without limitation, coding sequences for plant disease resistance such as tomato Cf-9 for resistance to *Cladosporium falvum*, tomato Pto for resistance to *Pseudomonas syringae* pv. Tomato, Arabidopsis RSP2 for resistance to *Pseudomonas syringae*, *Bacillus thuringiensis* (bt) protein, insect-specific hormones or pheromones and variants and mimetics, such as an ecdysteroid and juvenile hormones. Examples are described in U.S. Pat. Nos. 5,188,960, 5,689,052, and 5,880,275, the entire disclosures of which are each herein incorporated by reference. A plant resistant to a disease is one that is more resistant to a pathogen as compared to the wild type plant.

Polynucleotides that may be introduced include those that confer resistance to a herbicide, including, without limitation, coding sequences for aryloxyalkanoate dioxygenase (AAD), coding sequences for mutant ALS and AHAS enzymes, coding sequences for glyphosate resistance imparted by mutant 5-enolpyruvl-3-phosphikimate synthase (EPSP), glyphosate N-acetyltransferase, glyphosate oxidoreductase and aroA; coding sequences for glufosinate resistance (phosphinothricin acetyl transferase (PAT) and Streptomyces hygroscopicus phosphinothricin acetyl transferase (bar); pyridinoxy or phenoxy proprionic acids and cycloshexones (ACCase inhibitor-encoding genes); triazine (psbA and gs+ genes); benzonitrile (nitrilase gene); coding sequences for acetohydroxy acid synthase; coding sequences for a chimeric protein of rat cytochrome P4507A1 and yeast NADPH-cytochrome P450 oxidoreductase; coding sequences for glutathione reductase and superoxide dismutase; coding sequences for various phosphotransferases; and coding sequences for modified protoporphyrinogen oxidase (protox). Examples are described in U.S. Pat. Nos. 8,785,728, 8,748,700, 8,685,677, 7,939,721, 4,975,374, 5,776,760, 5,463,175, 5,969,213, 5,489,520, 5,550,318, 5,874,265, 5,919,675, 5,561,236, 5,648,477, 5,646,024, 6,566,587, 6,338,961, 6,248,876 B1, 6,040,497, 5,969,213, 5,489,520, 5,550,318, 5,874,265, 5,919,675, 5,561,236, 5,648,477, 5,646,024, 6,177,616, 5,879,903, 5,804,425, 5,633,435, 5,145,783, 4,971,908, 5,312,910, 5,188,642, 4,940,835, 5,866,775, 6,225,114 B1, 6,130,366, 5,310,667, 4,535,060, 4,769,061, 5,633,448, 5,510,471, RE 36,449, RE 37,287, and 5,491,288, the entire disclosures of which are each herein incorporated by reference.

Polynucleotides that may be introduced include those that confer or contribute to an altered trait such as altered fatty acids, include, for example, coding sequences for stearoyl-ACP desaturase, FAD-2, FAD-3, LEC1, AGP, Dek1, Superall, milps, various Ipa genes such as Ipa1, Ipa3, hpt or hggt. Examples are described in U.S. Pat. Nos. 6,063,947, 6,323, 392, 6,372,965, 6,423,886, 6,197,561, and 6,825,397, and US Patent Publication Nos. 2003/0079247 and 2003/0204870, the entire disclosures of which are each herein incorporated by reference.

Polynucleotides that may be introduced include those that confer or contribute to an altered trait such as altered phosphorus content, include, for example, coding sequences for a phytase, inositol kinase or for LPA alleles. Examples are described in U.S. Pat. Nos. 6,197,561, 6,291,224, and 6,391,348, and US Patent Publication Nos. 2003/0009011, 2003/0079247, and 2003/0079247, the entire disclosures of which are each herein incorporated by reference.

Polynucleotides that confer or contribute to an altered trait such as altered carbohydrate metabolism, include coding sequences for enzymes of starch and cellulose metabolism, such as thioredoxin, fructosyltransferase, levansucrase, alpha-amylase, invertase, starch branching enzyme, UDP-D-xylose 4-epimerase, cellulose synthases (CesA), UDPglucose pyrophosphorylase, glycosyl transferase, and glycosyl hydrolase. Examples are described in U.S. Pat. Nos. 6,531,648, 6,232,529, 6,194,638, 6,803,498, 6,194,638, 6,399,859 and US Patent Publication Nos. 2003/0163838, 2003/0150014, 2004/0068767, and 2004/0025203, the entire disclosures of which are each herein incorporated by reference.

Polynucleotides that may be introduced include those that confer or contribute to an altered trait such as altered antioxidant content or composition, include, for example, coding sequences for a phytyl prenyl transferase (ppt), or homogentisate geranyl geranyl transferase (hggt). Examples are described in U.S. Pat. No. 6,787,683, and US Patent Publication No. 2004/0034886, the entire disclosures of which are each herein incorporated by reference.

Polynucleotides that may be introduced include those that confer or contribute to an altered trait such as altered amino acids, include for example, coding sequences for plant amino acid biosynthetic enzymes, coding sequences for plant tryptophan synthase, or coding sequences for methionine metabolic enzymes. Examples are described in U.S. Pat. Nos. 6,127,600, 5,990,389, 5,850,016, 5,885,802, 5,885,801 6,664,445 6,459,019 6,441,274 6,346,403, 5,939, 599, 5,912,414, 5,633,436, and 5,559,223, the entire disclosures of which are herein incorporated by reference.

Polynucleotides that may be introduced include those that confer or contribute to an altered trait such as male sterility. For example coding sequences for a deacetylase gene, the use of stamen-specific promoters, barnase and barstar genes may be used. Examples are described in U.S. Pat. Nos. 5,432,068, 4,654,465, 4,727,219, 3,861,709, and 3,710,511, the disclosures of each of which are herein incorporated by reference in their entireties.

Polynucleotides that may be introduced include those that create a site for site specific DNA integration, such as the introduction of FRT sites that may be used in the FLP/FRT system and/or Lox sites that may be used in the Cre/Loxp system.

Polynucleotides that may be introduced include those that alter abiotic stress resistance (including but not limited to flowering, ear and seed development, enhancement of nitrogen utilization efficiency, altered nitrogen responsiveness, drought resistance or tolerance, cold resistance or tolerance, and salt resistance or tolerance) See for example, U.S. Pat. Nos. 5,892,009, 5,965,705, 5,929,305, 5,891,859, 6,417, 428, 6,664,446, 6,706,866, 6,717,034, 6,801,104, 6,084,153, 6,177,275, and 6,107,547, and US Patent Publication Nos. 20040128719, 20030166197, 20040098764, and 20040078852. The disclosures of each of these documents are herein incorporated by reference in their entireties.

Polynucleotides that may be introduced include those that alter plant growth and agronomic traits such as yield, flowering, plant growth and/or plant structure. Examples are described in U.S. Pat. Nos. 6,573,430, 6,713,663 6,794,560, and 6,307,126, the disclosures of each of which are herein incorporated by reference in their entireties.

The present invention has multiple aspects, illustrated by the following non-limiting examples.

11. EXAMPLES

The foregoing may be better understood by reference to the following examples, which are presented for purposes of illustration and are not intended to limit the scope of the invention.

Example 1

Methods and Materials

The year the alfalfa plants were planted is considered "Year 0." Plants harvested in the same calendar year of planting are considered "Year 0" harvested plants; plants harvested in the next calendar year after planting are considered "Year 1" harvested plants; plants harvested two calendar years after planting are considered "Year 2" harvested plants; plants harvested three calendar years after planting are considered "Year 3" harvested plants; and plants harvested four calendar years after planting are considered "Year 4" harvested plants.

Dormant Forage Yield Trials:

Experimental design was randomized complete block with 3 replications. Trials were seeded at 20 lbs per acres. The plot size used was 4' wide by 15' long (7 rows per plot with 6 inch spacing or outside row to row was 36"). Forage was harvested at 28, 35, and/or 42 days depending on the trial. Plots were harvested at approximately 10 cm height. Yield is reported in tons/acre. Plots were fertilized using 400 lbs/ac annually of 1-2-20-12s (applied after each cutting to achieve the 400 lbs annually). Insects (potato leaf hoppers (*Empoasca fabae*)) were controlled as needed using Baythroid insecticide at rate 2 oz/acre. Weeds were controlled during year of establishment using post emergence application Raptor herbicide at 4-6 oz/acre rate.

Forage Quality Sampling:

The alfalfa plants were analyzed at various stages of maturity from 28 to 42 days or Bud Stage to Bloom stage, including Stages 1, 2, and 3, where each stage is a specific number of days after prior cut/harvest where applicable: Stage 1—Early (about 21 days); Stage 2—Medium (about 28 days); and Stage 3—Late (about 35 days). Forage digestibility typically decreases with higher stages, whereas the total yield typically increases with higher stages. Samples were taken by cutting stems at 10 cm height from soil surface using an 18" section of 2×4" board to ensure uniform cutting height. Samples were placed in perforated plastic flats in forced air oven at 60° C. or 140° F. for 48 hrs. Samples were ground through 4 mm screen using a Wiley mill or chop grinder. Samples were then blended using wearing blended to ensure ground leaves and stems were well mixed. Samples were then ground through 1 mm screen using an Udy mill or abrasion grinder and place in a 120 ml specimen sample cups. Samples were the then tumbled in a drum to ensure no particle size separation prior to scanning. Samples were allowed to equilibrate to 22-24° C. prior to scanning in ring cup on a Foss 5000 NIR Spectrometer. Forage quality estimates were predicted using the NIRS Forage and Feed Testing Consortium Alfalfa Breeders equation and/or Rock River Labs TTDNDF equation.

Semi- and Non-Dormant Forage Yield Trials.

The plot size used was 3' wide by 16' long (5 rows per plot on 6 inch spacing or outside row to row was 24"). The cutting height was 1.75 inches from soil surface with a 2×4" board laying flat. Different fertility, insect, and weed control program were used. Flood irrigation was performed between cuttings. In Woodland Calif., samples were cute at 1.75 inches (4.4 cm—the depth if a 2×4 board laid on the soil next to the rows to be sampled). The plots were 16 feet in length. 4 replications were performed.

Chemical Applications:

A pre-plant herbicide Balan DF and Eptam 7E was incorporated with a rototiller followed by a ring roller for semi compact soil bed. The targeted insects were armyworms, alfalfa caterpillar, lygus, aphids, and thrips. Warrior II (1.9 oz per ac) and Beseige (10 oz per ac) were used for control. For weed control after establishment, Raptor (6 oz per ac), Pursuit (6 oz per ac) and Velpar (5 pts per ac) were used. The fields were flood irrigated 2 to 3 times per between cuttings (up to 7 cuttings per season).

Example 2

Forage Yield—CW096043

The total forage yield, as dry matter in tons per acre, and stand of CW096043 was determined over four years and compared to commercial fall dormancy group 6 varieties (Table 1). Stand refers to the final stand percentage and is a measure of persistence. Tests were conducted at Woodland, Calif. The forage quality was measured with 5, 6, or 7 cuts per year for a total of 24 cuts.

TABLE 1

| Variety | Total Forage Yield (DM) | | | | | |
|---|---|---|---|---|---|---|
| | Year 1 (5 cuts) | Year 2 (7 cuts) | Year 3 (6 cuts) | Year 4 (6 cuts) | TOTAL (24 cuts) | Stand Year 4 |
| CW 096043 | 8.35 | 10.10 | 10.20 | 9.78 | 38.43 | 71.3 |
| Del Rio (CW) | 8.03 | 9.58 | 9.63 | 8.55 | 35.78 | 60.0 |
| 56S82 | 7.95 | 9.10 | 9.50 | 8.95 | 35.50 | 58.8 |
| PGI 608 | 8.40 | 10.10 | 9.88 | 8.80 | 37.18 | 62.5 |
| WL 440HQ | 8.63 | 9.20 | 9.50 | 9.05 | 36.38 | 60.0 |

Example 3

Forage Quality—CW096043

The forage quality of CW096043 at Stages 1 (about 21-22 days after clipping), 2 (about 28-29 days after clipping), and 3 (about 35 days after clipping) was compared to various commercially available alfalfa varieties using the methods described in Example 1. The forage quality data, as an average of 3 cuts, are presented in Tables 2-4 for Year 3 harvested plants and Tables 5-7 for Year 4 harvested plants. In Tables 2-4, CW096043 was compared to fall dormancy group 6 alfalfa varieties P56S82 and PGI 608, fall dormancy group 7 alfalfa varieties HybriForce 700 and PGI 709, fall dormancy group 8 alfalfa varieties P58N57 and PGI 801, fall dormancy group 9 alfalfa varieties Mecca III and PGI 909, and fall dormancy group 10 alfalfa varieties CW 1010 and Fertilac 10. In Tables 5-7, CW096043 was compared to fall dormancy group 6 alfalfa varieties P56S82, PGI 608, and WL440, fall dormancy group 7 alfalfa varieties HybriForce 700, PGI 709, and SW7410, fall dormancy group 9 alfalfa varieties Mecca III and PGI 909, and fall dormancy group 10 alfalfa varieties CW 1010, Fertilac 10, and Sedona.

TABLE 2

| CW096043 (Year 3): Stage 1: Average of 3 cuts | | | | | | | | | |
|---|---|---|---|---|---|---|---|---|---|
| Variety | CP | ADF | aNDF | ADL | DM | IVTDMD | NDFD1 | TTNDFD | Dyn Kd |
| CW 096043 | 25.20 | 26.26 | 31.29 | 5.13 | 91.63 | 85.01 | 49.50 | 36.57 | 8.26 |
| CW 1010 | 23.17 | 29.42 | 35.06 | 5.91 | 91.82 | 82.13 | 47.20 | 31.67 | 7.34 |
| Fertilac 10 | 22.75 | 30.17 | 35.99 | 6.07 | 91.88 | 81.34 | 46.75 | 30.81 | 6.96 |
| HybriForce 700 | 24.60 | 27.14 | 32.51 | 5.40 | 91.77 | 83.78 | 48.36 | 33.82 | 8.30 |
| Mecca III | 23.89 | 28.54 | 33.97 | 5.76 | 91.77 | 82.81 | 47.85 | 33.16 | 7.62 |
| P56S82 | 24.56 | 26.82 | 32.19 | 5.27 | 91.72 | 84.26 | 49.22 | 33.65 | 8.87 |
| P58N57 | 23.69 | 28.49 | 34.08 | 5.77 | 91.75 | 82.78 | 47.66 | 31.93 | 7.90 |
| PGI 608 | 24.91 | 27.14 | 32.39 | 5.32 | 91.81 | 83.98 | 48.97 | 34.80 | 8.53 |
| PGI 709 | 24.16 | 28.54 | 33.92 | 5.63 | 91.85 | 83.01 | 48.30 | 33.34 | 8.24 |
| PGI 801 | 23.43 | 28.74 | 34.32 | 5.76 | 91.85 | 82.53 | 47.78 | 31.82 | 7.46 |
| PGI 909 | 22.98 | 29.85 | 35.49 | 5.99 | 91.76 | 81.61 | 46.66 | 30.61 | 7.14 |
| Grand Mean | 23.93 | 28.15 | 33.59 | 5.60 | 91.76 | 83.18 | 48.13 | 33.02 | 7.85 |
| LSD (0.05) | 0.89 | 1.00 | 1.18 | 0.23 | 0.18 | 0.86 | 0.79 | 1.97 | 0.94 |
| C.V. (%) | 2.63 | 2.52 | 2.48 | 2.91 | 0.14 | 0.73 | 1.16 | 4.22 | 8.49 |
| R2 | 0.69 | 0.78 | 0.77 | 0.80 | 0.38 | 0.79 | 0.76 | 0.64 | 0.57 |

TABLE 3

| CW096043 (Year 3): Stage 2: Average of 3 cuts | | | | | | | | | |
|---|---|---|---|---|---|---|---|---|---|
| Variety | CP | ADF | aNDF | ADL | DM | IVTDMD | NDFD1 | TTNDFD | Dyn Kd |
| CW 096043 | 22.23 | 30.09 | 35.63 | 6.06 | 90.97 | 81.22 | 45.94 | 28.88 | 6.70 |
| CW 1010 | 20.83 | 33.01 | 39.22 | 6.94 | 90.79 | 78.09 | 43.44 | 23.98 | 5.66 |
| Fertilac 10 | 20.47 | 33.19 | 39.49 | 6.95 | 90.82 | 77.90 | 43.16 | 24.17 | 5.48 |
| HybriForce 700 | 21.95 | 31.16 | 37.04 | 6.49 | 90.93 | 79.48 | 44.44 | 26.36 | 6.33 |
| Mecca III | 20.68 | 33.16 | 39.36 | 6.85 | 90.75 | 78.20 | 43.87 | 24.93 | 5.59 |
| P56S82 | 21.51 | 31.20 | 37.24 | 6.41 | 90.94 | 79.75 | 44.86 | 26.11 | 6.30 |
| P58N57 | 21.36 | 32.19 | 38.23 | 6.74 | 90.90 | 78.86 | 44.01 | 25.26 | 6.17 |
| PGI 608 | 21.94 | 31.65 | 37.44 | 6.40 | 91.15 | 79.56 | 44.94 | 26.59 | 6.53 |
| PGI 709 | 21.75 | 32.06 | 37.99 | 6.57 | 91.09 | 79.12 | 44.69 | 26.43 | 6.44 |
| PGI 801 | 20.93 | 32.79 | 39.05 | 6.78 | 90.83 | 78.38 | 43.98 | 24.17 | 5.84 |
| PGI 909 | 20.67 | 33.26 | 39.45 | 6.92 | 90.86 | 78.08 | 43.44 | 24.32 | 5.73 |
| Grand Mean | 21.35 | 31.97 | 37.96 | 6.60 | 90.87 | 79.20 | 44.41 | 25.73 | 6.11 |
| LSD (0.05) | 0.65 | 1.05 | 1.18 | 0.25 | 0.26 | 0.86 | 0.82 | 1.59 | 0.49 |
| C.V. (%) | 2.17 | 2.32 | 2.20 | 2.67 | 0.20 | 0.77 | 1.31 | 4.38 | 5.68 |
| R2 | 0.66 | 0.69 | 0.72 | 0.74 | 0.51 | 0.76 | 0.69 | 0.67 | 0.63 |

TABLE 4

| Variety | CP | ADF | aNDF | ADL | DM | IVTDMD | NDFD1 | TTNDFD | Dyn Kd |
|---|---|---|---|---|---|---|---|---|---|
| CW 096043 | 20.39 | 33.27 | 39.49 | 6.83 | 90.96 | 78.23 | 43.43 | 27.11 | 6.42 |
| CW 1010 | 18.85 | 35.79 | 42.66 | 7.75 | 90.99 | 75.32 | 40.92 | 23.02 | 5.41 |
| Fertilac 10 | 18.92 | 35.59 | 42.57 | 7.52 | 90.50 | 75.19 | 40.60 | 21.94 | 4.73 |
| HybriForce 700 | 19.37 | 34.62 | 41.33 | 7.33 | 91.10 | 76.14 | 41.44 | 24.21 | 5.86 |
| Mecca III | 18.81 | 36.25 | 43.22 | 7.62 | 90.77 | 74.98 | 41.11 | 23.73 | 5.01 |
| P56S82 | 19.30 | 35.02 | 41.74 | 7.35 | 91.11 | 76.02 | 41.81 | 24.19 | 5.64 |
| P58N57 | 19.15 | 35.16 | 42.07 | 7.61 | 90.97 | 75.53 | 40.81 | 22.92 | 5.68 |
| PGI 608 | 19.99 | 34.28 | 40.83 | 7.26 | 91.00 | 76.40 | 41.60 | 23.99 | 5.96 |
| PGI 709 | 19.94 | 34.21 | 40.75 | 7.24 | 90.91 | 76.80 | 42.30 | 23.88 | 5.86 |
| PGI 801 | 19.25 | 35.67 | 42.59 | 7.58 | 90.74 | 75.12 | 40.87 | 22.58 | 5.28 |
| PGI 909 | 18.53 | 36.88 | 43.74 | 7.75 | 90.96 | 74.64 | 40.96 | 23.26 | 5.20 |
| Grand Mean | 19.38 | 34.90 | 41.58 | 7.37 | 90.92 | 76.17 | 41.64 | 24.07 | 5.64 |
| LSD (0.05) | 0.60 | 1.07 | 1.24 | 0.26 | 0.59 | 1.11 | 0.94 | 1.94 | 0.63 |
| C.V. (%) | 2.20 | 2.16 | 2.10 | 2.53 | 0.46 | 1.03 | 1.59 | 5.71 | 7.96 |
| R2 | 0.70 | 0.72 | 0.74 | 0.75 | 0.40 | 0.70 | 0.68 | 0.68 | 0.57 |

TABLE 5

CW096043 (Year 4): Stage 1: Average of 3 cuts

| Variety | CP | ADF | aNDF | ADL | DM | IVTDMD | NDFD1 | TTNDFD | Dyn Kd |
|---|---|---|---|---|---|---|---|---|---|
| CW 096043 | 24.13 | 28.20 | 33.84 | 5.64 | 92.39 | 81.69 | 48.38 | 28.68 | 7.51 |
| CW 1010 | 23.09 | 30.16 | 36.23 | 6.12 | 92.54 | 79.68 | 46.84 | 26.26 | 7.04 |
| Fertilac 10 | 23.15 | 30.14 | 36.07 | 6.09 | 92.47 | 79.90 | 46.79 | 25.83 | 6.60 |
| HybriForce 700 | 23.75 | 28.26 | 34.17 | 5.76 | 92.29 | 80.99 | 47.39 | 26.30 | 7.19 |
| Mecca III | 23.73 | 28.81 | 34.71 | 5.88 | 92.44 | 81.05 | 47.57 | 27.61 | 7.23 |
| P56S82 | 23.93 | 28.45 | 34.33 | 5.78 | 92.43 | 80.93 | 47.98 | 27.05 | 7.43 |
| PGI 608 | 24.19 | 28.49 | 34.29 | 5.70 | 92.36 | 81.14 | 47.80 | 27.73 | 7.44 |
| PGI 709 | 23.82 | 28.82 | 34.70 | 5.85 | 92.45 | 81.18 | 47.57 | 27.90 | 7.40 |
| PGI 909 | 22.97 | 30.27 | 36.20 | 6.21 | 92.52 | 79.35 | 46.68 | 25.88 | 6.70 |
| Sedona | 22.93 | 29.77 | 35.79 | 6.10 | 92.37 | 79.80 | 46.81 | 25.65 | 6.50 |
| SW7410 | 23.40 | 29.07 | 34.96 | 5.91 | 92.43 | 80.85 | 47.10 | 27.54 | 6.88 |
| WL440 | 23.91 | 28.55 | 34.30 | 5.74 | 92.47 | 81.10 | 47.83 | 27.20 | 7.45 |
| Grand Mean | 23.58 | 29.09 | 34.98 | 5.90 | 92.43 | 80.65 | 47.41 | 26.95 | 7.12 |
| LSD (0.05) | 0.86 | 1.38 | 1.54 | 0.31 | 0.15 | 1.13 | 0.82 | 1.55 | 0.76 |
| C.V. (%) | 2.59 | 3.37 | 3.11 | 3.68 | 0.12 | 0.99 | 1.23 | 4.06 | 7.55 |
| R2 | 0.56 | 0.48 | 0.49 | 0.53 | 0.52 | 0.54 | 0.58 | 0.60 | 0.45 |

TABLE 6

CW096043 (Year 4): Stage 2: Average of 3 cuts

| Variety | CP | ADF | aNDF | ADL | DM | IVTDMD | NDFD1 | TTNDFD | Dyn Kd |
|---|---|---|---|---|---|---|---|---|---|
| CW 096043 | 21.56 | 29.95 | 36.03 | 6.24 | 92.79 | 80.40 | 46.03 | 28.64 | 6.72 |
| CW 1010 | 20.01 | 32.98 | 39.37 | 7.01 | 92.90 | 77.49 | 43.85 | 25.29 | 5.76 |
| Fertilac 10 | 19.63 | 33.90 | 40.40 | 7.27 | 92.84 | 75.92 | 42.67 | 24.37 | 5.61 |
| HybriForce 700 | 21.33 | 31.21 | 37.45 | 6.68 | 92.79 | 78.39 | 44.70 | 26.82 | 6.53 |
| Mecca III | 20.17 | 33.03 | 39.50 | 6.97 | 92.85 | 77.24 | 44.16 | 26.05 | 5.77 |
| P56S82 | 21.26 | 31.19 | 37.44 | 6.53 | 92.84 | 79.12 | 45.47 | 27.17 | 6.65 |
| PGI 608 | 21.39 | 31.79 | 38.05 | 6.70 | 92.85 | 78.17 | 44.86 | 26.77 | 6.67 |
| PGI 709 | 20.80 | 32.10 | 38.48 | 6.72 | 92.82 | 78.26 | 44.91 | 26.75 | 6.22 |
| PGI 909 | 19.64 | 33.86 | 40.39 | 7.17 | 92.90 | 76.90 | 43.38 | 25.04 | 5.79 |
| Sedona | 20.08 | 33.18 | 39.62 | 7.08 | 92.85 | 76.93 | 43.99 | 25.35 | 5.72 |
| SW7410 | 20.98 | 31.73 | 37.96 | 6.80 | 92.86 | 78.02 | 44.57 | 27.26 | 6.27 |
| WL440 | 20.50 | 32.97 | 39.32 | 6.89 | 92.83 | 77.75 | 44.54 | 25.94 | 6.02 |
| Grand Mean | 20.70 | 32.10 | 38.42 | 6.77 | 92.82 | 78.20 | 44.65 | 26.54 | 6.18 |
| LSD (0.05) | 0.62 | 0.95 | 1.06 | 0.25 | 0.12 | 0.91 | 0.88 | 0.99 | 0.44 |
| C.V. (%) | 2.13 | 2.09 | 1.95 | 2.64 | 0.09 | 0.83 | 1.39 | 2.64 | 5.07 |
| R2 | 0.78 | 0.80 | 0.80 | 0.79 | 0.60 | 0.83 | 0.77 | 0.88 | 0.72 |

TABLE 7

CW096043 (Year 4): Stage 3: Average of 3 cuts

| Variety | CP | ADF | aNDF | ADL | DM | IVTDMD | NDFD1 | TTNDFD | Dyn Kd |
|---|---|---|---|---|---|---|---|---|---|
| CW 096043 | 19.62 | 33.09 | 39.52 | 6.93 | 93.01 | 77.38 | 43.08 | 25.15 | 6.37 |
| CW 1010 | 18.30 | 35.68 | 42.52 | 7.67 | 93.09 | 74.61 | 41.24 | 22.94 | 5.43 |

TABLE 7-continued

CW096043 (Year 4): Stage 3: Average of 3 cuts

| Variety | CP | ADF | aNDF | ADL | DM | IVTDMD | NDFD1 | TTNDFD | Dyn Kd |
|---|---|---|---|---|---|---|---|---|---|
| Fertilac 10 | 17.55 | 37.19 | 44.12 | 8.12 | 93.24 | 72.80 | 39.57 | 21.63 | 5.12 |
| HybriForce 700 | 19.03 | 34.55 | 41.25 | 7.37 | 93.17 | 75.28 | 42.08 | 23.77 | 5.82 |
| Mecca III | 18.12 | 36.02 | 42.89 | 7.71 | 93.13 | 74.42 | 41.25 | 23.26 | 5.15 |
| P56S82 | 19.09 | 34.84 | 41.63 | 7.39 | 93.21 | 75.44 | 42.13 | 23.81 | 6.10 |
| PGI 608 | 19.74 | 34.55 | 41.11 | 7.40 | 93.06 | 75.28 | 42.00 | 23.89 | 6.09 |
| PGI 709 | 18.31 | 36.03 | 42.88 | 7.75 | 93.18 | 74.51 | 41.51 | 23.21 | 5.53 |
| PGI 909 | 17.66 | 37.25 | 44.27 | 8.08 | 93.13 | 73.08 | 39.84 | 22.21 | 5.30 |
| Sedona | 17.70 | 36.74 | 43.69 | 7.95 | 93.04 | 73.39 | 40.49 | 22.17 | 5.06 |
| SW7410 | 18.59 | 35.10 | 41.95 | 7.72 | 93.09 | 74.78 | 40.64 | 23.91 | 5.62 |
| WL440 | 18.97 | 35.58 | 42.38 | 7.45 | 93.16 | 74.93 | 42.24 | 23.42 | 5.72 |
| Grand Mean | 18.57 | 35.36 | 42.14 | 7.56 | 93.11 | 74.96 | 41.55 | 23.47 | 5.63 |
| LSD (0.05) | 0.61 | 1.22 | 1.35 | 0.33 | 0.19 | 1.14 | 1.11 | 1.14 | 0.40 |
| C.V. (%) | 2.31 | 2.43 | 2.27 | 3.06 | 0.14 | 1.08 | 1.89 | 3.42 | 4.97 |
| R2 | 0.79 | 0.71 | 0.72 | 0.74 | 0.48 | 0.76 | 0.70 | 0.69 | 0.74 |

Figure 2:
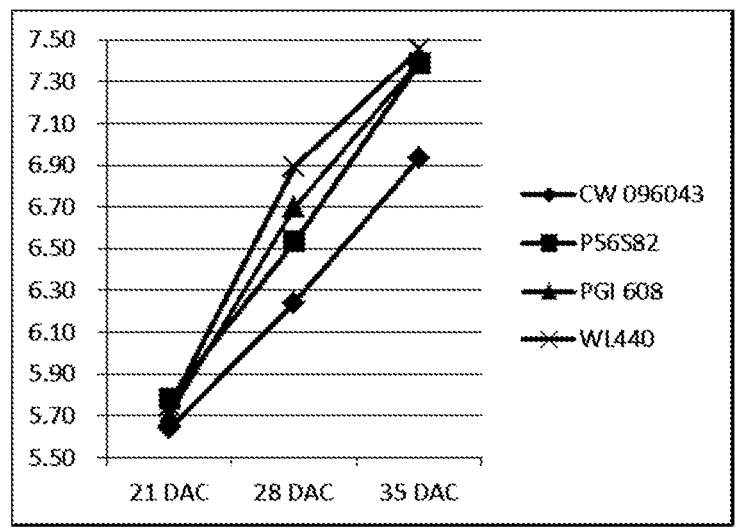
FIG. 2 shows the lignin content ("% ADL") after 21, 28, or 35 DAC of CW096043 compared to commercial varieties harvested in Year 4.

Table 8 and FIGS. 1 and 2 summarize the lignin content measured as ADL from Tables 2-7. Table 8 shows a comparison of CW 096043 with other commercially available fall dormancy group 6 alfalfa varieties. CW 096043 had about 6% less ADL compared to P56S82 in the 35 DAC sample.

TABLE 8

| | | % ADL | | |
|---|---|---|---|---|
| Year | Variety | 21 DAC | 28 DAC | 35 DAC |
| Year 3 | CW 096043 | 5.13 | 6.06 | 6.83 |
| | P56S82 | 5.32 | 6.4 | 7.26 |
| | PGI 608 | 5.27 | 6.41 | 7.35 |
| Year 4 | CW 096043 | 5.64 | 6.24 | 6.93 |
| | P56S82 | 5.78 | 6.53 | 7.39 |
| | PGI 608 | 5.7 | 6.7 | 7.4 |
| | WL440 | 5.74 | 6.89 | 7.45 |

Figure 3:
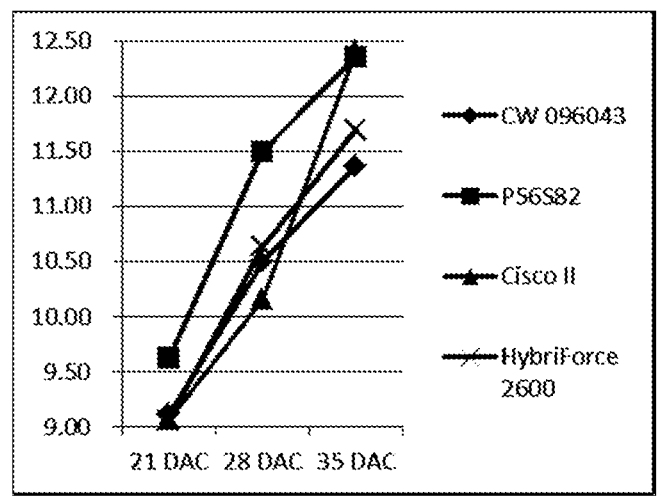
FIG. 3 shows the lignin content ("% ADL") after 21, 28, or 35 DAC in the lower stems of CW096043 compared to commercial varieties harvested in Year 1.
Figure 4:
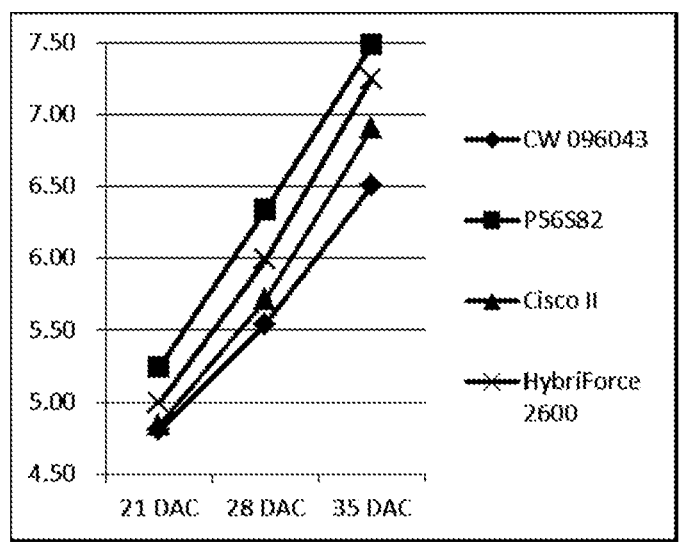
FIG. 4 shows the lignin content ("% ADL") after 21, 28, or 35 DAC in whole plants of CW096043 compared to commercial varieties harvested in Year 1.

Table 9 and FIGS. 3 and 4 show the amount of lignin (% ADL) in lower stems or whole plants of CW096043 compare to commercial varieties. Table 9 shows a comparison of CW 096043 with other commercially available fall dormancy group 6 alfalfa varieties. CW 096043 had about 8% and 13% less ADL in the lower stems and whole plant, respectively, compared to P56S82 in the 35 DAC sample.

TABLE 9

Lignin content measured as ADL

| Plant Material | Variety | % ADL | | |
|---|---|---|---|---|
| | | 21 DAC | 28 DAC | 35 DAC |
| Lower Stems | CW 096043 | 9.11 | 10.5 | 11.37 |
| | P56S82 | 9.62 | 11.5 | 12.36 |
| | Cisco II | 9.07 | 10.16 | 12.41 |
| | HybriForce 2600 | 9.06 | 10.64 | 11.7 |
| Whole Plant | CW 096043 | 4.81 | 5.54 | 6.51 |
| | P56S82 | 5.24 | 6.34 | 7.49 |
| | Cisco II | 4.84 | 5.72 | 6.91 |
| | HybriForce 2600 | 4.99 | 5.99 | 7.25 |

TABLE 9-continued

Lignin content measured as ADL

Figure 5:
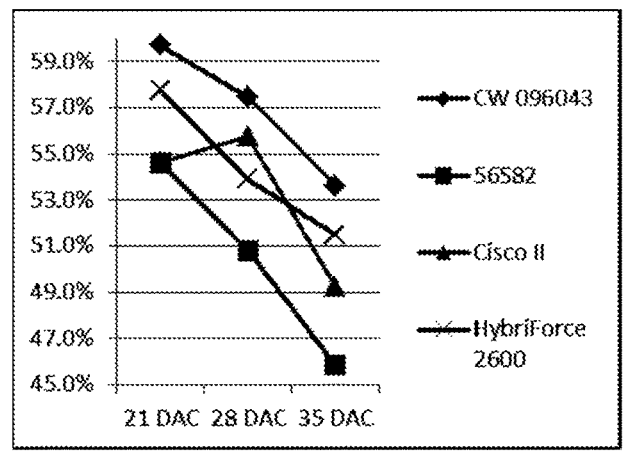
FIG. 5 shows the percentage of leaves (% Leaf) after 21, 28, or 35 DAC of CW096043 compared to commercial varieties harvested in Year 1.

Table 10 and FIG. 5 show the percentage of dry matter that is leaf tissue (% Leaf) as an average of cut 2 and cut 3 harvested in Year 1 of CW096043 plants compared to commercial varieties. The commercially available alfalfa varieties are fall dormancy group 6 alfalfa varieties. The amount of dry matter that is stem tissue is 1.00-(% Leaf). The Leaf:stem ratio reflects plant and canopy architecture and is an indirect determinant of forage quality, including lignin content.

TABLE 10

| | % Leaf | | |
|---|---|---|---|
| Variety | 21 DAC | 28 DAC | 35 DAC |
| CW 096043 | 59.70% | 57.50% | 53.60% |
| 56S82 | 54.60% | 50.80% | 45.80% |
| Cisco II | 54.70% | 55.80% | 49.20% |
| HybriForce 2600 | 57.80% | 53.90% | 51.50% |

Example 4

Forage Quality—CW096043

The forage quality of CW096043 (weighted mean of 3 cuts harvested in Year 2) was compared to various commercially available fall dormancy group 6 alfalfa varieties using the methods described in Example 1. The forage quality of CW096043 and the commercially available fall dormancy group 6 alfalfa varieties are shown in Table 11.

TABLE 11

| Variety | CP | ADF | aNDF | ADL | DM | IVTDMD | NDFD1 | Milk/Ton | Milk/Acre |
|---|---|---|---|---|---|---|---|---|---|
| CW 096043 | 25.35 | 25.69 | 30.91 | 4.68 | 89.82 | 83.91 | 48.13 | 3,330 | 33,625 |
| Del Rio | 25.27 | 26.62 | 31.97 | 4.8 | 90.03 | 83.38 | 48.2 | 3,284 | 31,444 |
| 56S82 | 24.41 | 26.68 | 32.35 | 4.92 | 89.88 | 82.95 | 47.58 | 3,260 | 29,684 |

TABLE 11-continued

| Variety | CP | ADF | aNDF | ADL | DM | IVTDMD | NDFD1 | Milk/Ton | Milk/Acre |
|---|---|---|---|---|---|---|---|---|---|
| PGI 608 | 24.49 | 27.94 | 33.43 | 5.15 | 90.16 | 82.1 | 47.21 | 3,205 | 32,361 |
| WL 440HQ | 24.98 | 26.8 | 32.2 | 4.84 | 89.89 | 83.02 | 47.74 | 3,267 | 30,063 |
| Trial Mean | 24.43 | 27.77 | 33.28 | 5.15 | 89.97 | 82.31 | 47.23 | 3,212 | 31,846 |
| LSD (.05) | 0.78 | 1.12 | 1.26 | 0.28 | 0.34 | 0.97 | 0.96 | 66 | 2,422 |
| CV % | 2.30% | 2.90% | 2.70% | 3.90% | 0.30% | 0.80% | 1.50% | 1.50% | 5.40% |

Example 5

Forage Quality—CW103009

The forage quality of CW103009 was compared to various commercially available alfalfa varieties using the methods described in Example 1. CW103009 and the commercially available alfalfa varieties were harvested in May, June, and July (Tables 12-14) in Year 1. The weighted mean for the three cuts is shown in Table 15. In Tables 12-15, CW103009 was compared to fall dormancy group 3 alfalfa variety WL 319 HQ, fall dormancy group 4 alfalfa variety HybriForce-400, and fall dormancy group 5 alfalfa variety 55V12. CW103009 had about 15% less ADL compared to SSV12.

TABLE 12

May Year 3 - cut 1

| Variety | CP | ADF | aNDF | ADL | DM | IVTDMD | NDFD1 | RFQ | RFV | Milk/ton | Milk/acre |
|---|---|---|---|---|---|---|---|---|---|---|---|
| CW 103009 | 24.58 | 25.44 | 30.89 | 5.18 | 92.42 | 84.76 | 52.51 | 222.76 | 208.14 | 3,275.31 | 8,815.89 |
| 55V12 | 22.96 | 28.11 | 34.16 | 6.13 | 92.70 | 82.04 | 47.90 | 188.48 | 182.58 | 3,098.39 | 7,833.78 |
| HybriForce-400 | 23.84 | 26.38 | 31.94 | 5.32 | 92.47 | 84.44 | 51.85 | 212.87 | 199.09 | 3,226.92 | 8,480.38 |
| WL 319 HQ | 24.79 | 26.07 | 31.49 | 5.29 | 92.64 | 84.74 | 51.83 | 215.12 | 203.00 | 3,201.97 | 8,465.12 |

TABLE 13

June Year 3 - cut 2

| Variety | CP | ADF | aNDF | ADL | DM | IVTDMD | NDFD1 | RFQ | RFV | Milk/ton | Milk/acre |
|---|---|---|---|---|---|---|---|---|---|---|---|
| CW 103009 | 20.62 | 21.41 | 27.22 | 4.31 | 94.12 | 86.54 | 50.64 | 263.86 | 247.11 | 3,662.21 | 7,221.02 |
| 55V12 | 19.70 | 24.00 | 30.20 | 5.11 | 94.84 | 84.10 | 48.22 | 230.68 | 217.02 | 3,545.78 | 6,266.51 |
| HybriForce-400 | 19.79 | 22.98 | 28.95 | 4.60 | 94.63 | 85.62 | 49.75 | 245.15 | 228.31 | 3,613.22 | 5,928.72 |
| WL 319 HQ | 19.76 | 22.30 | 28.36 | 4.52 | 94.22 | 85.76 | 49.44 | 249.83 | 234.88 | 3,622.02 | 6,333.83 |

TABLE 14

July Year 3 - cut 3

| Variety | CP | ADF | aNDF | ADL | DM | IVTDMD | NDFD1 | RFQ | RFV | Milk/ton | Milk/acre |
|---|---|---|---|---|---|---|---|---|---|---|---|
| CW 103009 | 24.42 | 28.03 | 33.01 | 5.98 | 93.51 | 82.16 | 47.31 | 196.29 | 189.30 | 3,168.07 | 5,503.74 |
| 55V12 | 22.61 | 31.43 | 37.12 | 6.80 | 94.21 | 78.88 | 43.11 | 161.23 | 161.62 | 2,960.96 | 4,750.55 |
| HybriForce-400 | 24.77 | 28.83 | 33.78 | 6.12 | 93.29 | 81.88 | 46.73 | 188.25 | 183.25 | 3,087.80 | 4,688.20 |
| WL 319 HQ | 24.27 | 28.55 | 33.46 | 6.12 | 93.88 | 82.12 | 47.01 | 193.24 | 185.58 | 3,170.15 | 4,889.73 |

TABLE 15

Year 3 - Weighted Mean

| Variety | CP | ADF | aNDF | ADL | DM | IVTDMD | NDFD1 | RFQ | RFV | Milk/ton | Milk/acre |
|---|---|---|---|---|---|---|---|---|---|---|---|
| CW 103009 | 23.32 | 24.89 | 30.33 | 5.12 | 93.23 | 84.60 | 50.51 | 228.25 | 215.10 | 3,365.03 | 21,540.66 |
| 55V12 | 21.87 | 27.79 | 33.78 | 6.01 | 93.75 | 81.79 | 46.68 | 193.61 | 187.12 | 3,194.88 | 18,850.84 |
| HybriForce-400 | 22.93 | 26.06 | 31.58 | 5.33 | 93.30 | 84.10 | 49.91 | 215.55 | 203.20 | 3,299.89 | 19,097.30 |
| WL 319 HQ | 23.18 | 25.61 | 31.08 | 5.28 | 93.42 | 84.36 | 49.88 | 219.65 | 207.85 | 3,316.90 | 19,688.68 |

Tables 16-25 show forage quality data for CW103009 and commercial alfalfa varieties grown in Wisconsin and harvested at about 35 days for three cuts in Year 1. In Tables 16-25, CW103009 was compared to fall dormancy group 2 alfalfa variety PGI 212, VR TOTAL, and ROBUST, fall dormancy group 3 alfalfa varieties Keystone II and WL 319 HQ, fall dormancy group 4 alfalfa varieties PILLAR ST, HybriForce-2400, HybriForce-3400, Magnum 7, Magnum 7-Wet, and N-R-Gee, fall dormancy group 5 alfalfa varieties 55V12, PGI 557, LELIA, Althea, PGI 529, DOMINATOR, and StarGold. The weighted mean for the three cuts is shown in Table 24. Table 26 shows the average forage quality values of CW103009 and commercial alfalfa varieties at 28, 35, and 42 DAC for 1 cut, as well as the average of 28, 35, and 42 DAC, measured in the whole plant. As shown in Table 26, the CW103009 had a reduction in lignin by 7-9% compared to the commercial alfalfa varieties. In Table 26, CW103009 was compared to fall dormancy group 3 alfalfa variety WL 319 HQ and fall dormancy group 5 alfalfa varieties 55V12 and PGI 557, LELIA.

TABLE 16

Year 1 (35 days)—Cut 1

| Variety | CP | ADF | aNDF | Lignin | DM | IVTDMD | NDFD1 | RFQ | RFV | Milk/ton | Milk/acre | TTNDFD | Dyn Kd |
|---|---|---|---|---|---|---|---|---|---|---|---|---|---|
| CW 103009 | 21.06 | 34.30 | 40.55 | 6.45 | 94.61 | 79.22 | 51.09 | 161.53 | 142.87 | 2,950.59 | 10,502.07 | 38.79 | 6.00 |
| 55V12 | 19.32 | 37.57 | 44.59 | 7.49 | 94.79 | 75.40 | 46.83 | 135.34 | 124.59 | 2,763.58 | 8,777.50 | 36.35 | 6.07 |
| ROBUST | 21.49 | 34.24 | 40.51 | 6.78 | 94.85 | 78.32 | 49.21 | 158.23 | 143.37 | 2,943.66 | 10,015.47 | 40.72 | 6.21 |
| PGI 212, VR TOTAL | 21.99 | 35.08 | 41.08 | 6.82 | 94.67 | 78.01 | 50.97 | 157.26 | 139.50 | 2,882.16 | 9,798.02 | 40.29 | 6.28 |
| PGI 557, LELIA | 19.86 | 37.03 | 43.44 | 7.11 | 94.66 | 76.67 | 49.57 | 145.56 | 128.86 | 2,827.59 | 9,585.65 | 35.94 | 5.62 |
| Althea | 20.94 | 35.42 | 41.71 | 7.05 | 94.75 | 76.79 | 49.15 | 153.17 | 138.17 | 2,886.69 | 9,076.78 | 38.20 | 6.00 |
| Keystone II | 20.54 | 36.05 | 42.37 | 6.79 | 94.99 | 77.57 | 51.14 | 155.18 | 135.25 | 2,898.55 | 9,538.34 | 39.83 | 5.80 |
| PGI 529, DOMINATOR | 19.41 | 36.54 | 43.21 | 7.18 | 94.91 | 75.87 | 48.41 | 144.93 | 130.26 | 2,859.39 | 9,450.76 | 37.88 | 5.85 |
| PILLAR ST | 18.98 | 40.20 | 47.28 | 8.06 | 94.67 | 72.32 | 46.58 | 124.91 | 114.49 | 2,618.90 | 8,946.42 | 33.48 | 5.49 |
| StarGold | 21.40 | 34.75 | 41.18 | 6.85 | 94.82 | 78.38 | 50.56 | 157.11 | 139.71 | 2,915.85 | 10,134.24 | 39.83 | 6.09 |
| HybriForce-2400 | 21.02 | 35.28 | 41.60 | 6.86 | 94.68 | 77.63 | 49.75 | 153.61 | 137.52 | 2,891.73 | 9,489.26 | 38.13 | 6.05 |
| HybriForce-3400 | 21.94 | 34.45 | 40.53 | 6.57 | 95.00 | 79.60 | 51.63 | 162.21 | 142.59 | 2,939.11 | 10,016.12 | 41.99 | 6.41 |
| Magnum 7 | 21.06 | 36.30 | 42.62 | 7.10 | 94.85 | 76.93 | 50.03 | 149.78 | 132.47 | 2,859.18 | 9,722.63 | 40.75 | 6.19 |
| Magnum 7-Wet | 20.58 | 36.26 | 42.90 | 7.08 | 94.84 | 76.36 | 49.75 | 148.59 | 131.54 | 2,872.46 | 9,534.46 | 37.72 | 6.23 |
| N-R-Gee | 20.20 | 36.03 | 42.34 | 6.89 | 94.88 | 77.00 | 50.29 | 152.24 | 134.25 | 2,883.41 | 9,066.60 | 39.54 | 5.79 |
| WL 319 HQ | 20.36 | 37.46 | 44.13 | 7.25 | 94.86 | 76.34 | 49.05 | 141.72 | 126.02 | 2,801.68 | 9,283.54 | 37.83 | 5.74 |
| Grand Mean | 20.73 | 35.80 | 42.21 | 6.95 | 94.78 | 77.22 | 49.78 | 151.64 | 135.15 | 2,875.30 | 9,565.57 | 38.83 | 6.04 |
| LSD (0.05) | 2.05 | 3.19 | 3.63 | 0.65 | 0.36 | 2.79 | 2.27 | 18.09 | 16.41 | 158.68 | 1,289.74 | 4.85 | 0.68 |
| C.V. (%) | 6.06 | 5.46 | 5.26 | 5.68 | 0.23 | 2.21 | 2.80 | 7.31 | 7.43 | 3.38 | 8.26 | 7.64 | 6.87 |
| R2 | 0.45 | 0.50 | 0.51 | 0.60 | 0.32 | 0.60 | 0.63 | 0.57 | 0.50 | 0.54 | 0.52 | 0.44 | 0.44 |

TABLE 17

Year 1 (35 days)—Cut 2

| Variety | CP | ADF | aNDF | Lignin | DM | IVTDMD | NDFD1 | RFQ | RFV | Milk/ton | Milk/acre | TTNDFD | Dyn Kd |
|---|---|---|---|---|---|---|---|---|---|---|---|---|---|
| CW 103009 | 19.31 | 37.95 | 44.38 | 7.91 | 94.68 | 72.99 | 45.63 | 131.66 | 124.62 | 2,677.20 | 6,358.20 | 33.86 | 5.55 |
| 55V12 | 16.49 | 37.50 | 44.75 | 8.20 | 94.71 | 72.09 | 42.14 | 127.51 | 124.26 | 2,802.92 | 6,497.29 | 27.46 | 4.52 |
| ROBUST | 18.46 | 39.99 | 46.74 | 8.51 | 94.82 | 70.65 | 43.65 | 119.92 | 115.67 | 2,583.29 | 5,965.16 | 32.47 | 5.33 |
| PGI 212, VR TOTAL | 18.89 | 38.57 | 44.86 | 7.97 | 94.72 | 72.64 | 45.73 | 129.74 | 122.09 | 2,656.21 | 6,394.54 | 33.46 | 5.59 |
| PGI 557, LELIA | 18.68 | 38.90 | 45.37 | 8.07 | 94.90 | 72.43 | 45.33 | 128.50 | 120.28 | 2,690.02 | 6,374.73 | 34.17 | 5.50 |
| Althea | 18.69 | 38.74 | 45.39 | 8.20 | 94.79 | 71.99 | 44.46 | 126.54 | 120.66 | 2,663.35 | 6,603.42 | 32.76 | 5.40 |
| Keystone II | 19.43 | 37.67 | 43.84 | 7.73 | 94.79 | 73.71 | 45.95 | 135.26 | 126.47 | 2,738.49 | 7,440.66 | 35.18 | 5.57 |
| PGI 529, DOMINATOR | 18.36 | 38.02 | 44.70 | 8.10 | 94.84 | 72.04 | 44.75 | 130.08 | 123.58 | 2,712.57 | 7,180.66 | 32.54 | 5.36 |
| PILLAR ST | 17.26 | 39.90 | 47.21 | 8.84 | 94.94 | 70.00 | 41.55 | 115.26 | 114.53 | 2,593.04 | 5,711.28 | 30.97 | 5.08 |
| StarGold | 19.28 | 36.37 | 42.58 | 7.59 | 94.67 | 74.32 | 46.19 | 141.73 | 132.58 | 2,809.64 | 7,323.04 | 33.01 | 5.24 |
| HybriForce-2400 | 19.28 | 36.70 | 43.32 | 7.93 | 94.75 | 73.96 | 44.87 | 135.48 | 129.58 | 2,759.50 | 6,089.64 | 34.34 | 5.58 |
| HybriForce-3400 | 18.97 | 37.63 | 43.86 | 7.84 | 95.05 | 73.12 | 46.32 | 137.48 | 126.66 | 2,790.49 | 6,258.27 | 34.98 | 5.40 |
| Magnum 7 | 18.70 | 40.11 | 46.51 | 8.46 | 94.79 | 70.64 | 44.61 | 120.77 | 115.39 | 2,552.70 | 6,598.79 | 33.12 | 5.57 |
| Magnum 7-Wet | 18.19 | 38.34 | 44.85 | 8.21 | 94.99 | 72.07 | 44.96 | 130.29 | 122.44 | 2,733.47 | 5,708.87 | 34.06 | 5.34 |
| N-R-Gee | 18.45 | 38.13 | 44.78 | 7.93 | 94.88 | 72.77 | 44.65 | 130.36 | 123.29 | 2,735.92 | 5,929.12 | 33.51 | 5.12 |
| WL 319 HQ | 18.53 | 38.24 | 44.54 | 7.83 | 94.67 | 73.46 | 45.48 | 133.18 | 123.56 | 2,771.05 | 5,962.84 | 30.63 | 4.87 |
| Grand Mean | 18.69 | 38.14 | 44.66 | 8.04 | 94.81 | 72.53 | 44.94 | 130.77 | 123.79 | 2,709.61 | 6,386.95 | 33.22 | 5.36 |
| LSD (0.05) | 1.28 | 3.70 | 3.97 | 0.83 | 0.24 | 3.10 | 2.38 | 20.10 | 16.57 | 246.79 | 1,108.61 | 2.99 | 0.43 |
| C.V. (%) | 4.20 | 5.95 | 5.44 | 6.32 | 0.15 | 2.62 | 3.24 | 9.41 | 8.20 | 5.58 | 10.63 | 5.52 | 4.92 |
| R2 | 0.56 | 0.28 | 0.30 | 0.37 | 0.53 | 0.38 | 0.53 | 0.33 | 0.30 | 0.30 | 0.46 | 0.56 | 0.60 |

TABLE 18

Year 1 (35 days)—3rd cut

| Variety | CP | ADF | aNDF | Lignin | DM | IVTDMD | NDFD1 | RFQ | RFV | Milk/ton | Milk/acre | TTNDFD | Dyn Kd |
|---|---|---|---|---|---|---|---|---|---|---|---|---|---|
| CW 103009 | 19.88 | 34.83 | 41.27 | 7.35 | 95.07 | 76.71 | 47.39 | 150.85 | 139.40 | 2,904.55 | 7,910.38 | 44.74 | 5.92 |
| 55V12 | 18.96 | 34.63 | 41.74 | 7.95 | 95.15 | 73.34 | 43.53 | 145.15 | 138.31 | 3,007.97 | 8,105.08 | 41.83 | 5.41 |
| ROBUST | 19.27 | 36.47 | 43.33 | 7.88 | 95.19 | 74.71 | 45.62 | 139.10 | 130.31 | 2,830.78 | 7,819.79 | 41.57 | 5.64 |
| PGI 212, VR TOTAL | 20.19 | 36.80 | 43.11 | 7.63 | 95.27 | 74.70 | 47.03 | 141.62 | 130.05 | 2,821.70 | 7,959.74 | 43.34 | 5.91 |
| PGI 557, LELIA | 19.59 | 36.89 | 43.56 | 7.89 | 95.20 | 73.74 | 46.25 | 138.91 | 128.71 | 2,820.15 | 8,226.08 | 43.29 | 5.76 |
| Althea | 18.32 | 37.54 | 44.39 | 8.04 | 95.12 | 74.19 | 44.99 | 131.76 | 125.03 | 2,735.74 | 7,720.23 | 40.86 | 5.72 |
| Keystone II | 20.52 | 33.89 | 40.13 | 7.01 | 95.22 | 77.34 | 47.65 | 157.12 | 144.91 | 2,969.61 | 9,134.64 | 45.04 | 6.04 |
| PGI 529, DOMINATOR | 18.74 | 34.26 | 41.25 | 7.73 | 95.15 | 75.54 | 45.64 | 149.50 | 140.37 | 2,973.83 | 8,145.79 | 41.44 | 5.51 |
| PILLAR ST | 18.61 | 35.51 | 42.95 | 8.30 | 95.23 | 72.57 | 41.95 | 134.87 | 132.79 | 2,885.51 | 7,968.57 | 39.89 | 5.42 |
| StarGold | 19.38 | 36.28 | 42.72 | 7.66 | 95.27 | 75.60 | 46.47 | 141.66 | 132.14 | 2,811.88 | 8,689.92 | 43.17 | 5.92 |
| HybriForce-2400 | 19.71 | 36.97 | 43.82 | 8.08 | 95.11 | 74.06 | 45.23 | 135.72 | 128.32 | 2,777.68 | 7,423.21 | 43.19 | 5.76 |
| HybriForce-3400 | 20.57 | 35.68 | 41.88 | 7.39 | 95.21 | 76.90 | 48.70 | 150.00 | 135.90 | 2,866.50 | 8,370.48 | 45.30 | 5.90 |
| Magnum 7 | 19.69 | 37.06 | 43.80 | 7.89 | 95.17 | 74.40 | 46.78 | 138.12 | 127.65 | 2,784.88 | 7,459.40 | 43.54 | 5.87 |
| Magnum 7-Wet | 20.22 | 37.64 | 44.32 | 8.09 | 95.21 | 74.26 | 46.72 | 135.10 | 125.16 | 2,733.07 | 7,484.13 | 44.19 | 6.01 |
| N-R-Gee | 19.29 | 34.55 | 41.24 | 7.43 | 95.21 | 76.49 | 46.64 | 151.35 | 140.80 | 2,939.39 | 7,472.57 | 42.94 | 5.46 |
| WL 319 HQ | 20.11 | 36.36 | 42.37 | 7.77 | 95.34 | 75.54 | 48.72 | 149.26 | 133.05 | 2,898.85 | 7,783.02 | 45.13 | 5.68 |
| Grand Mean | 19.74 | 35.82 | 42.39 | 7.70 | 95.16 | 75.36 | 46.50 | 144.34 | 134.27 | 2,858.53 | 7,861.90 | 43.47 | 5.81 |
| LSD (0.05) | 1.38 | 2.64 | 2.83 | 0.65 | 0.20 | 2.24 | 2.41 | 15.90 | 13.56 | 167.70 | 1,077.41 | 2.71 | 0.39 |
| C.V. (%) | 4.27 | 4.51 | 4.09 | 5.20 | 0.13 | 1.82 | 3.17 | 6.75 | 6.19 | 3.59 | 8.39 | 3.82 | 4.15 |
| R2 | 0.60 | 0.45 | 0.47 | 0.52 | 0.48 | 0.62 | 0.66 | 0.48 | 0.45 | 0.44 | 0.49 | 0.64 | 0.64 |

TABLE 19

Year 1—Weighted Mean (35 days)

| Variety | CP | ADF | aNDF | Lignin | DM | IVTDMD | NDFD1 | RFQ | RFV | Milk/ton | Milk/acre | TTNDFD | Dyn Kd |
|---|---|---|---|---|---|---|---|---|---|---|---|---|---|
| CW 103009 | 20.20 | 35.47 | 41.83 | 7.13 | 94.77 | 76.75 | 48.43 | 149.98 | 136.75 | 2,862.45 | 24,770.65 | 39.30 | 5.85 |
| 55V12 | 18.40 | 36.58 | 43.70 | 7.84 | 94.89 | 73.78 | 44.42 | 136.35 | 129.00 | 2,855.15 | 23,379.87 | 35.63 | 5.41 |
| ROBUST | 19.95 | 36.56 | 43.15 | 7.61 | 94.95 | 75.03 | 46.53 | 141.49 | 131.49 | 2,806.91 | 23,800.42 | 38.75 | 5.79 |
| PGI 212, VR TOTAL | 20.53 | 36.62 | 42.81 | 7.41 | 94.88 | 75.42 | 48.21 | 144.44 | 131.53 | 2,799.72 | 24,152.30 | 39.37 | 5.96 |
| PGI 557, LELIA | 19.43 | 37.53 | 44.05 | 7.64 | 94.91 | 74.49 | 47.28 | 138.46 | 126.28 | 2,785.40 | 24,186.46 | 37.87 | 5.63 |
| Althea | 19.41 | 37.09 | 43.67 | 7.72 | 94.89 | 74.52 | 46.38 | 138.27 | 128.71 | 2,771.37 | 23,400.43 | 37.48 | 5.73 |
| Keystone II | 20.21 | 35.79 | 42.03 | 7.14 | 95.01 | 76.35 | 48.41 | 149.97 | 135.96 | 2,875.69 | 26,113.63 | 40.24 | 5.82 |
| PGI 529, DOMINATOR | 18.88 | 36.27 | 43.04 | 7.63 | 94.96 | 74.62 | 46.43 | 141.90 | 131.44 | 2,851.37 | 24,777.20 | 37.38 | 5.59 |
| PILLAR ST | 18.41 | 38.54 | 45.80 | 8.34 | 94.92 | 71.82 | 43.76 | 125.82 | 120.65 | 2,701.87 | 22,626.27 | 34.96 | 5.36 |
| StarGold | 20.11 | 35.73 | 42.10 | 7.33 | 94.93 | 76.30 | 47.94 | 147.55 | 135.14 | 2,851.34 | 26,147.21 | 38.99 | 5.79 |
| HybriForce-2400 | 20.10 | 36.24 | 42.82 | 7.55 | 94.84 | 75.45 | 46.94 | 142.72 | 132.25 | 2,817.32 | 23,002.11 | 38.72 | 5.83 |
| HybriForce-3400 | 20.71 | 35.69 | 41.85 | 7.18 | 95.08 | 76.99 | 49.25 | 151.63 | 136.17 | 2,876.09 | 24,644.87 | 41.29 | 5.97 |
| Magnum 7 | 19.94 | 37.66 | 44.13 | 7.75 | 94.93 | 74.28 | 47.42 | 137.61 | 125.95 | 2,745.81 | 23,780.82 | 39.34 | 5.90 |
| Magnum 7-Wet | 19.86 | 37.27 | 43.88 | 7.72 | 95.00 | 74.54 | 47.50 | 139.32 | 127.03 | 2,789.45 | 22,727.45 | 38.97 | 5.93 |
| N-R-Gee | 19.39 | 36.19 | 42.72 | 7.36 | 94.98 | 75.64 | 47.54 | 145.55 | 133.00 | 2,857.61 | 22,468.30 | 38.94 | 5.49 |
| WL 319 HQ | 19.80 | 37.30 | 43.65 | 7.57 | 94.97 | 75.33 | 48.01 | 142.00 | 127.72 | 2,825.68 | 23,029.40 | 38.37 | 5.49 |
| Grand Mean | 19.84 | 36.46 | 42.95 | 7.50 | 94.91 | 75.30 | 47.36 | 143.42 | 131.68 | 2,823.63 | 23,814.42 | 38.77 | 5.77 |
| LSD (0.05) | 0.95 | 1.73 | 1.92 | 0.44 | 0.19 | 1.58 | 1.76 | 10.28 | 8.56 | 100.68 | 2,582.31 | 2.28 | 0.31 |
| C.V. (%) | 2.95 | 2.91 | 2.74 | 3.61 | 0.12 | 1.28 | 2.27 | 4.39 | 3.98 | 2.18 | 6.64 | 3.61 | 3.26 |
| R2 | 0.68 | 0.53 | 0.58 | 0.66 | 0.42 | 0.72 | 0.71 | 0.63 | 0.57 | 0.49 | 0.53 | 0.64 | 0.68 |

TABLE 20

Year 1 (28 days)—Cut 1

| Variety | CP | ADF | aNDF | Lignin | NDFD1 | DM | IVTDMD | RFQ | RFV | Milk/ton | Milk/acre | TTNDFD | Dyn Kd |
|---|---|---|---|---|---|---|---|---|---|---|---|---|---|
| CW 103009 | 27.76 | 21.29 | 26.59 | 3.62 | 60.23 | 94.72 | 89.95 | 286.71 | 252.96 | 3,635.53 | 14,457.03 | 69.13 | 8.87 |
| 55V12 | 25.76 | 23.54 | 29.09 | 4.08 | 58.97 | 94.78 | 87.49 | 259.48 | 225.66 | 3,559.77 | 13,614.06 | 58.62 | 8.08 |
| ROBUST | 27.70 | 21.79 | 26.88 | 3.76 | 60.02 | 94.84 | 89.22 | 283.52 | 249.30 | 3,622.98 | 12,445.85 | 68.08 | 8.45 |
| PGI 212, VR TOTAL | 27.43 | 22.43 | 27.61 | 3.99 | 58.98 | 94.78 | 88.72 | 271.91 | 240.83 | 3,561.33 | 11,965.29 | 69.16 | 8.79 |

TABLE 20-continued

Year 1 (28 days)—Cut 1

| Variety | CP | ADF | aNDF | Lignin | NDFD1 | DM | IVTDMD | RFQ | RFV | Milk/ton | Milk/acre | TTNDFD | Dyn Kd |
|---|---|---|---|---|---|---|---|---|---|---|---|---|---|
| PGI 557, LELIA | 26.84 | 23.01 | 28.23 | 4.07 | 58.90 | 94.88 | 88.25 | 266.88 | 234.11 | 3,568.84 | 13,175.76 | 63.50 | 8.00 |
| Althea | 27.17 | 23.65 | 28.97 | 4.32 | 58.45 | 94.81 | 87.51 | 257.20 | 226.32 | 3,507.25 | 13,118.58 | 65.32 | 8.70 |
| Keystone II | 27.76 | 22.75 | 27.95 | 3.95 | 59.02 | 94.73 | 88.52 | 269.04 | 237.07 | 3,559.43 | 12,609.97 | 66.81 | 8.75 |
| PGI 529, DOMINATOR | 26.94 | 23.77 | 29.13 | 4.28 | 57.87 | 94.67 | 87.38 | 254.84 | 224.86 | 3,504.71 | 12,769.97 | 61.44 | 8.38 |
| PILLAR ST | 27.24 | 23.58 | 28.73 | 4.17 | 59.95 | 94.97 | 87.74 | 263.55 | 228.54 | 3,541.25 | 14,345.91 | 66.92 | 8.20 |
| StarGold | 27.84 | 22.60 | 27.68 | 4.06 | 59.50 | 94.93 | 88.64 | 272.36 | 239.68 | 3,565.55 | 13,148.17 | 65.84 | 8.72 |
| HybriForce-2400 | 27.63 | 22.77 | 27.90 | 4.12 | 59.70 | 94.85 | 88.29 | 270.21 | 237.26 | 3,551.84 | 12,947.31 | 64.95 | 8.46 |
| HybriForce-3400 | 27.01 | 22.09 | 27.22 | 3.81 | 58.58 | 94.74 | 88.72 | 275.03 | 245.34 | 3,569.35 | 13,193.53 | 63.84 | 8.20 |
| Magnum 7 | 26.45 | 23.44 | 29.04 | 4.27 | 58.12 | 94.77 | 87.93 | 256.56 | 226.43 | 3,518.02 | 12,702.81 | 62.77 | 8.14 |
| Magnum 7-Wet | 26.97 | 22.39 | 27.47 | 3.83 | 60.05 | 94.93 | 88.68 | 277.96 | 241.96 | 3,627.90 | 14,227.37 | 66.99 | 7.75 |
| N-R-Gee | 27.53 | 22.52 | 27.61 | 3.97 | 58.26 | 94.68 | 88.21 | 269.01 | 240.45 | 3,530.51 | 11,912.11 | 61.00 | 8.80 |
| WL 319 HQ | 27.55 | 22.91 | 27.76 | 3.90 | 59.10 | 94.78 | 88.06 | 270.56 | 238.12 | 3,559.31 | 13,279.57 | 64.89 | 8.79 |
| Grand Mean | 27.29 | 22.67 | 27.88 | 4.00 | 59.14 | 94.79 | 88.44 | 270.29 | 238.06 | 3,566.28 | 13,085.60 | 65.25 | 8.52 |
| LSD (0.05) | 0.87 | 0.84 | 0.96 | 0.24 | 2.79 | 0.40 | 0.91 | 17.02 | 10.27 | 123.25 | 1,117.62 | 6.17 | 0.91 |
| C.V. (%) | 1.95 | 2.27 | 2.11 | 3.61 | 2.88 | 0.26 | 0.63 | 3.86 | 2.64 | 2.12 | 5.23 | 5.79 | 6.51 |
| R2 | 0.65 | 0.76 | 0.75 | 0.74 | 0.28 | 0.24 | 0.72 | 0.56 | 0.75 | 0.33 | 0.67 | 0.51 | 0.40 |

TABLE 21

Year 1 (28 days)—Cut 2

| Variety | CP | ADF | aNDF | Lignin | NDFD1 | DM | IVTDMD | RFQ | RFV | Milk/ton | Milk/acre | TTNDFD | Dyn Kd |
|---|---|---|---|---|---|---|---|---|---|---|---|---|---|
| CW 103009 | 21.91 | 33.65 | 39.64 | 6.87 | 48.43 | 94.76 | 77.43 | 158.81 | 147.30 | 2,907.38 | 6,308.02 | 40.37 | 5.99 |
| 55V12 | 19.29 | 36.33 | 42.86 | 7.63 | 47.13 | 95.05 | 74.73 | 143.33 | 131.59 | 2,849.63 | 6,686.72 | 37.87 | 5.43 |
| ROBUST | 21.38 | 34.54 | 40.49 | 7.26 | 47.32 | 94.86 | 76.25 | 152.54 | 142.45 | 2,876.16 | 6,521.73 | 39.19 | 5.78 |
| PGI 212, VR TOTAL | 21.71 | 35.41 | 41.46 | 7.42 | 46.67 | 94.75 | 75.52 | 145.93 | 137.64 | 2,803.24 | 6,065.85 | 37.76 | 5.95 |
| PGI 557, LELIA | 20.50 | 35.20 | 41.54 | 7.28 | 46.27 | 94.72 | 74.85 | 144.79 | 137.69 | 2,798.22 | 6,299.40 | 38.30 | 5.84 |
| Althea | 19.38 | 35.44 | 42.08 | 7.60 | 45.33 | 94.69 | 74.44 | 142.10 | 135.56 | 2,826.59 | 6,284.69 | 34.78 | 5.35 |
| Keystone II | 20.00 | 34.95 | 41.36 | 7.33 | 46.31 | 94.87 | 75.47 | 147.93 | 138.74 | 2,888.36 | 6,467.25 | 37.41 | 5.53 |
| PGI 529, DOMINATOR | 20.04 | 37.55 | 43.84 | 7.92 | 46.07 | 94.91 | 73.69 | 135.69 | 127.57 | 2,710.02 | 6,416.54 | 36.99 | 5.54 |
| PILLAR ST | 19.98 | 36.35 | 42.53 | 7.75 | 46.47 | 94.98 | 73.97 | 142.23 | 132.79 | 2,803.52 | 6,528.45 | 37.93 | 5.46 |
| StarGold | 21.31 | 33.04 | 38.88 | 6.95 | 47.91 | 94.71 | 77.21 | 163.09 | 151.98 | 2,964.93 | 6,183.77 | 38.40 | 5.67 |
| HybriForce-2400 | 20.96 | 35.29 | 41.28 | 7.37 | 46.72 | 94.75 | 74.93 | 146.51 | 138.43 | 2,799.47 | 6,288.96 | 38.20 | 5.83 |
| HybriForce-3400 | 21.08 | 35.09 | 41.36 | 7.46 | 46.02 | 94.80 | 75.23 | 146.01 | 138.53 | 2,834.14 | 6,436.34 | 38.43 | 5.84 |
| Magnum 7 | 20.73 | 36.24 | 42.78 | 7.84 | 46.13 | 94.74 | 74.38 | 138.89 | 131.96 | 2,740.88 | 5,899.37 | 37.59 | 5.83 |
| Magnum 7-Wet | 20.67 | 36.10 | 42.23 | 7.56 | 47.00 | 94.83 | 74.95 | 143.84 | 133.98 | 2,798.19 | 6,529.45 | 38.40 | 5.65 |
| N-R-Gee | 20.20 | 35.66 | 41.97 | 7.42 | 46.48 | 94.78 | 75.24 | 143.84 | 135.62 | 2,799.32 | 5,887.13 | 37.65 | 5.75 |
| WL 319 HQ | 20.45 | 36.01 | 42.09 | 7.37 | 47.77 | 94.88 | 75.02 | 146.15 | 134.72 | 2,810.57 | 6,092.94 | 39.31 | 5.81 |
| Grand Mean | 20.59 | 35.31 | 41.54 | 7.44 | 46.68 | 94.78 | 75.21 | 146.70 | 137.85 | 2,829.48 | 6,297.91 | 37.70 | 5.69 |
| LSD (0.05) | 1.33 | 2.47 | 2.65 | 0.53 | 1.83 | 0.26 | 2.22 | 15.26 | 13.18 | 167.31 | 710.28 | 2.85 | 0.45 |
| C.V. (%) | 3.94 | 4.28 | 3.91 | 4.36 | 2.41 | 0.17 | 1.81 | 6.37 | 5.85 | 3.62 | 6.91 | 4.63 | 4.88 |
| R2 | 0.59 | 0.45 | 0.47 | 0.49 | 0.41 | 0.44 | 0.47 | 0.45 | 0.47 | 0.41 | 0.31 | 0.43 | 0.50 |

TABLE 22

Year 1 (28 days)—3rd cut

| Variety | CP | ADF | aNDF | Lignin | NDFD1 | DM | IVTDMD | RFQ | RFV | Milk/ton | Milk/acre | TTNDFD | Dyn Kd |
|---|---|---|---|---|---|---|---|---|---|---|---|---|---|
| CW 103009 | 25.38 | 25.95 | 30.91 | 5.16 | 53.92 | 94.56 | 85.22 | 230.26 | 206.85 | 3,403.25 | 6,650.58 | 47.12 | 6.09 |
| 55V12 | 23.44 | 28.27 | 33.58 | 5.93 | 51.22 | 94.18 | 82.62 | 204.43 | 185.43 | 3,291.08 | 6,239.28 | 38.96 | 5.32 |
| ROBUST | 24.41 | 27.29 | 32.69 | 5.65 | 52.18 | 94.65 | 83.33 | 212.77 | 192.54 | 3,331.45 | 5,914.13 | 44.94 | 6.05 |
| PGI 212, VR TOTAL | 23.94 | 27.89 | 33.24 | 5.76 | 50.87 | 94.32 | 83.16 | 205.92 | 188.32 | 3,292.22 | 5,768.60 | 40.59 | 5.61 |
| PGI 557, LELIA | 24.64 | 27.77 | 33.01 | 5.73 | 52.10 | 94.77 | 83.05 | 210.17 | 189.68 | 3,314.56 | 6,147.00 | 46.30 | 6.30 |
| Althea | 23.39 | 27.76 | 33.22 | 5.85 | 51.66 | 94.61 | 83.08 | 207.93 | 188.47 | 3,309.70 | 6,600.63 | 42.54 | 5.58 |
| Keystone II | 23.92 | 27.67 | 33.10 | 5.68 | 51.28 | 94.35 | 83.36 | 207.08 | 189.38 | 3,285.97 | 6,700.33 | 41.61 | 5.76 |

TABLE 22-continued

Year 1 (28 days)—3rd cut

| Variety | CP | ADF | aNDF | Lignin | NDFD1 | DM | IVTDMD | RFQ | RFV | Milk/ton | Milk/acre | TTNDFD | Dyn Kd |
|---|---|---|---|---|---|---|---|---|---|---|---|---|---|
| PGI 529, DOMINATOR | 22.97 | 30.12 | 35.66 | 6.30 | 51.28 | 94.78 | 81.06 | 191.44 | 171.03 | 3,224.86 | 6,637.77 | 42.03 | 5.57 |
| PILLAR ST | 24.39 | 28.27 | 33.59 | 5.93 | 51.17 | 94.66 | 82.11 | 204.11 | 185.77 | 3,276.71 | 6,378.00 | 43.86 | 5.85 |
| StarGold | 23.85 | 28.92 | 34.33 | 6.03 | 51.44 | 94.77 | 82.29 | 199.32 | 179.83 | 3,256.01 | 6,294.91 | 43.99 | 5.92 |
| HybriForce-2400 | 24.69 | 26.62 | 31.96 | 5.57 | 51.80 | 94.54 | 83.68 | 217.28 | 198.45 | 3,350.76 | 5,509.05 | 44.48 | 5.97 |
| HybriForce-3400 | 24.75 | 26.97 | 32.24 | 5.50 | 51.30 | 94.47 | 83.81 | 213.77 | 196.07 | 3,325.00 | 5,522.22 | 43.97 | 5.99 |
| Magnum 7 | 25.06 | 26.65 | 31.85 | 5.51 | 52.51 | 94.54 | 84.35 | 219.67 | 199.28 | 3,355.42 | 5,837.77 | 45.13 | 6.10 |
| Magnum 7-Wet | 24.39 | 27.21 | 32.44 | 5.71 | 52.57 | 94.79 | 83.80 | 215.42 | 194.20 | 3,342.07 | 5,817.65 | 46.20 | 6.13 |
| N-R-Gee | 24.79 | 26.63 | 31.94 | 5.46 | 51.77 | 94.38 | 83.61 | 217.07 | 198.89 | 3,334.25 | 4,837.00 | 44.23 | 6.08 |
| WL 319 HQ | 24.71 | 27.45 | 32.59 | 5.60 | 50.92 | 94.18 | 83.42 | 210.26 | 192.97 | 3,305.92 | 5,277.01 | 40.81 | 5.79 |
| Grand Mean | 24.30 | 27.56 | 32.88 | 5.70 | 51.77 | 94.54 | 83.34 | 210.63 | 191.26 | 3,313.45 | 6,114.50 | 43.66 | 5.90 |
| LSD (0.05) | 1.11 | 1.61 | 1.81 | 0.42 | 1.62 | 0.33 | 1.71 | 15.74 | 13.83 | 83.54 | 533.85 | 4.16 | 0.48 |
| C.V. (%) | 2.80 | 3.57 | 3.38 | 4.52 | 1.92 | 0.22 | 1.25 | 4.58 | 4.43 | 1.54 | 5.35 | 5.84 | 5.03 |
| R2 | 0.58 | 0.61 | 0.61 | 0.62 | 0.47 | 0.53 | 0.55 | 0.58 | 0.61 | 0.53 | 0.81 | 0.48 | 0.49 |

TABLE 23

Year 1 (28 days)—4th cut

| Variety | CP | ADF | aNDF | Lignin | NDFD1 | DM | IVTDMD | RFQ | RFV | Milk/ton | Milk/acre | TTNDFD | Dyn Kd |
|---|---|---|---|---|---|---|---|---|---|---|---|---|---|
| CW 103009 | 24.32 | 26.81 | 32.05 | 5.56 | 54.33 | 94.93 | 83.71 | 223.57 | 197.40 | 3,407.01 | 6,074.39 | 51.09 | 6.01 |
| 55V12 | 22.43 | 28.59 | 34.30 | 6.12 | 52.49 | 95.02 | 81.81 | 204.85 | 180.80 | 3,351.06 | 5,476.49 | 47.15 | 5.73 |
| ROBUST | 23.86 | 27.63 | 32.98 | 5.88 | 52.72 | 95.00 | 82.73 | 212.39 | 190.06 | 3,341.09 | 5,725.08 | 49.87 | 6.18 |
| PGI 212, VR TOTAL | 24.30 | 26.51 | 31.62 | 5.65 | 53.44 | 95.04 | 83.38 | 225.62 | 200.87 | 3,430.43 | 5,857.22 | 49.98 | 6.10 |
| PGI 557, LELIA | 22.65 | 29.27 | 35.16 | 6.19 | 51.43 | 95.02 | 81.12 | 195.63 | 175.33 | 3,261.82 | 6,046.66 | 47.97 | 6.09 |
| Althea | 21.84 | 28.24 | 34.36 | 6.25 | 51.43 | 95.09 | 81.51 | 202.08 | 181.44 | 3,332.75 | 6,530.92 | 46.99 | 5.68 |
| Keystone II | 23.31 | 27.15 | 32.91 | 5.77 | 50.99 | 94.82 | 82.86 | 209.61 | 191.64 | 3,340.16 | 6,122.17 | 48.28 | 6.32 |
| PGI 529, DOMINATOR | 21.40 | 29.81 | 35.92 | 6.62 | 50.32 | 95.08 | 79.72 | 190.02 | 170.37 | 3,279.23 | 6,333.04 | 45.40 | 5.54 |
| PILLAR ST | 22.90 | 28.13 | 33.85 | 6.13 | 51.82 | 95.12 | 80.70 | 206.07 | 184.23 | 3,348.45 | 6,889.67 | 48.64 | 5.87 |
| StarGold | 23.27 | 29.23 | 34.91 | 6.26 | 51.59 | 95.08 | 81.22 | 197.26 | 176.22 | 3,276.89 | 6,695.55 | 48.73 | 6.16 |
| HybriForce-2400 | 23.87 | 27.77 | 33.28 | 5.92 | 52.14 | 95.02 | 82.33 | 209.30 | 188.08 | 3,334.54 | 5,735.56 | 51.22 | 6.08 |
| HybriForce-3400 | 24.03 | 27.55 | 33.05 | 5.89 | 51.91 | 94.92 | 82.41 | 210.60 | 189.87 | 3,345.29 | 5,748.81 | 50.95 | 6.26 |
| Magnum 7 | 23.43 | 27.89 | 33.48 | 5.91 | 52.20 | 94.85 | 82.56 | 208.82 | 187.45 | 3,329.25 | 5,403.88 | 48.80 | 6.01 |
| Magnum 7-Wet | 23.12 | 28.33 | 33.95 | 6.13 | 52.17 | 94.96 | 81.76 | 205.18 | 183.28 | 3,320.76 | 5,999.43 | 48.60 | 5.91 |
| N-R-Gee | 23.98 | 26.69 | 32.26 | 5.65 | 52.71 | 95.00 | 82.61 | 218.32 | 196.59 | 3,378.06 | 4,210.26 | 49.60 | 6.37 |
| WL 319 HQ | 24.01 | 28.45 | 33.89 | 6.02 | 52.68 | 95.07 | 81.70 | 206.27 | 183.35 | 3,313.69 | 5,501.05 | 50.74 | 6.20 |
| Grand Mean | 23.32 | 27.72 | 33.33 | 5.94 | 52.24 | 94.98 | 82.26 | 210.24 | 188.39 | 3,349.33 | 6,028.39 | 49.06 | 6.02 |
| LSD (0.05) | 1.21 | 1.63 | 1.82 | 0.40 | 2.05 | 0.21 | 1.84 | 15.88 | 13.71 | 103.46 | 886.97 | 3.38 | 0.46 |
| C.V. (%) | 3.19 | 3.60 | 3.33 | 4.10 | 2.41 | 0.13 | 1.37 | 4.63 | 4.46 | 1.89 | 9.01 | 4.22 | 4.72 |
| R2 | 0.66 | 0.65 | 0.68 | 0.68 | 0.46 | 0.40 | 0.58 | 0.68 | 0.68 | 0.62 | 0.68 | 0.51 | 0.48 |

TABLE 24

Year 1 (28 days)—5th cut

| Variety | CP | ADF | aNDF | Lignin | NDFD1 | DM | IVTDMD | RFQ | RFV | Milk/ton | Milk/acre | TTNDFD | Dyn Kd |
|---|---|---|---|---|---|---|---|---|---|---|---|---|---|
| CW 103009 | 27.74 | 24.31 | 28.66 | 5.18 | 55.68 | 94.76 | 85.36 | 252.55 | 227.49 | 3,454.92 | 4,206.30 | 53.90 | 7.28 |
| 55V12 | 25.25 | 25.80 | 31.29 | 5.74 | 53.56 | 95.01 | 84.90 | 225.33 | 204.55 | 3,362.47 | 3,914.48 | 51.45 | 6.94 |
| ROBUST | 26.71 | 24.30 | 29.26 | 5.29 | 53.64 | 94.71 | 84.68 | 242.69 | 222.57 | 3,432.88 | 4,230.35 | 51.31 | 7.42 |
| PGI 212, VR TOTAL | 27.52 | 24.75 | 29.55 | 5.27 | 53.86 | 94.79 | 85.27 | 239.80 | 219.16 | 3,407.15 | 4,075.57 | 53.93 | 7.78 |
| PGI 557, LELIA | 25.65 | 26.50 | 31.81 | 5.63 | 52.46 | 94.78 | 83.51 | 217.60 | 199.71 | 3,300.09 | 4,432.48 | 49.50 | 7.54 |
| Althea | 25.17 | 27.18 | 32.36 | 6.09 | 52.77 | 94.96 | 82.39 | 214.93 | 194.82 | 3,302.12 | 4,720.03 | 47.92 | 6.93 |
| Keystone II | 26.00 | 24.83 | 29.91 | 5.37 | 52.79 | 94.75 | 84.31 | 235.70 | 216.48 | 3,418.04 | 4,272.38 | 52.02 | 7.27 |
| PGI 529, DOMINATOR | 24.36 | 28.21 | 33.29 | 6.22 | 51.78 | 94.83 | 81.03 | 206.25 | 187.02 | 3,269.83 | 5,029.03 | 45.37 | 6.27 |
| PILLAR ST | 25.22 | 26.83 | 31.83 | 5.89 | 52.91 | 94.74 | 82.99 | 219.41 | 198.88 | 3,327.19 | 4,871.90 | 47.61 | 6.59 |
| StarGold | 25.32 | 27.29 | 32.37 | 5.83 | 52.83 | 94.80 | 82.20 | 215.82 | 194.43 | 3,328.09 | 5,436.54 | 47.74 | 6.60 |

TABLE 24-continued

Year 1 (28 days)—5th cut

| Variety | CP | ADF | aNDF | Lignin | NDFD1 | DM | IVTDMD | RFQ | RFV | Milk/ton | Milk/acre | TTNDFD | Dyn Kd |
|---|---|---|---|---|---|---|---|---|---|---|---|---|---|
| HybriForce-2400 | 26.56 | 24.88 | 29.83 | 5.41 | 53.65 | 94.76 | 84.20 | 237.77 | 216.82 | 3,417.01 | 4,639.29 | 50.96 | 6.97 |
| HybriForce-3400 | 26.65 | 25.27 | 30.29 | 5.50 | 52.42 | 94.39 | 83.92 | 229.35 | 212.59 | 3,345.55 | 4,479.36 | 48.90 | 7.21 |
| Magnum 7 | 26.81 | 24.41 | 29.18 | 5.35 | 54.93 | 94.84 | 84.89 | 246.57 | 222.79 | 3,454.13 | 4,240.05 | 54.54 | 6.94 |
| Magnum 7-Wet | 26.11 | 25.62 | 30.54 | 5.60 | 53.17 | 94.69 | 83.69 | 230.08 | 210.33 | 3,363.54 | 4,464.34 | 50.26 | 7.06 |
| N-R-Gee | 26.95 | 24.27 | 29.27 | 5.30 | 54.33 | 95.00 | 84.78 | 245.12 | 222.55 | 3,461.54 | 2,219.77 | 54.23 | 7.73 |
| WL 319 HQ | 27.09 | 25.20 | 30.01 | 5.32 | 54.92 | 94.99 | 86.44 | 238.10 | 214.82 | 3,395.83 | 3,906.97 | 56.46 | 7.64 |
| Grand Mean | 26.17 | 25.55 | 30.52 | 5.53 | 53.55 | 94.76 | 83.95 | 231.84 | 210.84 | 3,383.51 | 4,490.99 | 50.72 | 7.06 |
| LSD (0.05) | 0.94 | 1.10 | 1.32 | 0.32 | 2.08 | 0.35 | 1.29 | 15.63 | 11.80 | 97.54 | 618.88 | 4.75 | 0.63 |
| C.V. (%) | 2.21 | 2.64 | 2.65 | 3.51 | 2.38 | 0.23 | 0.94 | 4.13 | 3.43 | 1.77 | 8.44 | 5.73 | 5.42 |
| R2 | 0.76 | 0.80 | 0.77 | 0.77 | 0.49 | 0.51 | 0.77 | 0.70 | 0.77 | 0.59 | 0.84 | 0.59 | 0.65 |

TABLE 25

Year 1 (28 days)—Weighted Mean

| Variety | CP | ADF | aNDF | Lignin | NDFD1 | DM | IVTDMD | RFQ | RFV | Milk/ton | Milk/acre | TTNDFD | Dyn Kd |
|---|---|---|---|---|---|---|---|---|---|---|---|---|---|
| CW 103009 | 25.64 | 25.73 | 31.00 | 5.00 | 55.36 | 94.74 | 85.18 | 237.93 | 212.54 | 3,396.48 | 37,696.31 | 55.07 | 7.19 |
| 55V12 | 23.39 | 28.14 | 33.88 | 5.65 | 53.50 | 94.79 | 82.74 | 212.84 | 189.24 | 3,307.00 | 35,931.03 | 48.18 | 6.55 |
| ROBUST | 25.01 | 26.77 | 32.12 | 5.37 | 53.97 | 94.83 | 83.78 | 226.44 | 203.42 | 3,342.49 | 34,837.14 | 52.85 | 6.95 |
| PGI 212, VR TOTAL | 25.09 | 27.09 | 32.43 | 5.46 | 53.42 | 94.74 | 83.64 | 222.13 | 200.52 | 3,313.50 | 33,732.52 | 52.54 | 7.07 |
| PGI 557, LELIA | 24.33 | 27.78 | 33.36 | 5.55 | 53.13 | 94.84 | 82.86 | 214.39 | 192.82 | 3,284.80 | 36,101.30 | 51.11 | 6.89 |
| Althea | 23.81 | 27.91 | 33.63 | 5.79 | 52.75 | 94.82 | 82.50 | 211.19 | 190.25 | 3,283.23 | 37,254.84 | 49.98 | 6.76 |
| Keystone II | 24.51 | 27.16 | 32.72 | 5.44 | 52.90 | 94.70 | 83.44 | 218.72 | 197.94 | 3,316.95 | 36,172.11 | 51.28 | 6.96 |
| PGI 529, DOMINATOR | 23.55 | 29.33 | 35.00 | 6.03 | 52.22 | 94.83 | 81.33 | 201.88 | 181.23 | 3,222.77 | 37,186.36 | 48.16 | 6.54 |
| PILLAR ST | 24.34 | 28.05 | 33.51 | 5.71 | 53.59 | 94.92 | 82.30 | 214.53 | 191.30 | 3,293.99 | 39,013.92 | 51.89 | 6.67 |
| StarGold | 24.77 | 27.44 | 32.83 | 5.57 | 53.64 | 94.87 | 83.22 | 218.36 | 195.53 | 3,317.83 | 37,758.93 | 51.44 | 6.91 |
| HybriForce-2400 | 25.02 | 27.10 | 32.49 | 5.49 | 53.72 | 94.80 | 83.26 | 221.77 | 199.73 | 3,308.65 | 35,120.17 | 52.09 | 6.94 |
| HybriForce-3400 | 24.87 | 26.89 | 32.33 | 5.39 | 52.93 | 94.70 | 83.46 | 222.00 | 201.96 | 3,310.91 | 35,380.26 | 51.35 | 6.92 |
| Magnum 7 | 24.60 | 27.46 | 33.10 | 5.61 | 53.37 | 94.75 | 83.31 | 217.06 | 195.58 | 3,290.42 | 34,083.87 | 51.37 | 6.85 |
| Magnum 7-Wet | 24.52 | 27.37 | 32.77 | 5.49 | 54.02 | 94.86 | 83.32 | 222.37 | 198.48 | 3,326.78 | 37,038.25 | 52.76 | 6.68 |
| N-R-Gee | 24.79 | 27.04 | 32.52 | 5.37 | 53.33 | 94.73 | 83.32 | 221.88 | 201.21 | 3,298.70 | 29,066.27 | 50.60 | 7.20 |
| WL 319 HQ | 24.98 | 27.52 | 32.77 | 5.39 | 53.95 | 94.78 | 83.39 | 221.01 | 197.89 | 3,304.54 | 34,057.54 | 52.54 | 7.15 |
| Grand Mean | 24.60 | 27.29 | 32.77 | 5.50 | 53.50 | 94.78 | 83.30 | 220.06 | 197.91 | 3,313.35 | 36,017.40 | 51.45 | 6.90 |
| LSD (0.05) | 0.56 | 0.66 | 0.74 | 0.19 | 1.23 | 0.18 | 0.65 | 8.25 | 5.79 | 61.28 | 2,409.39 | 2.76 | 0.37 |
| C.V. (%) | 1.40 | 1.47 | 1.39 | 2.13 | 1.41 | 0.12 | 0.48 | 2.30 | 1.79 | 1.13 | 4.10 | 3.28 | 3.32 |
| R2 | 0.78 | 0.85 | 0.85 | 0.83 | 0.54 | 0.36 | 0.85 | 0.78 | 0.86 | 0.61 | 0.80 | 0.57 | 0.49 |

TABLE 26

Whole Plant Summary

| | Entry | CP | ADF | aNDF | Lignin | NDFD1 | DM | IVTDMD | RFQ | RFV | Milk/ton | TTNDFD | Dyn Kd |
|---|---|---|---|---|---|---|---|---|---|---|---|---|---|
| 28 DAC | CW 103009 | 23.91 | 28.33 | 34.04 | 5.62 | 49.32 | 94.31 | 81.92 | 197.63 | 182.82 | 3,271.58 | 41.90 | 6.46 |
| | 55V12 | 22.42 | 28.54 | 34.57 | 5.81 | 47.87 | 94.37 | 81.36 | 192.49 | 179.54 | 3,285.10 | 38.37 | 5.99 |
| | PGI 557 LELIA, | 22.95 | 30.29 | 36.12 | 6.16 | 47.25 | 94.56 | 80.00 | 179.84 | 168.28 | 3,177.20 | 39.30 | 6.19 |
| | WL 319 HQ | 23.32 | 28.15 | 33.67 | 5.63 | 49.05 | 94.43 | 82.58 | 200.58 | 185.48 | 3,304.74 | 41.66 | 6.43 |
| 35 DAC | CW 103009 | 24.45 | 27.27 | 33.15 | 5.70 | 47.92 | 94.60 | 82.06 | 200.36 | 190.36 | 3,277.13 | 43.42 | 7.37 |
| | 55V12 | 21.24 | 31.34 | 38.12 | 6.93 | 44.67 | 94.67 | 78.11 | 162.82 | 157.41 | 3,071.10 | 39.15 | 6.22 |
| | PGI 557, LELIA | 22.02 | 32.53 | 39.12 | 7.20 | 43.54 | 94.85 | 76.52 | 153.85 | 151.31 | 2,972.44 | 39.57 | 6.96 |
| | WL 319 HQ | 23.68 | 28.88 | 35.22 | 6.25 | 46.03 | 94.51 | 80.46 | 181.34 | 175.42 | 3,155.02 | 42.01 | 7.84 |
| 42 DAC | CW 103009 | 21.43 | 30.34 | 36.77 | 6.49 | 44.85 | 94.36 | 78.57 | 170.58 | 165.33 | 3,113.69 | 35.91 | 5.92 |
| | 55V12 | 18.47 | 33.31 | 40.50 | 7.53 | 41.61 | 94.60 | 74.38 | 146.87 | 146.15 | 2,985.11 | 32.86 | 5.01 |
| | PGI 557, LELIA | 21.20 | 32.08 | 38.54 | 6.83 | 43.01 | 94.07 | 77.34 | 156.06 | 154.90 | 2,980.46 | 32.46 | 5.96 |
| | WL 319 HQ | 21.14 | 30.35 | 36.83 | 6.57 | 43.86 | 94.08 | 77.99 | 168.65 | 164.84 | 3,125.72 | 32.52 | 5.74 |

TABLE 26-continued

Whole Plant Summary

|  | Entry | CP | ADF | aNDF | Lignin | NDFD1 | DM | IVTDMD | RFQ | RFV | Milk/ton | TTNDFD | Dyn Kd |
|---|---|---|---|---|---|---|---|---|---|---|---|---|---|
| AVERAGE | CW 103009 | 23.26 | 28.65 | 34.65 | 5.94 | 47.36 | 94.42 | 80.85 | 189.52 | 179.40 | 3,220.80 | 40.41 | 6.58 |
| OF 28, 35, | 55V12 | 20.71 | 31.06 | 37.73 | 6.76 | 44.72 | 94.55 | 77.95 | 167.39 | 161.03 | 3,113.77 | 36.79 | 5.74 |
| 42 DAC | PGI 557, LELIA, | 22.06 | 31.63 | 37.93 | 6.73 | 44.60 | 94.49 | 77.95 | 163.25 | 158.16 | 3,043.37 | 37.11 | 6.37 |
|  | WL 319 HQ | 22.72 | 29.13 | 35.24 | 6.15 | 46.31 | 94.34 | 80.34 | 183.52 | 175.25 | 3,195.16 | 38.73 | 6.67 |

Example 6

Forage Yield—CW099079

The total forage yield, as dry matter in tons per acre, and stand of CW099079 was determined over four years and compared to commercially available fall dormancy group 9 alfalfa varieties (Table 27). Stand refers to the final stand percentage and is a measure of persistence. Tests were conducted at Woodland, Calif. The forage quality was measured with 5, 6, or 7 cuts per year for a total of 24 cuts.

TABLE 27

| Variety | Year 1 5 cuts | Year 2 7 cuts | Year 3 6 cuts | Year 4 6 cuts | 4-Year TOTAL 24 cuts | Final Stand Year 4 |
|---|---|---|---|---|---|---|
| CW 099079 | 8.00 | 10.38 | 10.38 | 9.75 | 38.50 | 75.0 |
| Croplan 9 | 8.63 | 10.70 | 10.60 | 9.35 | 39.28 | 63.8 |
| CUF 101 | 7.73 | 9.13 | 8.43 | 7.85 | 33.13 | 43.8 |
| Magna 995 | 7.93 | 9.75 | 9.70 | 9.45 | 36.83 | 62.5 |
| Mecca III | 8.80 | 10.45 | 10.50 | 9.70 | 39.45 | 61.3 |

TABLE 27-continued

| Variety | Year 1 5 cuts | Year 2 7 cuts | Year 3 6 cuts | Year 4 6 cuts | 4-Year TOTAL 24 cuts | Final Stand Year 4 |
|---|---|---|---|---|---|---|
| 59N59 | 8.85 | 10.00 | 9.60 | 9.23 | 37.68 | 60.0 |
| PGI 908S | 8.80 | 10.73 | 10.28 | 9.78 | 39.58 | 66.3 |
| PGI 909 | 8.48 | 10.09 | 9.75 | 8.83 | 37.14 | 61.3 |
| SW 9720 | 8.70 | 9.68 | 9.70 | 8.75 | 36.83 | 57.5 |
| Trial Mean | 8.31 | 9.92 | 9.77 | 9.12 | 37.11 | 64.6 |
| LSD (.05) | 0.69 | 0.78 | 0.76 | 0.61 | 1.98 | 6.6 |
| CV % | 5.9% | 5.6% | 5.5% | 4.8% | 3.8% | 7.3% |

Example 7

Forage Quality—CW099079

The forage quality of CW099079 (weighted mean of 3 cuts harvested in Year 2) was compared to various commercially available fall dormancy group 9 alfalfa varieties using the methods described in Example 1. The forage quality of CW099079 and commercially available fall dormancy group 9 alfalfa varieties is shown in Table 28.

TABLE 28

| Variety | CP | ADF | aNDF | ADL | DM | IVTDMD | NDFD1 | Milk/Ton | Milk/Acre |
|---|---|---|---|---|---|---|---|---|---|
| CW 099079 | 24.70 | 26.73 | 32.02 | 4.96 | 89.89 | 83.18 | 47.73 | 3,276 | 33,980 |
| Croplan 9 | 23.67 | 28.72 | 34.36 | 5.34 | 89.97 | 81.56 | 46.59 | 3,155 | 33,750 |
| CUF 101 | 23.47 | 28.88 | 34.60 | 5.35 | 90.16 | 81.36 | 46.74 | 3,148 | 28,733 |
| Magna 995 | 24.65 | 27.35 | 32.78 | 5.15 | 89.68 | 82.47 | 46.99 | 3,230 | 31,484 |
| Mecca III | 23.52 | 28.56 | 34.09 | 5.40 | 90.13 | 81.43 | 46.50 | 3,167 | 33,060 |
| 59N59 | 24.60 | 27.66 | 33.23 | 5.15 | 89.67 | 82.44 | 47.19 | 3,213 | 32,138 |
| PGI 908S | 24.51 | 28.43 | 33.97 | 5.35 | 90.10 | 81.72 | 46.84 | 3,173 | 34,051 |
| PGI 909 | 23.69 | 29.17 | 34.82 | 5.53 | 89.82 | 81.06 | 45.93 | 3,123 | 31,502 |
| SW 9720 | 24.02 | 28.26 | 33.77 | 5.36 | 90.01 | 82.00 | 46.91 | 3,186 | 30,829 |
| Trial Mean | 24.43 | 27.77 | 33.28 | 5.15 | 89.97 | 82.31 | 47.23 | 3,212 | 31,846 |
| LSD (.05) | 0.78 | 1.12 | 1.26 | 0.28 | 0.34 | 0.97 | 0.96 | 66 | 2,422 |
| CV % | 2.3% | 2.9% | 2.7% | 3.9% | 0.3% | 0.8% | 1.5% | 1.5% | 5.4% |

The forage quality of CW099079 was compared to CW096043 and various commercially available fall dormancy groups 6-10 alfalfa varieties using the methods described in Example 1. CW099079, CW096043, and the commercially available alfalfa varieties were harvested in Year 3 at Stage 1 (21 DAC), Stage 2 (28 DAC), and Stage 3 (35 DAC). Tables 29-32.

TABLE 29

Fall Dormancy Groups

| Fall Dormancy Group | Variety |
|---|---|
| FD6 | CW 096043 |
| FD6 | P56S82 |

TABLE 29-continued

Fall Dormancy Groups

| Fall Dormancy Group | Variety |
|---|---|
| FD6 | PGI 608 |
| FD7 | HF 700 |
| FD7 | PGI 709 |
| FD8 | PGI 801 |
| FD8 | P58N57 |
| FD9 | CW 099079 |
| FD9 | PGI 909 |
| FD9 | Mecca III |
| FD10 | CW 1010 |
| FD10 | Fertilac 10 |

TABLE 30

Year 3 Stage 1 (21 DAC)—Average of 3 cuts

| Variety | CP | ADF | aNDF | ADL | DM | IVTDMD | NDFD1 | TTNDFD | Dyn Kd |
|---|---|---|---|---|---|---|---|---|---|
| CW 096043 | 25.20 | 26.26 | 31.29 | 5.13 | 91.63 | 85.01 | 49.50 | 36.57 | 8.26 |
| P56S82 | 24.56 | 26.82 | 32.19 | 5.27 | 91.72 | 84.26 | 49.22 | 33.65 | 8.87 |
| PGI 608 | 24.91 | 27.14 | 32.39 | 5.32 | 91.81 | 83.98 | 48.97 | 34.80 | 8.53 |
| HF 700 | 24.60 | 27.14 | 32.51 | 5.40 | 91.77 | 83.78 | 48.36 | 33.82 | 8.30 |
| PGI 709 | 24.16 | 28.54 | 33.92 | 5.63 | 91.85 | 83.01 | 48.30 | 33.34 | 8.24 |
| PGI 801 | 23.43 | 28.74 | 34.32 | 5.76 | 91.85 | 82.53 | 47.78 | 31.82 | 7.46 |
| P58N57 | 23.69 | 28.49 | 34.08 | 5.77 | 91.75 | 82.78 | 47.66 | 31.93 | 7.90 |
| CW 099079 | 23.61 | 27.74 | 33.15 | 5.45 | 91.68 | 83.71 | 48.60 | 33.19 | 7.64 |
| PGI 909 | 22.98 | 29.85 | 35.49 | 5.99 | 91.76 | 81.61 | 46.66 | 30.61 | 7.14 |
| Mecca III | 23.89 | 28.54 | 33.97 | 5.76 | 91.77 | 82.81 | 47.85 | 33.16 | 7.62 |
| CW 1010 | 23.17 | 29.42 | 35.06 | 5.91 | 91.82 | 82.13 | 47.20 | 31.67 | 7.34 |
| Fertilac 10 | 22.75 | 30.17 | 35.99 | 6.07 | 91.88 | 81.34 | 46.75 | 30.81 | 6.96 |
| Grand Mean | 23.93 | 28.15 | 33.59 | 5.60 | 91.76 | 83.18 | 48.13 | 33.02 | 7.85 |
| LSD (0.05) | 0.89 | 1.00 | 1.18 | 0.23 | 0.18 | 0.86 | 0.79 | 1.97 | 0.94 |
| C.V. (%) | 2.63 | 2.52 | 2.48 | 2.91 | 0.14 | 0.73 | 1.16 | 4.22 | 8.49 |
| R2 | 0.69 | 0.78 | 0.77 | 0.80 | 0.38 | 0.79 | 0.76 | 0.64 | 0.57 |

TABLE 31

Year 3 Stage 2 (28 DAC)—Average of 3 cuts

| Variety | CP | ADF | aNDF | ADL | DM | IVTDMD | NDFD1 | TTNDFD | Dyn Kd |
|---|---|---|---|---|---|---|---|---|---|
| CW 096043 | 22.23 | 30.09 | 35.63 | 6.06 | 90.97 | 81.22 | 45.94 | 28.88 | 6.70 |
| P56S82 | 21.51 | 31.20 | 37.24 | 6.41 | 90.94 | 79.75 | 44.86 | 26.11 | 6.30 |
| PGI 608 | 21.94 | 31.65 | 37.44 | 6.40 | 91.15 | 79.56 | 44.94 | 26.59 | 6.53 |
| HF 700 | 21.95 | 31.16 | 37.04 | 6.49 | 90.93 | 79.48 | 44.44 | 26.36 | 6.33 |
| PGI 709 | 21.75 | 32.06 | 37.99 | 6.57 | 91.09 | 79.12 | 44.69 | 26.43 | 6.44 |
| PGI 801 | 20.93 | 32.79 | 39.05 | 6.78 | 90.83 | 78.38 | 43.98 | 24.17 | 5.84 |
| P58N57 | 21.36 | 32.19 | 38.23 | 6.74 | 90.90 | 78.86 | 44.01 | 25.26 | 6.17 |
| CW 099079 | 21.34 | 31.38 | 37.27 | 6.45 | 90.72 | 79.76 | 44.78 | 25.96 | 6.13 |
| PGI 909 | 20.67 | 33.26 | 39.45 | 6.92 | 90.86 | 78.08 | 43.44 | 24.32 | 5.73 |
| Mecca III | 20.68 | 33.16 | 39.36 | 6.85 | 90.75 | 78.20 | 43.87 | 24.93 | 5.59 |
| CW 1010 | 20.83 | 33.01 | 39.22 | 6.94 | 90.79 | 78.09 | 43.44 | 23.98 | 5.66 |
| Fertilac 10 | 20.47 | 33.19 | 39.49 | 6.95 | 90.82 | 77.90 | 43.16 | 24.17 | 5.48 |
| Grand Mean | 21.35 | 31.97 | 37.96 | 6.60 | 90.87 | 79.20 | 44.41 | 25.73 | 6.11 |
| LSD (0.05) | 0.65 | 1.05 | 1.18 | 0.25 | 0.26 | 0.86 | 0.82 | 1.59 | 0.49 |
| C.V. (%) | 2.17 | 2.32 | 2.20 | 2.67 | 0.20 | 0.77 | 1.31 | 4.38 | 5.68 |
| R2 | 0.66 | 0.69 | 0.72 | 0.74 | 0.51 | 0.76 | 0.69 | 0.67 | 0.63 |

TABLE 32

Year 3 Stage 3 (35 DAC)—Average of 3 cuts

| Variety | CP | ADF | aNDF | ADL | DM | IVTDMD | NDFD1 | TTNDFD | Dyn Kd |
|---|---|---|---|---|---|---|---|---|---|
| CW 096043 | 20.39 | 33.27 | 39.49 | 6.83 | 90.96 | 78.23 | 43.43 | 27.11 | 6.42 |
| P56S82 | 19.30 | 35.02 | 41.74 | 7.35 | 91.11 | 76.02 | 41.81 | 24.19 | 5.64 |
| PGI 608 | 19.99 | 34.28 | 40.83 | 7.26 | 91.00 | 76.40 | 41.60 | 23.99 | 5.96 |
| HF 700 | 19.37 | 34.62 | 41.33 | 7.33 | 91.10 | 76.14 | 41.44 | 24.21 | 5.86 |
| PGI 709 | 19.94 | 34.21 | 40.75 | 7.24 | 90.91 | 76.80 | 42.30 | 23.88 | 5.86 |
| PGI 801 | 19.25 | 35.67 | 42.59 | 7.58 | 90.74 | 75.12 | 40.87 | 22.58 | 5.28 |
| P58N57 | 19.15 | 35.16 | 42.07 | 7.61 | 90.97 | 75.53 | 40.81 | 22.92 | 5.68 |
| CW 099079 | 19.60 | 33.84 | 40.32 | 7.12 | 90.90 | 77.05 | 41.89 | 24.90 | 5.83 |
| PGI 909 | 18.53 | 36.88 | 43.74 | 7.75 | 90.96 | 74.64 | 40.96 | 23.26 | 5.20 |
| Mecca III | 18.81 | 36.25 | 43.22 | 7.62 | 90.77 | 74.98 | 41.11 | 23.73 | 5.01 |
| CW 1010 | 18.85 | 35.79 | 42.66 | 7.75 | 90.99 | 75.32 | 40.92 | 23.02 | 5.41 |

TABLE 32-continued

Year 3 Stage 3 (35 DAC)—Average of 3 cuts

| Variety | CP | ADF | aNDF | ADL | DM | IVTDMD | NDFD1 | TTNDFD | Dyn Kd |
|---|---|---|---|---|---|---|---|---|---|
| Fertilac 10 | 18.92 | 35.59 | 42.57 | 7.52 | 90.50 | 75.19 | 40.60 | 21.94 | 4.73 |
| Grand Mean | 19.38 | 34.90 | 41.58 | 7.37 | 90.92 | 76.17 | 41.64 | 24.07 | 5.64 |
| LSD (0.05) | 0.60 | 1.07 | 1.24 | 0.26 | 0.59 | 1.11 | 0.94 | 1.94 | 0.63 |
| C.V. (%) | 2.20 | 2.16 | 2.10 | 2.53 | 0.46 | 1.03 | 1.59 | 5.71 | 7.96 |
| R2 | 0.70 | 0.72 | 0.74 | 0.75 | 0.40 | 0.70 | 0.68 | 0.68 | 0.57 |

CW099079, CW096043, and the commercially available alfalfa varieties were harvested in Year 4 at Stage 1 (21 DAC), Stage 2 (28 DAC), and Stage 3 (35 DAC) using the methods described in Example 1. See Tables 33-36.

TABLE 33

Fall Dormancy Groups

| Fall Dormancy Group | Variety |
|---|---|
| FD6 | CW 096043 |
| FD6 | P56S82 |
| FD6 | PGI 608 |
| FD6 | WL440 |

TABLE 33-continued

Fall Dormancy Groups

| Fall Dormancy Group | Variety |
|---|---|
| FD7 | HF 700 |
| FD7 | PGI 709 |
| FD7 | SW7410 |
| FD9 | CW 099079 |
| FD9 | PGI 909 |
| FD9 | Mecca III |
| FD10 | CW 1010 |
| FD10 | Fertilac 10 |
| FD10 | Sedona |

TABLE 34

Year 4 Stage 1 (21 DAC)—Average of 3 cuts

| Variety | CP | ADF | aNDF | ADL | DM | IVTDMD | NDFD1 | TTNDFD | Dyn Kd |
|---|---|---|---|---|---|---|---|---|---|
| CW 096043 | 24.13 | 28.20 | 33.84 | 5.64 | 92.39 | 81.69 | 48.38 | 28.68 | 7.51 |
| P56S82 | 23.93 | 28.45 | 34.33 | 5.78 | 92.43 | 80.93 | 47.98 | 27.05 | 7.43 |
| PGI 608 | 24.19 | 28.49 | 34.29 | 5.70 | 92.36 | 81.14 | 47.80 | 27.73 | 7.44 |
| WL440 | 23.91 | 28.55 | 34.30 | 5.74 | 92.47 | 81.10 | 47.83 | 27.20 | 7.45 |
| HF 700 | 23.75 | 28.26 | 34.17 | 5.76 | 92.29 | 80.99 | 47.39 | 26.30 | 7.19 |
| PGI 709 | 23.82 | 28.82 | 34.70 | 5.85 | 92.45 | 81.18 | 47.57 | 27.90 | 7.40 |
| SW7410 | 23.40 | 29.07 | 34.96 | 5.91 | 92.43 | 80.85 | 47.10 | 27.54 | 6.88 |
| CW 099079 | 23.63 | 29.21 | 35.11 | 5.88 | 92.47 | 80.68 | 47.60 | 27.05 | 7.35 |
| PGI 909 | 22.97 | 30.27 | 36.20 | 6.21 | 92.52 | 79.35 | 46.68 | 25.88 | 6.70 |
| Mecca III | 23.73 | 28.81 | 34.71 | 5.88 | 92.44 | 81.05 | 47.57 | 27.61 | 7.23 |
| CW 1010 | 23.09 | 30.16 | 36.23 | 6.12 | 92.54 | 79.68 | 46.84 | 26.26 | 7.04 |
| Fertilac 10 | 23.15 | 30.14 | 36.07 | 6.09 | 92.47 | 79.90 | 46.79 | 25.83 | 6.60 |
| Sedona | 22.93 | 29.77 | 35.79 | 6.10 | 92.37 | 79.80 | 46.81 | 25.65 | 6.50 |
| Grand Mean | 23.58 | 29.09 | 34.98 | 5.90 | 92.43 | 80.65 | 47.41 | 26.95 | 7.12 |
| LSD (0.05) | 0.86 | 1.38 | 1.54 | 0.31 | 0.15 | 1.13 | 0.82 | 1.55 | 0.76 |
| C.V. (%) | 2.59 | 3.37 | 3.11 | 3.68 | 0.12 | 0.99 | 1.23 | 4.06 | 7.55 |
| R2 | 0.56 | 0.48 | 0.49 | 0.53 | 0.52 | 0.54 | 0.58 | 0.60 | 0.45 |

TABLE 35

Year 4 Stage 21 (28 DAC)—Average of 3 cuts

| Variety | CP | ADF | aNDF | ADL | DM | IVTDMD | NDFD1 | TTNDFD | Dyn Kd |
|---|---|---|---|---|---|---|---|---|---|
| CW 096043 | 21.56 | 29.95 | 36.03 | 6.24 | 92.79 | 80.40 | 46.03 | 28.64 | 6.72 |
| P56S82 | 21.26 | 31.19 | 37.44 | 6.53 | 92.84 | 79.12 | 45.47 | 27.17 | 6.65 |
| PGI 608 | 21.39 | 31.79 | 38.05 | 6.70 | 92.85 | 78.17 | 44.86 | 26.77 | 6.67 |
| WL440 | 20.50 | 32.97 | 39.32 | 6.89 | 92.83 | 77.75 | 44.54 | 25.94 | 6.02 |
| HF 700 | 21.33 | 31.21 | 37.45 | 6.68 | 92.79 | 78.39 | 44.70 | 26.82 | 6.53 |
| PGI 709 | 20.80 | 32.10 | 38.48 | 6.72 | 92.82 | 78.26 | 44.91 | 26.75 | 6.22 |
| SW7410 | 20.98 | 31.73 | 37.96 | 6.80 | 92.86 | 78.02 | 44.57 | 27.26 | 6.27 |
| CW 099079 | 20.91 | 31.32 | 37.45 | 6.54 | 92.76 | 79.45 | 45.53 | 27.32 | 6.25 |
| PGI 909 | 19.64 | 33.86 | 40.39 | 7.17 | 92.90 | 76.90 | 43.38 | 25.04 | 5.79 |
| Mecca III | 20.17 | 33.03 | 39.50 | 6.97 | 92.85 | 77.24 | 44.16 | 26.05 | 5.77 |
| CW 1010 | 20.01 | 32.98 | 39.37 | 7.01 | 92.90 | 77.49 | 43.85 | 25.29 | 5.76 |
| Fertilac 10 | 19.63 | 33.90 | 40.40 | 7.27 | 92.84 | 75.92 | 42.67 | 24.37 | 5.61 |
| Sedona | 20.08 | 33.18 | 39.62 | 7.08 | 92.85 | 76.93 | 43.99 | 25.35 | 5.72 |
| Grand Mean | 20.70 | 32.10 | 38.42 | 6.77 | 92.82 | 78.20 | 44.65 | 26.54 | 6.18 |
| LSD (0.05) | 0.62 | 0.95 | 1.06 | 0.25 | 0.12 | 0.91 | 0.88 | 0.99 | 0.44 |
| C.V. (%) | 2.13 | 2.09 | 1.95 | 2.64 | 0.09 | 0.83 | 1.39 | 2.64 | 5.07 |
| R2 | 0.78 | 0.80 | 0.80 | 0.79 | 0.60 | 0.83 | 0.77 | 0.88 | 0.72 |

TABLE 36

Year 4 Stage 3 (35 DAC)—Average of 3 cuts

| Variety | CP | ADF | aNDF | ADL | DM | IVTDMD | NDFD1 | TTNDFD | Dyn Kd |
|---|---|---|---|---|---|---|---|---|---|
| CW 096043 | 19.62 | 33.09 | 39.52 | 6.93 | 93.01 | 77.38 | 43.08 | 25.15 | 6.37 |
| P56S82 | 19.09 | 34.84 | 41.63 | 7.39 | 93.21 | 75.44 | 42.13 | 23.81 | 6.10 |
| PGI 608 | 19.74 | 34.55 | 41.11 | 7.40 | 93.06 | 75.28 | 42.00 | 23.89 | 6.09 |
| WL440 | 18.97 | 35.58 | 42.38 | 7.45 | 93.16 | 74.93 | 42.24 | 23.42 | 5.72 |
| HF 700 | 19.03 | 34.55 | 41.25 | 7.37 | 93.17 | 75.28 | 42.08 | 23.77 | 5.82 |
| PGI 709 | 18.31 | 36.03 | 42.88 | 7.75 | 93.18 | 74.51 | 41.51 | 23.21 | 5.53 |
| SW7410 | 18.59 | 35.10 | 41.95 | 7.72 | 93.09 | 74.78 | 40.64 | 23.91 | 5.62 |
| CW 099079 | 18.52 | 34.47 | 41.08 | 7.28 | 92.98 | 76.08 | 42.14 | 23.97 | 5.56 |
| PGI 909 | 17.66 | 37.25 | 44.27 | 8.08 | 93.13 | 73.08 | 39.84 | 22.21 | 5.30 |
| Mecca III | 18.12 | 36.02 | 42.89 | 7.71 | 93.13 | 74.42 | 41.25 | 23.26 | 5.15 |
| CW 1010 | 18.30 | 35.68 | 42.52 | 7.67 | 93.09 | 74.61 | 41.24 | 22.94 | 5.43 |
| Fertilac 10 | 17.55 | 37.19 | 44.12 | 8.12 | 93.24 | 72.80 | 39.57 | 21.63 | 5.12 |
| Sedona | 17.70 | 36.74 | 43.69 | 7.95 | 93.04 | 73.39 | 40.49 | 22.17 | 5.06 |
| Grand Mean | 18.57 | 35.36 | 42.14 | 7.56 | 93.11 | 74.96 | 41.55 | 23.47 | 5.63 |
| LSD (0.05) | 0.61 | 1.22 | 1.35 | 0.33 | 0.19 | 1.14 | 1.11 | 1.14 | 0.40 |
| C.V. (%) | 2.31 | 2.43 | 2.27 | 3.06 | 0.14 | 1.08 | 1.89 | 3.42 | 4.97 |
| R2 | 0.79 | 0.71 | 0.72 | 0.74 | 0.48 | 0.76 | 0.70 | 0.69 | 0.74 |

Figure 6:
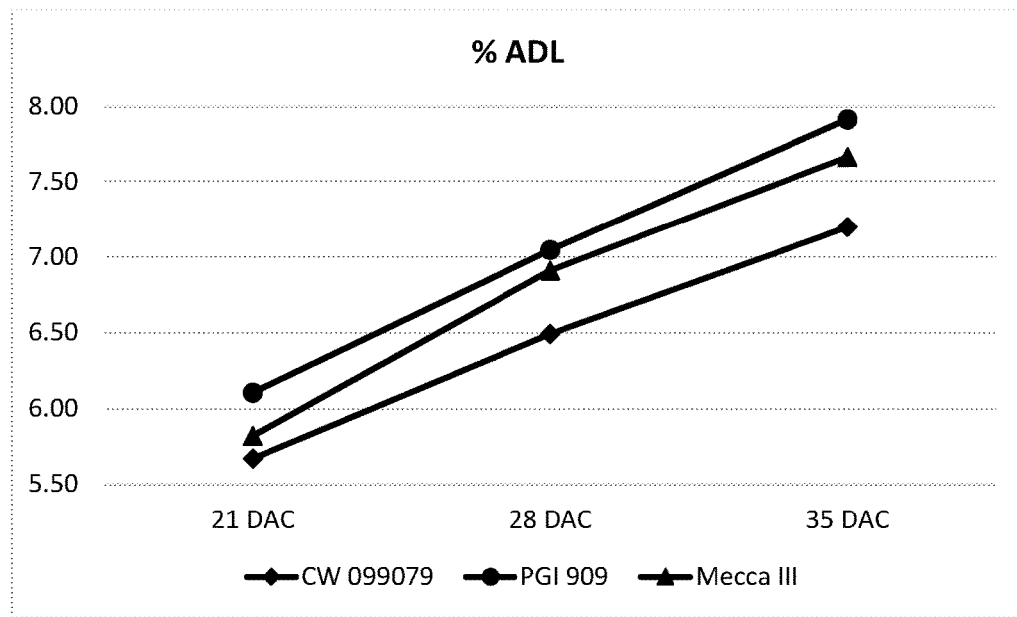
FIG. 6 shows the lignin content ("% ADL") after 21, 28, or 35 DAC of CW099079 compared to commercial varieties harvested in Year 3 and 4.

Table 37 and FIG. 6 summarize the lignin content measured as ADL from Tables 34-36. CW 099079 had 9.0% less ADL compared to PGI 909 in the 35 DAC sample.

TABLE 37

AVERAGE OF 6 CUTS

| Fall Dormancy | | % ADL | | |
|---|---|---|---|---|
| Group | Variety | 21 DAC | 28 DAC | 35 DAC |
| FD9 | CW 099079 | 5.67 | 6.49 | 7.20 |
| FD9 | PGI 909 | 6.10 | 7.05 | 7.91 |
| FD9 | Mecca III | 5.82 | 6.91 | 7.66 |

TABLE 38

| Variety | Year 1 5 cuts | Year 2 7 cuts | Year 3 6 cuts | Year 4 6 cuts | 4-Year TOTAL 24 cuts | Final Stand Year 4 |
|---|---|---|---|---|---|---|
| CW 090075 | 8.05 | 10.18 | 10.08 | 9.58 | 37.88 | 71.3 |
| CW 1010 | 8.35 | 9.94 | 10.05 | 9.05 | 37.39 | 63.8 |
| Fertilac 10 | 8.10 | 9.45 | 9.25 | 8.63 | 35.43 | 53.8 |
| PGI 1007 BA | 7.95 | 9.88 | 9.60 | 9.13 | 36.55 | 63.8 |
| Sedona | 8.65 | 9.63 | 9.35 | 9.00 | 36.63 | 57.5 |
| SW10 | 8.55 | 9.28 | 9.43 | 8.50 | 35.75 | 57.5 |
| Trial Mean | 8.31 | 9.92 | 9.77 | 9.12 | 37.11 | 64.6 |
| LSD (.05) | 0.69 | 0.78 | 0.76 | 0.61 | 1.98 | 6.6 |
| CV % | 5.9% | 5.6% | 5.5% | 4.8% | 3.8% | 7.3% |

Example 8

Forage Yield—CW090075

The total forage yield, as dry matter in tons per acre, and stand of CW090075 was determined over four years and compared to commercially available fall dormancy group 10 alfalfa varieties (Table 38). Stand refers to the final stand percentage and is a measure of persistence. Tests were conducted at Woodland, Calif. The forage quality was measured with 5, 6, or 7 cuts per year for a total of 24 cuts.

Example 9

Forage Quality—CW090075

The forage quality of CW090075 (weighted mean of 3 cuts harvested in Year 2) was compared to various commercially available fall dormancy group 10 alfalfa varieties using the methods described in Example 1. The forage quality of CW090075 and the commercially available fall dormancy group 10 alfalfa varieties are shown in Table 39.

TABLE 39

| Variety | CP | ADF | aNDF | ADL | DM | IVTDMD | NDFD1 | Milk/ Ton | Milk/ Acre |
|---|---|---|---|---|---|---|---|---|---|
| CW 090075 | 25.30 | 26.68 | 31.89 | 4.93 | 90.00 | 83.64 | 48.31 | 3,289 | 33,460 |
| CW 1010 | 23.96 | 28.54 | 34.18 | 5.36 | 90.01 | 81.64 | 46.54 | 3,161 | 31,403 |
| Fertilac 10 | 23.41 | 29.32 | 35.00 | 5.57 | 90.11 | 81.03 | 45.99 | 3,116 | 29,436 |
| PGI 1007 BA | 24.09 | 28.52 | 33.91 | 5.33 | 89.98 | 81.88 | 47.06 | 3,182 | 31,427 |
| Sedona | 24.37 | 28.03 | 33.40 | 5.21 | 90.00 | 82.13 | 46.99 | 3,203 | 30,827 |
| SW10 | 23.81 | 28.53 | 34.02 | 5.28 | 89.86 | 81.87 | 46.83 | 3,174 | 29,433 |
| Trial Mean | 24.43 | 27.77 | 33.28 | 5.15 | 89.97 | 82.31 | 47.23 | 3,212 | 31,846 |
| LSD (.05) | 0.78 | 1.12 | 1.26 | 0.28 | 0.34 | 0.97 | 0.96 | 66 | 2,422 |
| CV % | 2.3% | 2.9% | 2.7% | 3.9% | 0.3% | 0.8% | 1.5% | 1.5% | 5.4% |

The forage quality of CW090075 was compared to CW096043, CW099079, and various commercially available fall dormancy groups 6, 9, and 10 alfalfa varieties using the methods described in Example 1. CW090075, CW096043, CW099079, and the commercially available alfalfa varieties were harvested in Year 0 at Stage 1 (21 DAC), Stage 2 (28 DAC), and Stage 3 (35 DAC). Tables 40-43.

TABLE 40

Fall Dormancy Groups

| Fall Dormancy Group | Variety |
|---|---|
| FD6 | P.56S82 |
| FD6 | HybriForce 2600 |
| FD6 | PGI 608 |
| FD6 | CW 096043 |
| FD9 | P59N59 |
| FD9 | DS 598 |
| FD9 | CUF 101 |
| FD9 | CW 099079 |
| FD10 | CW 1010 |
| FD10 | Super 10 |
| FD10 | DS 1020 |
| FD10 | CW 090075 |

TABLE 41

Year 1 Stage 1 (21 DAC)—Average of 2 cuts

| Variety | CP | ADF | aNDF | ADL | DM | IVTDMD | NDFD1 | TTNDFD | Dyn Kd |
|---|---|---|---|---|---|---|---|---|---|
| P.56S82 | 26.55 | 24.65 | 29.82 | 4.74 | 93.61 | 84.57 | 51.00 | 32.38 | 7.58 |
| HybriForce 2600 | 26.69 | 25.60 | 30.75 | 4.95 | 93.48 | 83.83 | 50.42 | 33.96 | 13.41 |
| PGI 608 | 26.99 | 25.56 | 30.66 | 4.86 | 93.61 | 84.18 | 51.07 | 33.41 | 10.79 |
| CW 096043 | 25.73 | 25.51 | 31.00 | 4.90 | 93.60 | 84.25 | 50.81 | 30.28 | 9.90 |
| P59N59 | 25.22 | 27.87 | 33.38 | 5.52 | 93.57 | 82.15 | 48.86 | 29.84 | 9.98 |
| DS 598 | 24.03 | 29.04 | 34.80 | 5.72 | 93.63 | 81.30 | 48.34 | 28.43 | 8.08 |
| CUF 101 | 25.94 | 26.83 | 32.09 | 5.16 | 93.61 | 83.15 | 49.95 | 32.34 | 9.87 |
| CW 099079 | 25.76 | 24.67 | 30.01 | 4.82 | 93.65 | 84.81 | 50.04 | 32.66 | 8.82 |
| CW 1010 | 24.85 | 27.88 | 33.31 | 5.52 | 93.63 | 82.00 | 48.60 | 30.44 | 8.21 |
| Super 10 | 23.61 | 29.65 | 35.32 | 5.81 | 93.59 | 80.99 | 48.61 | 27.88 | 6.75 |
| DS 1020 | 24.22 | 28.71 | 34.19 | 5.68 | 93.66 | 81.59 | 48.80 | 29.26 | 7.02 |
| CW 090075 | 23.94 | 28.15 | 33.74 | 5.54 | 93.62 | 81.93 | 48.45 | 27.78 | 7.33 |
| Test Average | 25.34 | 26.73 | 32.14 | 5.21 | 93.59 | 83.05 | 49.57 | 30.66 | 8.83 |
| LSD (0.05) | 1.74 | 2.59 | 2.85 | 0.53 | 0.19 | 1.91 | 1.57 | 2.90 | 3.92 |
| C.V. (%) | 4.2% | 5.9% | 5.4% | 6.2% | 0.1% | 1.4% | 1.9% | 5.8% | 27.1% |

TABLE 42

Year 1 Stage 2 (28 DAC)—Average of 2 cuts

| Variety | CP | ADF | aNDF | ADL | DM | IVTDMD | NDFD1 | TTNDFD | Dyn Kd |
|---|---|---|---|---|---|---|---|---|---|
| P.56S82 | 22.18 | 31.17 | 37.68 | 6.42 | 93.45 | 78.59 | 46.54 | 24.97 | 7.63 |
| HybriForce 2600 | 23.65 | 29.48 | 35.36 | 5.81 | 93.50 | 81.09 | 48.03 | 30.83 | 8.51 |
| PGI 608 | 22.10 | 33.05 | 39.41 | 6.53 | 93.43 | 77.65 | 46.28 | 24.62 | 6.72 |
| CW 096043 | 24.29 | 26.85 | 32.93 | 5.28 | 93.40 | 82.55 | 48.40 | 28.31 | 7.55 |
| P59N59 | 21.63 | 32.80 | 39.31 | 6.62 | 93.47 | 78.07 | 45.29 | 25.18 | 7.52 |
| DS 598 | 21.58 | 31.42 | 37.95 | 6.30 | 93.48 | 78.80 | 46.21 | 25.95 | 6.89 |
| CUF 101 | 21.84 | 32.13 | 38.66 | 6.46 | 93.42 | 78.23 | 46.18 | 25.35 | 6.40 |
| CW 099079 | 21.94 | 30.52 | 36.84 | 6.16 | 93.53 | 79.73 | 46.49 | 27.20 | 6.63 |
| CW 1010 | 21.05 | 33.64 | 40.23 | 6.87 | 93.41 | 76.96 | 44.91 | 24.48 | 6.17 |
| Super 10 | 22.00 | 32.05 | 38.49 | 6.48 | 93.45 | 78.14 | 46.14 | 25.92 | 6.65 |
| DS 1020 | 20.38 | 34.53 | 41.30 | 7.08 | 93.46 | 76.20 | 44.65 | 23.47 | 5.59 |
| CW 090075 | 22.75 | 29.99 | 36.17 | 6.01 | 93.49 | 80.45 | 46.88 | 28.18 | 7.37 |
| Test Average | 22.22 | 31.18 | 37.53 | 6.26 | 93.47 | 79.08 | 46.38 | 26.45 | 7.11 |
| LSD (0.05) | 1.99 | 3.33 | 3.81 | 0.75 | 0.19 | 2.86 | 1.73 | 3.83 | 2.94 |
| C.V. (%) | 5.5% | 6.5% | 6.2% | 7.3% | 0.1% | 2.2% | 2.3% | 8.8% | 25.3% |

TABLE 43

Year 1 Stage 3 (35 DAC)—Average of 2 cuts

| Variety | CP | ADF | aNDF | ADL | DM | IVTDMD | NDFD1 | TTNDFD | Dyn Kd |
|---|---|---|---|---|---|---|---|---|---|
| P.56S82 | 21.24 | 32.29 | 39.09 | 6.63 | 93.29 | 77.61 | 43.40 | 22.45 | 7.74 |
| HybriForce 2600 | 21.17 | 32.90 | 39.66 | 6.64 | 93.22 | 77.40 | 44.68 | 23.33 | 6.93 |
| PGI 608 | 21.58 | 32.53 | 39.14 | 6.55 | 93.25 | 77.53 | 44.39 | 22.91 | 7.54 |

TABLE 43-continued

Year 1 Stage 3 (35 DAC)—Average of 2 cuts

| Variety | CP | ADF | aNDF | ADL | DM | IVTDMD | NDFD1 | TTNDFD | Dyn Kd |
|---|---|---|---|---|---|---|---|---|---|
| CW 096043 | 22.69 | 28.97 | 35.71 | 5.79 | 93.06 | 80.07 | 45.23 | 23.94 | 6.66 |
| P59N59 | 20.74 | 33.19 | 40.09 | 6.90 | 93.19 | 76.72 | 43.02 | 21.32 | 6.10 |
| DS 598 | 20.34 | 34.00 | 40.94 | 6.97 | 93.36 | 76.17 | 43.11 | 22.76 | 6.17 |
| CUF 101 | 21.04 | 32.67 | 39.47 | 6.67 | 93.32 | 76.98 | 43.45 | 22.98 | 6.62 |
| CW 099079 | 21.87 | 31.01 | 37.62 | 6.42 | 93.32 | 78.18 | 43.96 | 23.92 | 7.35 |
| CW 1010 | 20.76 | 34.13 | 40.97 | 7.12 | 93.32 | 75.84 | 42.42 | 22.30 | 5.98 |
| Super 10 | 21.29 | 33.27 | 40.01 | 6.89 | 93.37 | 76.93 | 43.51 | 23.89 | 6.47 |
| DS 1020 | 20.50 | 34.58 | 41.43 | 7.18 | 93.46 | 75.62 | 43.06 | 23.53 | 5.81 |
| CW 090075 | 21.83 | 31.97 | 38.59 | 6.57 | 93.35 | 77.95 | 44.21 | 25.30 | 7.02 |
| Test Average | 21.30 | 32.47 | 39.23 | 6.66 | 93.26 | 77.29 | 43.71 | 22.91 | 6.66 |
| LSD (0.05) | 0.89 | 1.70 | 1.86 | 0.43 | 0.21 | 1.62 | 1.19 | 2.48 | 2.10 |
| C.V. (%) | 2.6% | 3.2% | 2.9% | 4.0% | 0.1% | 1.3% | 1.7% | 6.6% | 19.2% |

Figure 7:
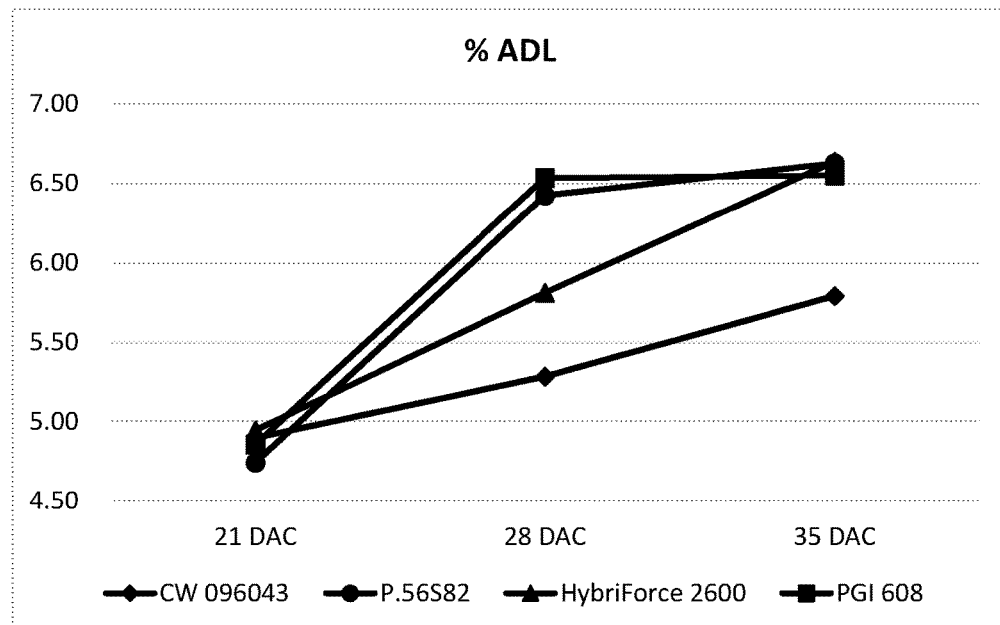
FIG. 7 shows the lignin content ("% ADL") after 21, 28, or 35 DAC of CW096043 compared to commercial varieties harvested in Year 1.
Figure 8:
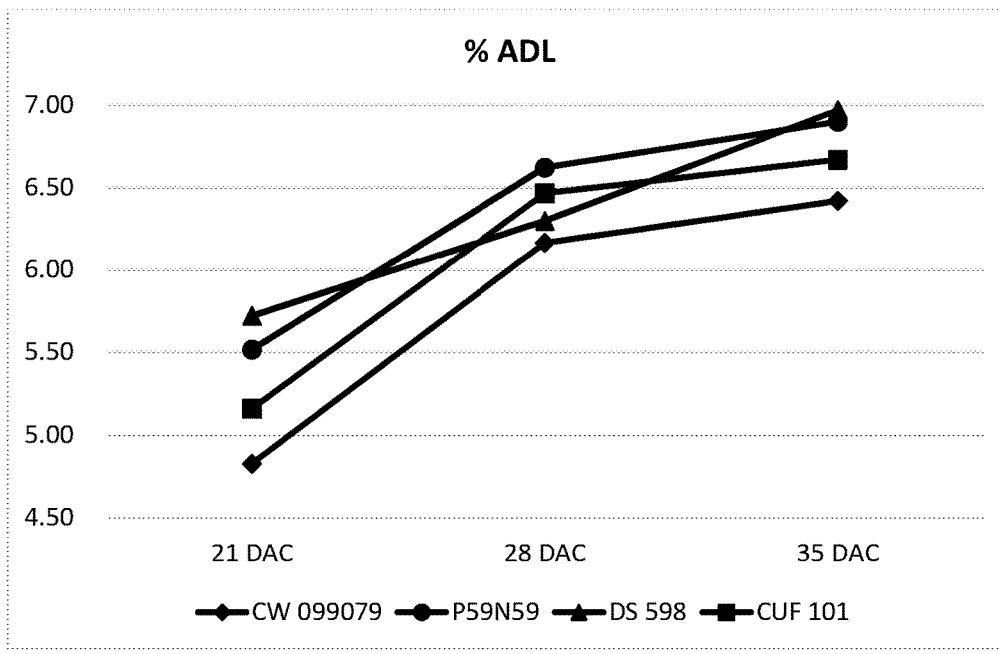
FIG. 8 shows the lignin content ("% ADL") after 21, 28, or 35 DAC of CW099079 compared to commercial varieties harvested in Year 1.
Figure 9:
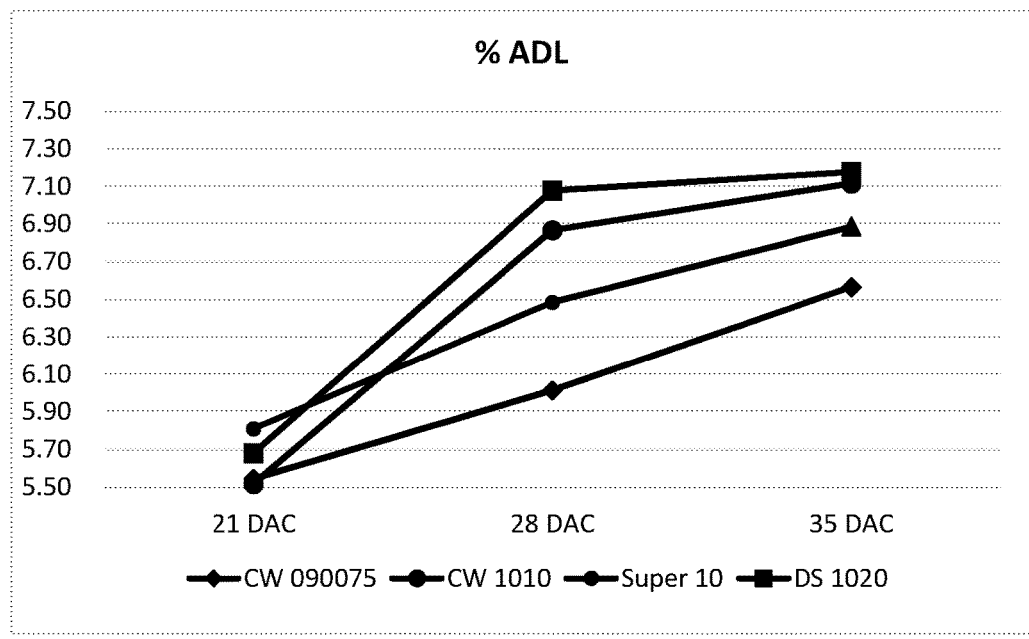
FIG. 9 shows the lignin content ("% ADL") after 21, 28, or 35 DAC of CW090075 compared to commercial varieties harvested in Year 1.

Tables 44-46 and FIGS. 7-9 summarize the lignin content measured as ADL from Tables 41-43.

TABLE 44

AVERAGE OF 2 CUTS

| Fall Dormancy | | % ADL | | |
|---|---|---|---|---|
| Group | Variety | 21 DAC | 28 DAC | 35 DAC |
| FD6 | CW 096043 | 4.90 | 5.28 | 5.79 |
| FD6 | P.56S82 | 4.74 | 6.42 | 6.63 |
| FD6 | HybriForce 2600 | 4.95 | 5.81 | 6.64 |
| FD6 | PGI 608 | 4.86 | 6.53 | 6.55 |

TABLE 45

AVERAGE OF 2 CUTS

| Fall Dormancy | | % ADL | | |
|---|---|---|---|---|
| Group | Variety | 21 DAC | 28 DAC | 35 DAC |
| FD9 | CW 099079 | 4.82 | 6.16 | 6.42 |
| FD9 | P59N59 | 5.52 | 6.62 | 6.90 |
| FD9 | DS 598 | 5.72 | 6.30 | 6.97 |
| FD9 | CUF 101 | 5.16 | 6.46 | 6.67 |

TABLE 46

AVERAGE OF 2 CUTS

| Fall Dormancy | | % ADL | | |
|---|---|---|---|---|
| Group | Variety | 21 DAC | 28 DAC | 35 DAC |
| FD10 | CW 090075 | 5.54 | 6.01 | 6.57 |
| FD10 | CW 1010 | 5.52 | 6.87 | 7.12 |
| FD10 | Super 10 | 5.81 | 6.48 | 6.89 |
| FD10 | DS 1020 | 5.68 | 7.08 | 7.18 |

The forage quality of CW090075 was compared to CW099079 and various commercially available fall dormancy groups 9 and 10 alfalfa varieties using the methods described in Example 1. CW090075, CW099079, and the commercially available alfalfa varieties were harvested in Year 0 at Stage 1 (21 DAC), Stage 2 (28 DAC), and Stage 3 (35 DAC). Tables 47-50.

TABLE 47

Dormancy Groups

| Fall Dormancy Group | Variety |
|---|---|
| FD9 | CW 099079 |
| FD9 | Magna 995 |
| FD9 | 4N900 |
| FD10 | CW 090075 |
| FD10 | CW 197 |
| FD10 | SW 10 |

TABLE 48

Year 1 Stage 1 (21 DAC)—Average of 2 cuts

| Variety | CP | ADF | aNDF | ADL | DM | IVTDMD | NDFD1 | TTNDFD | Dyn Kd |
|---|---|---|---|---|---|---|---|---|---|
| CW 099079 | 24.30 | 29.55 | 34.97 | 5.90 | 93.68 | 82.46 | 47.83 | 27.21 | 8.73 |
| Magna 995 | 23.71 | 29.44 | 35.28 | 5.97 | 93.44 | 81.61 | 46.71 | 23.74 | 8.52 |
| 4N900 | 24.39 | 29.00 | 34.62 | 5.81 | 93.63 | 82.62 | 47.91 | 26.71 | 8.95 |
| CW 090075 | 24.19 | 29.69 | 35.27 | 5.99 | 93.67 | 82.16 | 47.47 | 26.91 | 8.66 |
| CW 197 | 24.26 | 29.87 | 35.52 | 6.02 | 93.45 | 81.58 | 47.86 | 25.62 | 9.21 |
| SW 10 | 23.95 | 29.63 | 35.46 | 6.11 | 93.69 | 81.74 | 46.75 | 26.75 | 10.24 |
| Trial Average | 24.15 | 29.57 | 35.25 | 5.94 | 93.56 | 81.98 | 47.45 | 26.06 | 8.50 |
| LSD (0.05) | 1.38 | 1.54 | 1.74 | 0.32 | 0.17 | 1.39 | 1.44 | 3.34 | 3.87 |
| C.V. (%) | 3.9% | 3.6% | 3.4% | 3.8% | 0.1% | 1.2% | 2.1% | 8.9% | 31.6% |

TABLE 49

Year 1 Stage 2 (28 DAC)—Average of 2 cuts

| Variety | CP | ADF | aNDF | ADL | DM | IVTDMD | NDFD1 | TTNDFD | Dyn Kd |
|---|---|---|---|---|---|---|---|---|---|
| CW 099079 | 20.67 | 33.45 | 39.62 | 6.75 | 93.87 | 78.76 | 44.68 | 23.65 | 6.40 |
| Magna 995 | 20.31 | 32.58 | 39.07 | 6.77 | 93.46 | 78.25 | 43.49 | 20.52 | 6.25 |
| 4N900 | 19.49 | 34.65 | 41.23 | 7.14 | 93.63 | 77.15 | 43.21 | 21.10 | 5.59 |
| CW 090075 | 20.97 | 33.38 | 39.39 | 6.66 | 93.76 | 79.21 | 45.09 | 24.86 | 6.39 |
| CW 197 | 19.78 | 35.27 | 41.80 | 7.20 | 93.67 | 77.03 | 43.56 | 21.79 | 5.61 |
| SW 10 | 18.88 | 35.54 | 42.04 | 7.22 | 93.90 | 76.53 | 42.57 | 22.96 | 5.59 |
| Trial Average | 20.14 | 34.13 | 40.49 | 6.95 | 93.71 | 77.83 | 43.80 | 22.14 | 6.05 |
| LSD (0.05) | 1.13 | 1.51 | 1.72 | 0.35 | 0.27 | 1.48 | 1.38 | 3.03 | 1.45 |
| C.V. (%) | 3.9% | 3.1% | 2.9% | 3.5% | 0.2% | 1.3% | 2.2% | 9.5% | 16.6% |

TABLE 50

Year 1 Stage 3 (35 DAC)—Average of 2 cuts

| Variety | CP | ADF | aNDF | ADL | DM | IVTDMD | NDFD1 | TTNDFD | Dyn Kd |
|---|---|---|---|---|---|---|---|---|---|
| CW 099079 | 18.60 | 34.56 | 41.06 | 6.97 | 94.01 | 77.87 | 43.00 | 22.78 | 5.73 |
| Magna 995 | 18.32 | 34.89 | 42.08 | 7.39 | 93.54 | 75.86 | 40.61 | 19.11 | 5.94 |
| 4N900 | 18.05 | 35.27 | 42.52 | 7.43 | 93.70 | 75.91 | 41.17 | 19.79 | 5.65 |
| CW 090075 | 18.85 | 33.64 | 40.45 | 6.96 | 93.70 | 77.63 | 41.98 | 21.56 | 5.78 |
| CW 197 | 17.96 | 35.96 | 43.11 | 7.48 | 93.66 | 75.41 | 41.48 | 19.74 | 5.28 |
| SW 10 | 16.74 | 37.84 | 45.41 | 8.01 | 94.09 | 73.27 | 38.79 | 20.47 | 5.11 |
| Trial Average | 18.28 | 35.20 | 42.24 | 7.33 | 93.77 | 76.11 | 41.44 | 20.59 | 5.92 |
| LSD (0.05) | 1.41 | 1.70 | 1.92 | 0.41 | 0.25 | 1.86 | 1.99 | 2.60 | 1.80 |
| C.V. (%) | 5.3% | 3.4% | 3.2% | 3.9% | 0.2% | 1.7% | 3.3% | 8.7% | 21.1% |

Figure 12:
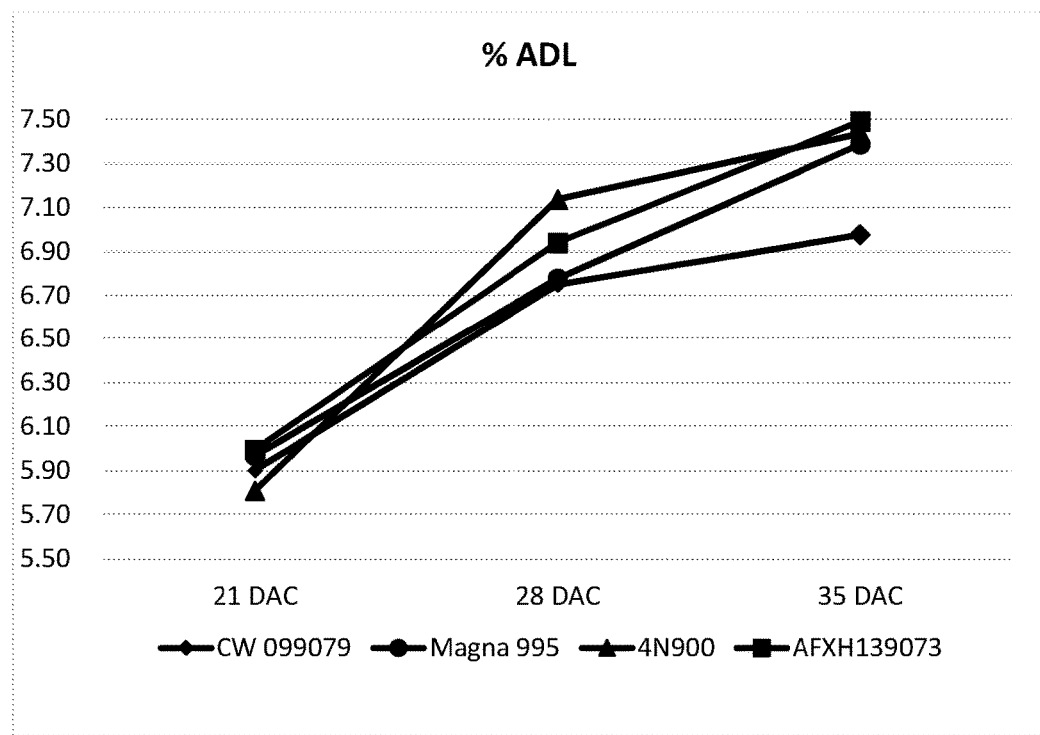
FIG. 12 shows the lignin content ("% ADL") after 21, 28, or 35 DAC of CW099079 compared to commercial varieties harvested in Year 1.
Figure 13:
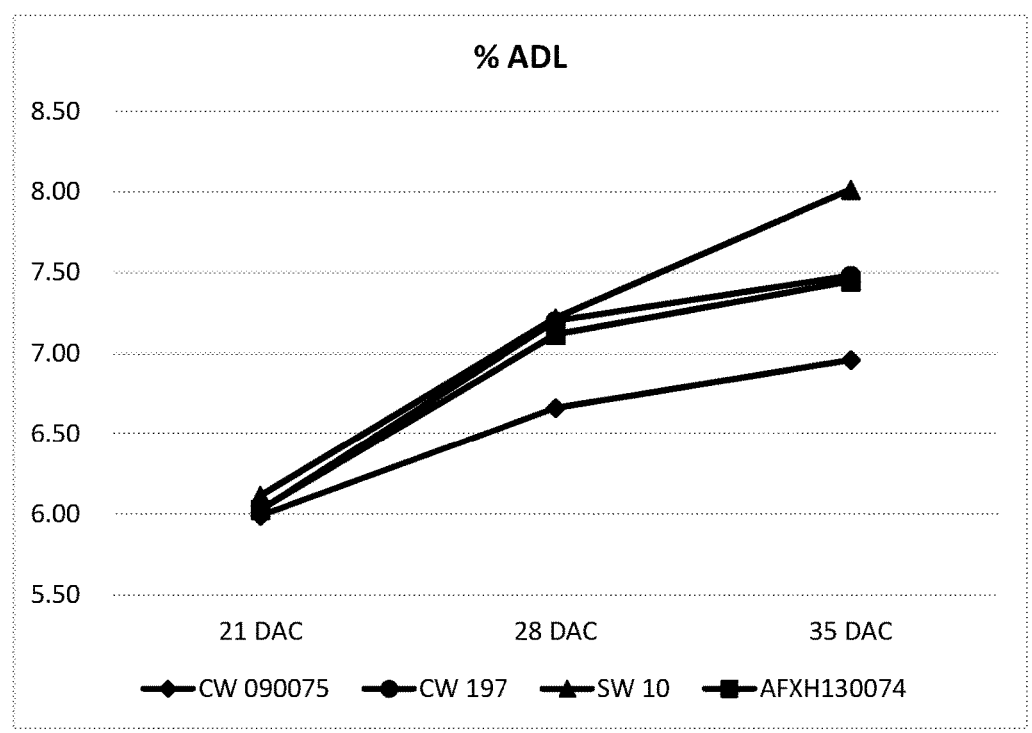
FIG. 13 shows the lignin content ("% ADL") after 21, 28, or 35 DAC of CW090075 compared to commercial varieties harvested in Year 1.

Tables 51 and 52 and FIGS. 12 and 13 summarize the lignin content measured as ADL from Tables 48-50.

TABLE 51

AVERAGE OF 2 CUTS

| | % ADL | | |
|---|---|---|---|
| Variety | 21 DAC | 28 DAC | 35 DAC |
| CW 099079 | 5.90 | 6.75 | 6.97 |
| Magna 995 | 5.97 | 6.77 | 7.39 |
| 4N900 | 5.81 | 7.14 | 7.43 |

TABLE 52

AVERAGE OF 2 CUTS

| | % ADL | | |
|---|---|---|---|
| Variety | 21 DAC | 28 DAC | 35 DAC |
| CW 090075 | 5.99 | 6.66 | 6.96 |
| CW 197 | 6.02 | 7.20 | 7.48 |
| SW 10 | 6.11 | 7.22 | 8.01 |

Figure 10:
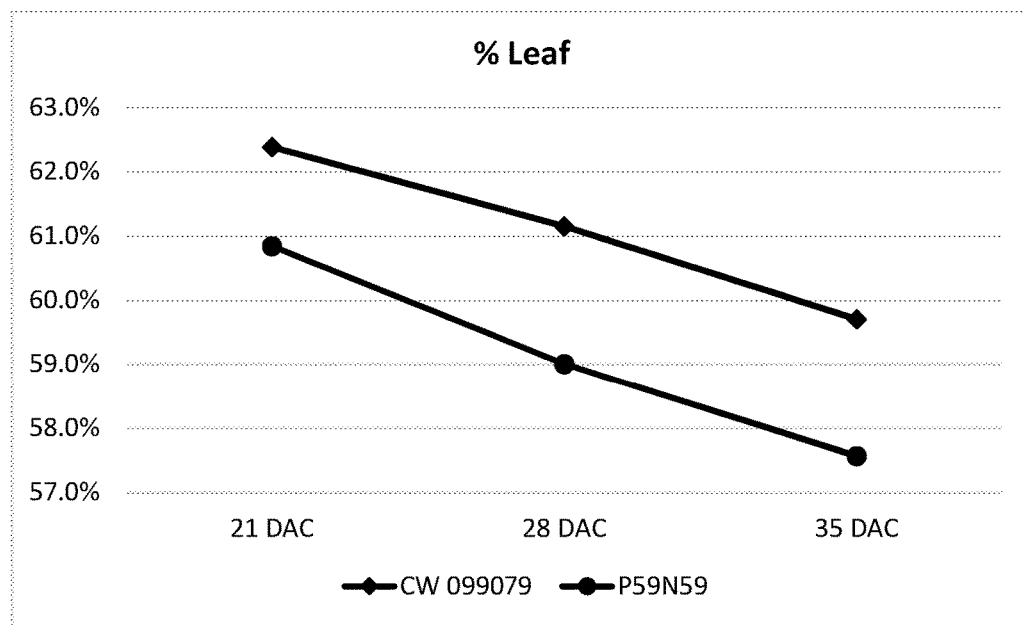
FIG. 10 shows the percentage of leaves (% Leaf) after 21, 28, or 35 DAC of CW099079 compared to commercial varieties harvested in Year 1.

Table 53 and FIG. 10 show the percentage of dry matter that is leaf tissue (% Leaf) in cut 4 harvested in Year 1 of CW099079 plants compare to a fall dormancy 9 commercial variety. The amount of dry matter that is stem tissue is 1.00-(% Leaf). The Leaf:stem ratio reflects plant and canopy architecture and is an indirect determinant of forage quality, including lignin content.

TABLE 53

| | % Leaf | | |
|---|---|---|---|
| Variety | 21 DAC | 28 DAC | 35 DAC |
| CW 099079 | 62.4% | 61.1% | 59.7% |
| P59N59 | 60.8% | 59.0% | 57.6% |

Figure 11:
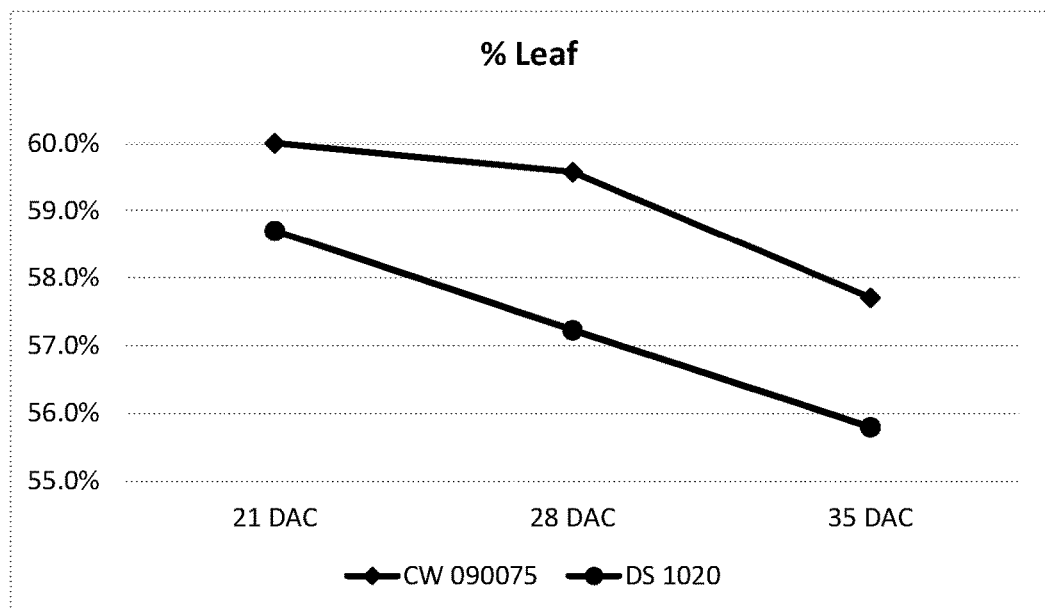
FIG. 11 shows the percentage of leaves (% Leaf) after 21, 28, or 35 DAC of CW090075 compared to commercial varieties harvested in Year 1.

Table 54 and FIG. 11 show the percentage of dry matter that is leaf tissue (% Leaf) in Cut 4 harvested in Year 1 of CW090075 plants compare to a fall dormancy 10 commercial variety. The amount of dry matter that is stem tissue is 1.00-(% Leaf). The Leaf:stem ratio reflects plant and canopy architecture and is an indirect determinant of forage quality, including lignin content.

TABLE 54

| | % Leaf | | |
|---|---|---|---|
| Variety | 21 DAC | 28 DAC | 35 DAC |
| CW 090075 | 60.0% | 59.6% | 57.7% |
| DS 1020 | 58.7% | 57.2% | 55.8% |

Example 10

CW054004

The forage quality of CW054004 was compared to various commercially available alfalfa varieties using the methods described in Example 1. CW054004 and the commercially available alfalfa varieties were harvested in May, June and July of Year 1. See Tables 55-57. The weighted mean for the three cuts is shown in Table 58.

TABLE 55

May Year 1—cut 1

| Variety | CP | ADF | NDF | ADL | DM | IVTDMD | NDFD1 | RFQ | Milk/ton | Milk/acre |
|---|---|---|---|---|---|---|---|---|---|---|
| CW 054004 | 22.87 | 33.34 | 37.49 | 5.95 | 94.80 | 82.93 | 52.69 | 174.53 | 3,000.00 | 8,094.47 |
| 53Q60 | 22.87 | 34.28 | 38.95 | 6.29 | 93.76 | 80.36 | 51.07 | 161.21 | 2,851.82 | 7,012.55 |
| 54H11 | 21.44 | 35.19 | 39.88 | 6.47 | 94.74 | 80.13 | 50.11 | 157.91 | 2,883.66 | 7,064.49 |
| 54H91 | 22.50 | 34.37 | 38.93 | 6.04 | 94.49 | 80.60 | 51.15 | 162.94 | 2,889.46 | 6,920.98 |
| 54V46 | 22.01 | 36.89 | 41.46 | 6.84 | 94.90 | 79.25 | 49.87 | 147.77 | 2,769.90 | 6,893.79 |
| Ameristand 403T | 22.95 | 34.56 | 38.99 | 6.33 | 94.47 | 81.08 | 51.33 | 163.67 | 2,891.54 | 7,413.75 |
| Ascend | 23.44 | 32.63 | 36.65 | 5.79 | 94.52 | 82.90 | 52.41 | 178.24 | 3,005.53 | 7,212.67 |
| PGI 215, Velvet | 22.56 | 33.34 | 37.11 | 5.78 | 94.71 | 82.77 | 52.52 | 175.94 | 2,994.45 | 7,628.63 |
| Foremost II, Valid | 23.10 | 34.34 | 38.74 | 6.19 | 94.74 | 81.19 | 50.59 | 162.13 | 2,863.42 | 7,172.36 |
| PGI 212, VR TOTAL | 24.01 | 33.10 | 37.11 | 5.83 | 94.43 | 82.71 | 53.87 | 175.53 | 2,947.72 | 7,795.31 |
| Assalt ST | 23.76 | 32.26 | 36.51 | 5.88 | 94.60 | 82.69 | 52.08 | 178.53 | 3,000.29 | 7,402.82 |
| 5010 | 23.64 | 32.22 | 36.32 | 5.87 | 94.16 | 82.37 | 51.93 | 177.19 | 2,952.54 | 7,062.32 |
| PGI 557, LELIA | 23.78 | 31.97 | 35.90 | 5.67 | 94.54 | 83.51 | 53.90 | 184.79 | 3,041.45 | 8,573.07 |
| Summit | 23.58 | 33.18 | 37.35 | 5.69 | 94.79 | 82.82 | 52.62 | 173.71 | 2,963.64 | 7,546.02 |
| Legend Extra | 24.14 | 32.07 | 35.81 | 5.64 | 95.24 | 84.48 | 52.33 | 184.21 | 3,050.55 | 7,816.60 |
| A 4330 | 23.24 | 33.44 | 37.80 | 5.91 | 94.46 | 82.25 | 51.80 | 170.26 | 2,946.24 | 7,612.07 |
| Exalt | 23.28 | 32.43 | 36.91 | 5.93 | 93.95 | 82.18 | 51.74 | 176.19 | 2,995.37 | 7,938.87 |
| A 5225 | 23.48 | 34.98 | 39.30 | 6.53 | 94.48 | 80.72 | 51.44 | 159.73 | 2,833.41 | 7,177.49 |
| SpringGold | 23.41 | 34.70 | 38.72 | 6.23 | 94.72 | 81.40 | 52.81 | 165.03 | 2,866.36 | 6,927.85 |
| GH 717 | 21.80 | 33.90 | 38.06 | 5.97 | 94.24 | 81.81 | 52.01 | 170.88 | 2,987.12 | 7,103.46 |
| Hvbf Force-400 | 22.20 | 34.63 | 39.05 | 6.00 | 94.22 | 80.90 | 52.35 | 164.36 | 2,912.73 | 7,140.34 |
| PGI 437 | 23.30 | 34.07 | 38.20 | 6.27 | 94.62 | 81.89 | 51.76 | 167.92 | 2,901.00 | 7,167.47 |
| PGI 459 | 22.52 | 34.56 | 38.92 | 6.15 | 94.62 | 81.64 | 51.24 | 163.94 | 2,920.22 | 7,814.57 |
| SummerGold | 23.85 | 32.04 | 35.95 | 5.68 | 93.97 | 82.86 | 53.03 | 181.76 | 2,982.91 | 7,428.00 |
| WL 319 HQ | 23.94 | 32.69 | 36.73 | 5.65 | 94.80 | 83.94 | 53.45 | 179.33 | 2,999.21 | 7,829.98 |
| WL 357 HQ | 23.40 | 33.00 | 37.09 | 5.92 | 94.89 | 82.74 | 51.78 | 174.34 | 2,969.77 | 7,693.96 |
| Grand Mean | 23.13 | 33.62 | 37.83 | 6.01 | 94.49 | 81.96 | 52.05 | 170.30 | 2,932.99 | 7,416.25 |
| LSD (0.05) | 1.41 | 2.40 | 2.67 | 0.64 | 0.97 | 2.32 | 2.03 | 18.10 | 155.47 | 732.62 |
| C.V. (%) | 3.72 | 4.37 | 4.33 | 6.50 | 0.63 | 1.73 | 2.39 | 6.51 | 3.25 | 6.05 |
| R2 | 0.52 | 0.47 | 0.49 | 0.48 | 0.38 | 0.47 | 0.51 | 0.45 | 0.39 | 0.52 |

TABLE 56

June Year 1—cut 2

| Variety | CP | ADF | NDF | ADL | DM | IVTDMD | NDFD1 | RFQ | Milk/ton | Milk/acre |
|---|---|---|---|---|---|---|---|---|---|---|
| CW 054004 | 20.50 | 31.83 | 36.98 | 5.79 | 94.77 | 82.64 | 52.24 | 181.94 | 3,143.22 | 5,922.92 |
| 53Q60 | 19.68 | 34.20 | 39.55 | 6.41 | 94.96 | 80.24 | 50.09 | 161.90 | 2,966.00 | 4,986.39 |
| 54H11 | 19.55 | 35.80 | 41.56 | 7.08 | 95.08 | 78.30 | 47.52 | 147.68 | 2,848.39 | 4,760.97 |
| 54H91 | 21.29 | 34.27 | 39.26 | 6.50 | 94.89 | 80.00 | 49.26 | 162.54 | 2,953.30 | 5,136.01 |
| 54V46 | 20.92 | 31.68 | 36.37 | 5.84 | 95.39 | 83.30 | 51.76 | 185.26 | 3,167.08 | 5,608.61 |
| Ameristand 403T | 21.72 | 32.18 | 36.60 | 5.84 | 95.22 | 83.41 | 52.31 | 183.56 | 3,132.58 | 5,070.29 |
| Ascend | 20.41 | 32.04 | 37.06 | 6.06 | 95.21 | 82.52 | 50.79 | 179.44 | 3,131.86 | 5,264.42 |
| PGI 215, Velvet | 20.03 | 31.32 | 36.62 | 5.81 | 95.34 | 83.00 | 51.15 | 183.63 | 3,172.04 | 5,495.97 |
| Foremost II, Valid | 19.34 | 33.50 | 39.18 | 6.55 | 94.84 | 80.09 | 48.18 | 162.84 | 3,004.86 | 4,898.20 |
| PGI 212, VR TOTAL | 21.53 | 30.61 | 35.39 | 5.65 | 94.94 | 83.71 | 51.36 | 190.05 | 3,178.82 | 5,656.46 |
| Assalt ST | 19.75 | 31.79 | 37.43 | 6.15 | 94.35 | 81.18 | 50.16 | 175.54 | 3,093.60 | 4,992.81 |
| 5010 | 20.07 | 32.63 | 38.21 | 6.38 | 94.92 | 81.03 | 49.28 | 168.79 | 3,029.02 | 5,705.88 |
| PGI 557, LELIA | 19.70 | 32.47 | 37.77 | 6.08 | 94.89 | 81.87 | 51.47 | 176.75 | 3,122.47 | 5,845.08 |
| Summit | 19.98 | 31.47 | 36.81 | 5.99 | 94.71 | 82.32 | 50.86 | 181.43 | 3,133.14 | 5,549.67 |
| Legend Extra | 19.95 | 30.18 | 35.41 | 5.64 | 95.01 | 84.24 | 52.34 | 194.74 | 3,248.46 | 5,654.92 |
| A 4330 | 19.45 | 31.71 | 37.53 | 6.16 | 94.90 | 81.58 | 49.59 | 175.69 | 3,113.24 | 5,200.73 |
| Exalt | 19.76 | 32.71 | 38.08 | 6.07 | 94.78 | 81.58 | 50.55 | 173.21 | 3,092.89 | 5,930.84 |
| A 5225 | 19.54 | 31.73 | 37.30 | 6.01 | 94.73 | 81.57 | 50.47 | 177.00 | 3,104.77 | 5,535.02 |
| SpringGold | 20.37 | 32.90 | 38.21 | 6.34 | 94.52 | 80.79 | 49.85 | 170.33 | 3,036.75 | 5,314.19 |
| GH 717 | 19.74 | 32.49 | 38.01 | 6.37 | 94.60 | 81.22 | 50.52 | 174.50 | 3,123.33 | 5,727.32 |
| Hvbf Force-400 | 19.70 | 32.22 | 37.48 | 5.91 | 94.95 | 82.38 | 51.75 | 179.74 | 3,158.66 | 5,043.84 |
| PGI 437 | 19.16 | 35.06 | 40.69 | 7.10 | 94.73 | 78.52 | 48.06 | 153.49 | 2,900.53 | 4,706.67 |

TABLE 56-continued

June Year 1—cut 2

| Variety | CP | ADF | NDF | ADL | DM | IVTDMD | NDFD1 | RFQ | Milk/ton | Milk/acre |
|---|---|---|---|---|---|---|---|---|---|---|
| PGI 459 | 19.31 | 33.28 | 38.74 | 6.37 | 94.84 | 81.01 | 49.82 | 168.70 | 3,069.67 | 5,583.49 |
| SummerGold | 20.01 | 33.29 | 38.71 | 6.37 | 94.35 | 80.54 | 50.15 | 168.76 | 3,051.34 | 5,242.82 |
| WL 319 HQ | 20.52 | 30.88 | 35.93 | 5.93 | 95.22 | 83.50 | 50.57 | 186.52 | 3,175.92 | 5,492.16 |
| WL 357 HQ | 20.24 | 33.46 | 38.77 | 6.38 | 95.21 | 80.95 | 49.52 | 166.01 | 3,012.86 | 5,317.54 |
| Grand Mean | 19.97 | 32.59 | 37.94 | 6.20 | 94.88 | 81.51 | 50.31 | 173.52 | 3,078.80 | 5,431.69 |
| LSD (0.05) | 1.39 | 2.66 | 2.83 | 0.62 | 0.77 | 2.48 | 2.03 | 19.76 | 164.93 | 504.17 |
| C.V. (%) | 4.27 | 4.99 | 4.57 | 6.17 | 0.50 | 1.86 | 2.47 | 6.97 | 3.28 | 5.68 |
| R2 | 0.61 | 0.46 | 0.50 | 0.56 | 0.40 | 0.57 | 0.57 | 0.51 | 0.47 | 0.63 |

TABLE 57

July Year 1—cut 3

| Variety | CP | ADF | NDF | ADL | DM | IVTDMD | NDFD1 | RFQ | Milk/ton | Milk/acre |
|---|---|---|---|---|---|---|---|---|---|---|
| CW 054004 | 21.41 | 36.13 | 40.20 | 6.57 | 93.36 | 77.32 | 48.57 | 145.55 | 2,615.00 | 3,838.93 |
| 53Q60 | 21.71 | 35.47 | 38.96 | 6.34 | 92.94 | 77.92 | 48.89 | 150.69 | 2,616.54 | 3,181.69 |
| 54H11 | 21.61 | 36.85 | 40.04 | 6.95 | 93.94 | 76.78 | 47.65 | 142.75 | 2,544.07 | 2,801.19 |
| 54H91 | 22.22 | 39.63 | 40.02 | 7.19 | 94.51 | 80.15 | 51.01 | 143.72 | 2,471.17 | 2,894.08 |
| 54V46 | 21.98 | 34.97 | 38.50 | 6.59 | 93.48 | 78.01 | 48.28 | 153.89 | 2,676.62 | 3,621.81 |
| Ameristand 403T | 22.69 | 39.39 | 39.84 | 7.39 | 95.14 | 81.41 | 51.26 | 146.01 | 2,509.04 | 3,097.94 |
| Ascend | 21.70 | 36.92 | 40.72 | 7.09 | 93.99 | 76.47 | 47.19 | 139.80 | 2,528.53 | 3,375.36 |
| PGI 215, Velvet | 22.77 | 35.56 | 38.70 | 6.52 | 93.36 | 77.87 | 48.74 | 150.30 | 2,572.00 | 3,208.48 |
| Foremost II, Valid | 22.06 | 34.46 | 38.26 | 6.38 | 93.42 | 78.40 | 48.54 | 154.35 | 2,663.69 | 3,443.15 |
| PGI 212, VR TOTAL | 22.68 | 32.27 | 35.54 | 5.77 | 92.63 | 80.42 | 50.14 | 173.94 | 2,825.74 | 3,927.47 |
| Assalt ST | 21.37 | 37.18 | 39.95 | 7.22 | 94.23 | 79.18 | 48.01 | 144.52 | 2,578.22 | 3,374.06 |
| 5010 | 21.35 | 35.86 | 40.08 | 6.84 | 94.14 | 77.12 | 47.32 | 144.38 | 2,608.96 | 4,244.43 |
| PGI 557, LELIA | 20.86 | 34.46 | 38.40 | 6.37 | 93.89 | 78.90 | 49.33 | 157.62 | 2,745.13 | 4,144.57 |
| Summit | 21.34 | 35.36 | 38.08 | 6.50 | 93.66 | 78.76 | 49.19 | 155.66 | 2,652.92 | 4,222.26 |
| Legend Extra | 21.58 | 36.41 | 38.26 | 6.60 | 94.85 | 81.04 | 51.15 | 156.16 | 2,638.26 | 3,572.50 |
| A 4330 | 21.45 | 34.34 | 38.49 | 6.53 | 93.51 | 77.63 | 47.01 | 152.03 | 2,655.84 | 3,434.73 |
| Exalt | 21.84 | 37.82 | 40.75 | 7.17 | 94.30 | 77.88 | 48.62 | 139.49 | 2,493.01 | 3,810.09 |
| A 5225 | 21.07 | 34.98 | 39.31 | 6.58 | 93.16 | 77.06 | 47.52 | 149.02 | 2,639.84 | 3,646.43 |
| SpringGold | 20.88 | 37.22 | 41.33 | 7.15 | 93.46 | 76.23 | 47.02 | 138.51 | 2,540.45 | 3,880.65 |
| GH 717 | 21.06 | 38.63 | 40.40 | 7.40 | 94.21 | 79.38 | 48.55 | 140.17 | 2,480.77 | 3,291.79 |
| HybriForce-400 | 22.28 | 35.71 | 39.51 | 6.70 | 93.32 | 76.92 | 47.73 | 146.10 | 2,588.08 | 3,079.43 |
| PGI 437 | 21.53 | 37.19 | 40.72 | 7.04 | 93.93 | 76.59 | 47.51 | 138.62 | 2,497.92 | 2,904.84 |
| PGI 459 | 21.12 | 33.96 | 37.90 | 6.36 | 93.20 | 78.50 | 48.53 | 159.02 | 2,748.36 | 3,761.07 |
| SummerGold | 22.81 | 35.00 | 38.41 | 6.80 | 93.79 | 78.18 | 47.89 | 151.76 | 2,629.20 | 3,465.44 |
| WL 319 HQ | 23.72 | 34.82 | 37.74 | 6.50 | 94.02 | 79.20 | 49.85 | 157.33 | 2,651.60 | 3,511.95 |
| WL 357 HQ | 22.00 | 34.84 | 38.56 | 6.58 | 93.70 | 78.29 | 48.36 | 152.88 | 2,656.54 | 3,615.83 |
| Grand Mean | 21.77 | 35.89 | 39.17 | 6.72 | 93.72 | 78.12 | 48.47 | 149.04 | 2,603.96 | 3,600.02 |
| LSD (0.05) | 1.51 | 3.01 | 2.61 | 0.73 | 1.30 | 3.14 | 2.55 | 15.89 | 175.79 | 337.83 |
| C.V. (%) | 4.25 | 5.14 | 4.08 | 6.69 | 0.85 | 2.46 | 3.22 | 6.53 | 4.13 | 5.75 |
| R2 | 0.50 | 0.49 | 0.48 | 0.51 | 0.40 | 0.38 | 0.46 | 0.49 | 0.46 | 0.86 |

TABLE 58

Year 1—Weighted Mean

| Variety | CP | ADF | NDF | ADL | DM | IVTDMD | NDFD1 | RFQ | Milk/ton | Milk/acre |
|---|---|---|---|---|---|---|---|---|---|---|
| CW 054004 | 21.78 | 33.56 | 37.99 | 6.05 | 94.44 | 81.47 | 51.56 | 169.78 | 2950.47 | 17856.32 |
| 53Q60 | 21.62 | 34.53 | 39.15 | 6.34 | 93.95 | 79.77 | 50.28 | 158.99 | 2833.51 | 15180.63 |
| 54H11 | 20.87 | 35.74 | 40.46 | 6.77 | 94.68 | 78.84 | 48.76 | 151.42 | 2801.01 | 14626.65 |
| 54H91 | 22.05 | 35.47 | 39.26 | 6.44 | 94.63 | 80.32 | 50.50 | 158.72 | 2820.23 | 14951.07 |
| 54V46 | 21.65 | 34.79 | 39.14 | 6.47 | 94.71 | 80.22 | 50.09 | 161.06 | 2872.82 | 16124.21 |
| Ameristand 403T | 22.52 | 34.94 | 38.46 | 6.42 | 94.85 | 81.86 | 51.60 | 165.61 | 2876.73 | 15581.98 |
| Ascend | 22.07 | 33.51 | 37.79 | 6.20 | 94.60 | 81.20 | 50.63 | 169.12 | 2926.81 | 15852.44 |
| PGI 215, Velvet | 21.81 | 33.22 | 37.33 | 5.96 | 94.61 | 81.73 | 51.22 | 172.48 | 2953.71 | 16333.08 |

TABLE 58-continued

| | | | | Year 1—Weighted Mean | | | | | | |
|---|---|---|---|---|---|---|---|---|---|---|
| Variety | CP | ADF | NDF | ADL | DM | IVTDMD | NDFD1 | RFQ | Milk/ton | Milk/acre |
| Foremost II, Valid | 21.72 | 34.12 | 38.76 | 6.35 | 94.45 | 80.19 | 49.38 | 160.46 | 2858.32 | 15513.71 |
| PGI 212, VR TOTAL | 22.93 | 32.15 | 36.21 | 5.76 | 94.16 | 82.47 | 52.22 | 179.56 | 2988.77 | 17379.24 |
| Assalt ST | 21.98 | 33.31 | 37.62 | 6.29 | 94.43 | 81.38 | 50.51 | 169.37 | 2925.76 | 15769.68 |
| 5010 | 21.87 | 33.35 | 37.95 | 6.30 | 94.40 | 80.50 | 49.82 | 165.53 | 2882.85 | 17012.62 |
| PGI 557, LELIA | 21.85 | 32.74 | 37.08 | 5.96 | 94.49 | 81.89 | 52.07 | 175.70 | 2992.92 | 18562.71 |
| Summit | 21.89 | 33.26 | 37.39 | 6.00 | 94.47 | 81.58 | 51.17 | 171.14 | 2931.13 | 17317.94 |
| Legend Extra | 22.24 | 32.56 | 36.32 | 5.88 | 95.07 | 83.55 | 52.02 | 180.43 | 3010.94 | 17044.03 |
| A 4330 | 21.69 | 33.12 | 37.86 | 6.13 | 94.37 | 80.99 | 50.04 | 167.77 | 2929.80 | 16247.53 |
| Exalt | 21.81 | 33.90 | 38.25 | 6.29 | 94.31 | 80.92 | 50.60 | 165.97 | 2898.70 | 17679.80 |
| A 5225 | 21.67 | 33.99 | 38.71 | 6.38 | 94.24 | 80.07 | 50.16 | 162.32 | 2869.30 | 16358.93 |
| SpringGold | 21.81 | 34.81 | 39.25 | 6.51 | 94.32 | 79.83 | 50.33 | 159.57 | 2831.40 | 16122.70 |
| GH 717 | 20.94 | 34.59 | 38.61 | 6.45 | 94.35 | 81.04 | 50.68 | 164.64 | 2909.77 | 16122.58 |
| HybriForce-400 | 21.46 | 34.15 | 38.69 | 6.13 | 94.24 | 80.44 | 51.12 | 164.83 | 2913.14 | 15263.61 |
| PGI 437 | 21.63 | 35.06 | 39.53 | 6.70 | 94.50 | 79.68 | 49.67 | 157.01 | 2812.37 | 14778.99 |
| PGI 459 | 21.20 | 34.02 | 38.63 | 6.27 | 94.36 | 80.71 | 50.17 | 164.25 | 2926.41 | 17159.14 |
| SummerGold | 22.41 | 33.14 | 37.40 | 6.16 | 94.05 | 81.02 | 50.91 | 170.54 | 2919.73 | 16136.26 |
| WL 319 HQ | 22.84 | 32.67 | 36.76 | 5.94 | 94.75 | 82.68 | 51.74 | 176.16 | 2970.70 | 16834.08 |
| WL 357 HQ | 22.10 | 33.59 | 37.97 | 6.22 | 94.70 | 81.12 | 50.26 | 166.59 | 2907.74 | 16627.33 |
| Grand Mean | 21.81 | 33.86 | 38.20 | 6.24 | 94.42 | 80.88 | 50.63 | 166.05 | 2897.86 | 16447.96 |
| LSD (0.05) | 0.88 | 1.47 | 1.57 | 0.37 | 0.55 | 1.49 | 1.31 | 10.35 | 93.91 | 1167.86 |
| C.V. (%) | 2.46 | 2.66 | 2.51 | 3.66 | 0.36 | 1.12 | 1.59 | 3.82 | 1.98 | 4.35 |
| R2 | 0.66 | 0.56 | 0.59 | 0.64 | 0.46 | 0.60 | 0.61 | 0.59 | 0.51 | 0.73 |

The ADL advantage of CW054004 compared to other commercially available alfalfa varieties is shown in Table 59.

TABLE 59

| | | May | | June | | July | | Weighted Mean | |
|---|---|---|---|---|---|---|---|---|---|
| FD Group | Variety | ADL Adv. | % ADL Adv. | ADL Adv. | % ADL Adv. | ADL Adv. | % ADL Adv. | ADL Adv. | % ADL Adv. |
| FD2 | PGI 215, Velvet | −0.17 | −3% | 0.03 | 0% | −0.05 | −1% | −0.09 | −1% |
| FD2 | PGI 212, VR TOTAL | −0.12 | −2% | −0.14 | −2% | −0.81 | −14% | −0.29 | −5% |
| FD3 | 53Q60 | 0.34 | 5% | 0.62 | 10% | −0.23 | −4% | 0.29 | 5% |
| FD3 | Legend Extra | −0.31 | −5% | −0.15 | −3% | 0.03 | 0% | −0.17 | −3% |
| FD3 | WL 319 HQ | −0.30 | −5% | 0.15 | 2% | −0.08 | −1% | −0.11 | −2% |
| FD4 | CW 054004 | 0.00 | 0% | 0.00 | 0% | 0.00 | 0% | 0.00 | 0% |
| FD4 | 54H11 | 0.52 | 8% | 1.30 | 18% | 0.37 | 5% | 0.72 | 11% |
| FD4 | 54H91 | 0.09 | 1% | 0.71 | 11% | 0.62 | 9% | 0.39 | 6% |
| FD4 | 54V46 | 0.89 | 13% | 0.06 | 1% | 0.02 | 0% | 0.41 | 6% |
| FD4 | Ameristand 403T | 0.38 | 6% | 0.05 | 1% | 0.81 | 11% | 0.37 | 6% |
| FD4 | Foremost II, Valid | 0.24 | 4% | 0.76 | 12% | −0.20 | −3% | 0.29 | 5% |
| FD4 | Assalt ST | −0.07 | −1% | 0.36 | 6% | 0.65 | 9% | 0.24 | 4% |
| FD4 | Summit | −0.27 | −5% | 0.20 | 3% | −0.07 | −1% | −0.05 | −1% |
| FD4 | A 4330 | −0.04 | −1% | 0.38 | 6% | −0.04 | −1% | 0.08 | 1% |
| FD4 | Exalt | −0.02 | 0% | 0.29 | 5% | 0.59 | 8% | 0.24 | 4% |
| FD4 | GH 717 | 0.02 | 0% | 0.58 | 9% | 0.82 | 11% | 0.40 | 6% |
| FD4 | HybriForce-400 | 0.05 | 1% | 0.12 | 2% | 0.13 | 2% | 0.08 | 1% |
| FD4 | PGI 437 | 0.32 | 5% | 1.31 | 18% | 0.47 | 7% | 0.65 | 10% |
| FD4 | PGI 459 | 0.20 | 3% | 0.58 | 9% | −0.21 | −3% | 0.22 | 3% |
| FD4 | SummerGold | −0.28 | −5% | 0.58 | 9% | 0.23 | 3% | 0.11 | 2% |
| FD5 | Ascend | −0.16 | −3% | 0.28 | 5% | 0.52 | 7% | 0.14 | 2% |
| FD5 | 5010 | −0.08 | −1% | 0.59 | 9% | 0.27 | 4% | 0.25 | 4% |
| FD5 | PGI 557, LELIA | −0.28 | −5% | 0.29 | 5% | −0.21 | −3% | −0.09 | −1% |
| FD5 | A 5225 | 0.58 | 9% | 0.22 | 4% | 0.00 | 0% | 0.33 | 5% |
| FD5 | SpringGold | 0.28 | 4% | 0.55 | 9% | 0.57 | 8% | 0.46 | 7% |
| FD5 | WL 357 HQ | −0.03 | 0% | 0.59 | 9% | 0.01 | 0% | 0.17 | 3% |

CW054004 and commercially available alfalfa varieties were grown in Wisconsin and harvested at about 28 and 35 days in Year 1. Table 60 shows the weighted mean of 5 cuts of 28 days. Table 62 shows the weighted mean of 3 cuts of 35 days. Table 64 shows the weighted mean of 5 cuts of 28 days in a different trial. Table 66 shows the weighted mean of 3 cuts of 35 days in a different trial. The ADL advantage of CW054004 compared to other commercially available alfalfa varieties for the data of Tables 60, 62, 64, and 66 are shown in Tables 61, 63, 65, and 67, respectively.

TABLE 60

Year 1—Weighted Mean (28 days)

| Variety | CP | ADF | aNDF | ADL | DM | IVTDMD | NDFD1 | RFQ | RFV | Milk/ton | Milk/acre |
|---|---|---|---|---|---|---|---|---|---|---|---|
| CW 054004 | 23.11 | 31.56 | 36.98 | 5.66 | 92.86 | 79.65 | 47.90 | 168.61 | 167.26 | 2,725.38 | 25,889.13 |
| 54H11 | 22.24 | 32.46 | 38.18 | 6.03 | 93.02 | 78.86 | 47.03 | 160.82 | 159.63 | 2,697.53 | 22,238.64 |
| 55V12 | 21.91 | 32.64 | 38.59 | 6.15 | 93.51 | 78.28 | 46.58 | 157.06 | 156.57 | 2,692.42 | 23,327.14 |
| A 30-06 | 23.18 | 31.53 | 36.99 | 5.78 | 93.11 | 79.91 | 48.41 | 169.88 | 167.15 | 2,736.99 | 22,798.67 |
| Ameristand 407TQ | 22.13 | 33.04 | 38.81 | 6.07 | 93.15 | 78.40 | 47.45 | 159.76 | 158.32 | 2,654.18 | 24,017.40 |
| eXclaim | 23.18 | 31.29 | 36.78 | 5.71 | 92.77 | 79.69 | 47.46 | 168.08 | 167.77 | 2,730.36 | 24,522.43 |
| PERFORMER | 22.83 | 31.98 | 37.46 | 5.87 | 92.98 | 79.23 | 47.42 | 164.18 | 163.59 | 2,698.20 | 24,821.97 |
| 243, STEALTH II | 22.20 | 32.46 | 38.34 | 6.04 | 92.98 | 78.62 | 47.26 | 160.56 | 159.14 | 2,700.21 | 25,418.26 |
| SHOWDOWN | 22.75 | 31.52 | 37.14 | 5.78 | 93.06 | 79.47 | 47.83 | 167.06 | 165.46 | 2,732.95 | 25,006.28 |
| Sundance II, Sansar | 22.93 | 31.18 | 36.86 | 5.72 | 93.06 | 79.79 | 47.86 | 168.50 | 166.92 | 2,755.87 | 24,358.99 |
| PGI 212, VR TOTAL | 23.48 | 30.61 | 35.85 | 5.55 | 93.07 | 80.53 | 48.65 | 176.41 | 173.97 | 2,781.26 | 24,367.39 |
| 5010 | 22.55 | 31.17 | 36.94 | 5.77 | 93.02 | 79.34 | 46.97 | 168.68 | 167.97 | 2,776.03 | 25,778.23 |
| PGI 557, LELIA | 22.96 | 31.80 | 37.27 | 5.86 | 92.88 | 78.99 | 47.01 | 164.14 | 164.18 | 2,706.30 | 24,109.01 |
| Summit | 22.81 | 31.72 | 37.35 | 5.87 | 93.00 | 79.32 | 47.38 | 165.69 | 165.09 | 2,719.38 | 25,632.69 |
| SolarGold, CORNERSTONE | 22.34 | 32.53 | 38.04 | 5.88 | 93.09 | 78.97 | 47.37 | 162.10 | 160.67 | 2,686.15 | 26,368.05 |
| Contender | 22.79 | 32.90 | 38.47 | 6.10 | 93.04 | 78.45 | 46.92 | 157.42 | 157.62 | 2,632.80 | 25,568.50 |
| Legend Extra | 23.38 | 31.89 | 37.27 | 5.80 | 92.77 | 79.47 | 47.74 | 165.59 | 165.14 | 2,678.88 | 23,676.71 |
| PGI 437, Tower ST | 22.53 | 31.74 | 37.25 | 5.90 | 92.90 | 79.38 | 47.01 | 163.44 | 163.40 | 2,716.37 | 21,893.10 |
| Exalt | 23.00 | 30.82 | 36.24 | 5.56 | 93.34 | 80.14 | 48.36 | 172.57 | 170.13 | 2,776.95 | 26,200.42 |
| PGI 459, Quest | 21.70 | 33.14 | 39.00 | 6.19 | 93.10 | 78.29 | 47.06 | 155.47 | 154.18 | 2,663.56 | 24,109.77 |
| HybriForce-400 | 22.25 | 31.56 | 37.10 | 5.80 | 92.81 | 79.66 | 47.88 | 167.92 | 166.46 | 2,720.67 | 21,747.52 |
| Rugged | 23.63 | 31.26 | 36.55 | 5.78 | 93.14 | 79.96 | 48.03 | 170.63 | 169.64 | 2,726.40 | 20,414.98 |
| TS 4006 | 23.66 | 31.76 | 36.88 | 5.74 | 93.08 | 79.89 | 48.13 | 167.43 | 166.37 | 2,683.27 | 22,325.53 |
| TS 4007 | 22.45 | 32.68 | 38.12 | 5.89 | 92.99 | 79.16 | 47.62 | 161.56 | 159.95 | 2,659.32 | 22,137.72 |
| TS 4010 | 23.05 | 32.36 | 37.90 | 6.01 | 93.05 | 79.23 | 47.78 | 162.49 | 161.53 | 2,660.46 | 21,214.46 |
| TS 4013 | 23.08 | 31.41 | 37.07 | 5.87 | 93.49 | 79.45 | 47.72 | 167.71 | 166.46 | 2,740.02 | 22,513.23 |
| TS 4027 | 22.74 | 32.05 | 37.58 | 5.80 | 92.96 | 79.32 | 47.85 | 164.10 | 162.53 | 2,695.40 | 23,316.65 |
| WL 319 HQ | 23.83 | 29.87 | 34.98 | 5.37 | 92.91 | 81.19 | 48.90 | 180.60 | 178.30 | 2,816.83 | 23,880.92 |
| Grand Mean | 22.82 | 31.78 | 37.33 | 5.84 | 93.02 | 79.40 | 47.61 | 165.82 | 164.71 | 2,713.96 | 23,836.51 |
| LSD (0.05) | 0.57 | 1.29 | 1.37 | 0.28 | 0.45 | 0.97 | 0.81 | 8.88 | 8.07 | 88.79 | 1,536.88 |
| C.V. (%) | 1.54 | 2.49 | 2.24 | 2.94 | 0.29 | 0.75 | 1.04 | 3.28 | 3.00 | 2.00 | 3.95 |
| R2 | 0.73 | 0.53 | 0.58 | 0.59 | 0.51 | 0.59 | 0.62 | 0.56 | 0.57 | 0.46 | 0.78 |

TABLE 61

| | | Cut 1 | | Cut 2 | | Cut 3 | | Cut 4 | | Cut 5 | | Weighted Average | |
|---|---|---|---|---|---|---|---|---|---|---|---|---|---|
| FD Group | Variety | ADL Adv. | % ADL Adv. | ADL Adv. | % ADL Adv. | ADL Adv. | % ADL Adv. | ADL Adv. | % ADL Adv. | ADL Adv. | % ADL Adv. | ADL Adv. | % ADL Adv. |
| FD2 | PGI 212, VR TOTAL | −0.01 | 0% | −0.01 | 0% | −0.30 | −5% | −0.04 | −1% | −0.23 | −5% | −0.11 | −2% |
| FD3 | eXclaim | 0.22 | 5% | −0.06 | −1% | 0.13 | 2% | 0.03 | 1% | 0.09 | 2% | 0.05 | 1% |
| FD3 | Legend Extra | 0.36 | 8% | 0.23 | 3% | 0.00 | 0% | −0.56 | −11% | 0.57 | 11% | 0.13 | 2% |
| FD3 | Rugged | 0.26 | 6% | 0.46 | 6% | 0.09 | 1% | −0.03 | −1% | −0.04 | −1% | 0.11 | 2% |
| FD3 | WL 319 HQ | 0.11 | 3% | −0.75 | −12% | −0.13 | −2% | −0.17 | −3% | 0.00 | 0% | −0.29 | −5% |
| FD4 | CW 054004 | 0.00 | 0% | 0.00 | 0% | 0.00 | 0% | 0.00 | 0% | 0.00 | 0% | 0.00 | 0% |
| FD4 | 54H11 | 0.49 | 11% | 0.33 | 4% | 0.52 | 8% | 0.35 | 6% | 0.46 | 9% | 0.36 | 6% |
| FD4 | A 30-06 | 0.19 | 4% | 0.10 | 1% | 0.44 | 7% | 0.19 | 3% | −0.02 | 0% | 0.12 | 2% |
| FD4 | Ameristand 407TQ | 0.23 | 5% | 1.00 | 12% | 0.17 | 3% | −0.06 | −1% | 0.15 | 3% | 0.41 | 7% |
| FD4 | PERFORMER | 0.30 | 7% | 0.26 | 3% | 0.24 | 4% | 0.19 | 3% | 0.06 | 1% | 0.21 | 4% |
| FD4 | Sundance II, Sansar | 0.33 | 7% | −0.15 | −2% | −0.04 | −1% | 0.31 | 5% | 0.17 | 3% | 0.06 | 1% |
| FD4 | Summit | 0.26 | 6% | 0.32 | 4% | 0.26 | 4% | 0.00 | 0% | 0.28 | 6% | 0.21 | 4% |
| FD4 | SolarGold, CORNERSTONE | 0.10 | 2% | 0.41 | 5% | 0.27 | 4% | 0.15 | 2% | 0.28 | 6% | 0.22 | 4% |
| FD4 | PGI 437, Tower ST | 0.74 | 15% | −0.12 | −2% | 0.23 | 4% | 0.20 | 3% | 0.40 | 8% | 0.24 | 4% |
| FD4 | Exalt | 0.18 | 4% | −0.46 | −7% | −0.01 | 0% | −0.24 | −4% | 0.23 | 5% | −0.10 | −2% |
| FD4 | PGI 459, Quest | 0.59 | 12% | 0.58 | 7% | 0.42 | 7% | 0.46 | 7% | 0.48 | 9% | 0.52 | 8% |
| FD4 | HybriForce-400 | 0.20 | 5% | 0.17 | 2% | 0.25 | 4% | 0.13 | 2% | 0.45 | 9% | 0.14 | 2% |

TABLE 61-continued

| | | Cut 1 | | Cut 2 | | Cut 3 | | Cut 4 | | Cut 5 | | Weighted Average | |
|---|---|---|---|---|---|---|---|---|---|---|---|---|---|
| FD Group | Variety | ADL Adv. | % ADL Adv. | ADL Adv. | % ADL Adv. | ADL Adv. | % ADL Adv. | ADL Adv. | % ADL Adv. | ADL Adv. | % ADL Adv. | ADL Adv. | % ADL Adv. |
| FD4 | TS 4006 | 0.27 | 6% | 0.09 | 1% | -0.07 | -1% | 0.04 | 1% | 0.16 | 3% | 0.08 | 1% |
| FD4 | TS 4007 | 0.32 | 7% | 0.24 | 3% | 0.60 | 9% | -0.04 | -1% | 0.26 | 5% | 0.23 | 4% |
| FD4 | TS 4010 | 0.36 | 8% | 0.59 | 8% | 0.30 | 5% | 0.21 | 4% | 0.17 | 3% | 0.35 | 6% |
| FD4 | TS 4013 | 0.32 | 7% | 0.32 | 4% | -0.06 | -1% | 0.17 | 3% | 0.52 | 10% | 0.21 | 4% |
| FD4 | TS 4027 | 0.43 | 9% | 0.15 | 2% | -0.05 | -1% | 0.12 | 2% | -0.07 | -2% | 0.14 | 2% |
| FD5 | 55V12 | 0.69 | 14% | 0.58 | 8% | 0.24 | 4% | 0.48 | 8% | 0.43 | 8% | 0.49 | 8% |
| FD5 | 243, STEALTH II | 0.33 | 7% | 0.67 | 9% | 0.05 | 1% | 0.27 | 4% | 0.55 | 10% | 0.38 | 6% |
| FD5 | SHOWDOWN | 0.28 | 6% | -0.10 | -1% | 0.15 | 2% | 0.18 | 3% | 0.38 | 7% | 0.12 | 2% |
| FD5 | 5010 | 0.07 | 2% | -0.02 | 0% | 0.28 | 4% | 0.12 | 2% | 0.58 | 11% | 0.11 | 2% |
| FD5 | PGI 557, LELIA | 0.41 | 9% | 0.18 | 2% | 0.06 | 1% | 0.14 | 2% | 0.22 | 4% | 0.20 | 3% |
| FD5 | Contender | 0.52 | 11% | 0.41 | 5% | 0.43 | 7% | 0.49 | 8% | 0.37 | 7% | 0.43 | 7% |

TABLE 62

Year 1—Weighted Mean (35 days)

| Variety | CP | ADF | aNDF | ADL | DM | IVTDMD | NDFD1 | RFQ | RFV | Milk/ton | Milk/acre |
|---|---|---|---|---|---|---|---|---|---|---|---|
| CW 054004 | 20.16 | 36.11 | 42.67 | 6.99 | 93.31 | 74.94 | 43.60 | 128.88 | 133.14 | 2,475.13 | 18,478.83 |
| 54H11 | 18.38 | 37.65 | 44.55 | 7.42 | 93.47 | 73.36 | 41.93 | 120.24 | 125.11 | 2,456.85 | 17,104.49 |
| 55V12 | 17.93 | 38.24 | 45.17 | 7.57 | 93.81 | 72.68 | 41.28 | 116.37 | 122.01 | 2,433.40 | 16,425.76 |
| A 30-06 | 19.77 | 37.51 | 43.93 | 7.25 | 93.31 | 74.30 | 43.32 | 123.38 | 127.21 | 2,416.66 | 16,338.70 |
| Ameristand 407TQ | 20.23 | 35.14 | 41.48 | 6.73 | 93.24 | 76.11 | 44.73 | 137.26 | 138.57 | 2,583.06 | 19,436.15 |
| eXclaim | 19.14 | 37.29 | 43.83 | 7.19 | 93.29 | 74.07 | 42.89 | 122.96 | 127.39 | 2,443.75 | 19,475.22 |
| PERFORMER | 20.53 | 34.64 | 40.78 | 6.67 | 93.44 | 76.16 | 44.15 | 138.97 | 141.83 | 2,593.38 | 19,521.05 |
| 243, STEALTH II | 19.06 | 36.29 | 43.15 | 7.17 | 93.76 | 74.66 | 43.73 | 129.14 | 131.38 | 2,538.32 | 18,838.53 |
| SHOWDOWN | 19.20 | 36.95 | 43.53 | 7.27 | 92.85 | 74.26 | 42.68 | 124.15 | 129.24 | 2,445.50 | 18,007.34 |
| Sundance II, Sansar | 19.03 | 36.08 | 42.70 | 6.99 | 92.80 | 74.98 | 43.48 | 129.40 | 132.62 | 2,528.71 | 19,304.30 |
| PGI 212, VR TOTAL | 20.07 | 35.78 | 42.00 | 6.82 | 93.21 | 75.79 | 44.57 | 134.13 | 135.51 | 2,549.59 | 18,861.52 |
| 5010 | 19.36 | 36.14 | 42.94 | 7.15 | 93.54 | 74.82 | 43.65 | 129.12 | 132.01 | 2,531.35 | 20,274.90 |
| PGI 557, LELIA | 19.53 | 35.67 | 42.36 | 6.99 | 93.44 | 74.89 | 43.33 | 130.55 | 135.19 | 2,529.84 | 18,286.30 |
| Summit | 19.76 | 36.07 | 42.68 | 7.05 | 93.50 | 75.16 | 43.86 | 130.12 | 132.75 | 2,530.58 | 19,267.66 |
| SolarGold, CORNERSTONE | 19.36 | 36.48 | 42.95 | 6.99 | 93.40 | 74.68 | 43.22 | 127.44 | 132.04 | 2,455.26 | 18,426.64 |
| Contender | 19.85 | 35.82 | 42.36 | 6.98 | 93.51 | 75.18 | 43.84 | 131.19 | 134.12 | 2,534.90 | 18,992.50 |
| Legend Extra | 19.96 | 36.27 | 42.73 | 6.93 | 93.59 | 75.23 | 44.32 | 130.75 | 132.49 | 2,515.35 | 18,546.97 |
| PGI 437, Tower ST | 18.56 | 37.78 | 44.65 | 7.45 | 92.88 | 73.17 | 41.51 | 117.26 | 124.46 | 2,389.39 | 16,263.57 |
| Exalt | 19.27 | 36.91 | 43.44 | 7.13 | 93.31 | 74.51 | 43.47 | 125.42 | 129.27 | 2,448.23 | 17,955.18 |
| PGI 459, Quest | 18.85 | 36.69 | 43.34 | 7.06 | 93.60 | 74.75 | 43.84 | 128.54 | 129.99 | 2,527.74 | 19,367.50 |
| HybriForce-400 | 19.16 | 36.91 | 43.55 | 7.17 | 93.62 | 74.49 | 43.24 | 125.29 | 129.01 | 2,466.22 | 17,835.05 |
| Rugged | 19.85 | 36.73 | 43.25 | 7.12 | 93.41 | 75.23 | 44.77 | 128.69 | 129.94 | 2,481.69 | 17,706.53 |
| TS 4006 | 20.31 | 36.11 | 42.35 | 6.99 | 93.33 | 75.51 | 44.24 | 131.29 | 134.22 | 2,486.31 | 17,184.46 |
| TS 4007 | 20.15 | 36.24 | 42.64 | 6.96 | 93.27 | 75.31 | 44.29 | 129.99 | 133.24 | 2,459.35 | 17,364.61 |
| TS 4010 | 19.15 | 37.07 | 43.74 | 7.16 | 93.29 | 74.43 | 43.38 | 124.55 | 128.23 | 2,451.02 | 16,937.50 |
| TS 4013 | 19.12 | 36.36 | 43.12 | 7.17 | 93.40 | 74.67 | 43.41 | 127.90 | 131.15 | 2,510.88 | 17,947.54 |
| TS 4027 | 18.89 | 37.62 | 44.39 | 7.34 | 92.92 | 73.82 | 42.70 | 121.28 | 125.60 | 2,429.87 | 17,505.82 |
| WL 319 HQ | 20.24 | 34.92 | 41.33 | 6.84 | 92.60 | 75.97 | 44.31 | 136.19 | 139.14 | 2,564.69 | 18,537.49 |
| Grand Mean | 19.43 | 36.43 | 43.03 | 7.09 | 93.34 | 74.76 | 43.48 | 128.07 | 131.54 | 2,495.13 | 18,237.26 |
| LSD (0.05) | 1.02 | 1.71 | 1.95 | 0.39 | 0.64 | 1.50 | 1.43 | 10.30 | 8.81 | 103.25 | 1,727.24 |
| C.V. (%) | 3.20 | 2.87 | 2.77 | 3.39 | 0.42 | 1.23 | 2.02 | 4.93 | 4.10 | 2.53 | 5.80 |
| R2 | 0.58 | 0.51 | 0.53 | 0.56 | 0.45 | 0.57 | 0.62 | 0.53 | 0.52 | 0.51 | 0.62 |

TABLE 63

| | | May | | June | | July | | Weighted Mean | |
|---|---|---|---|---|---|---|---|---|---|
| FD Group | Variety | ADL Adv. | % ADL Adv. | ADL Adv. | % ADL Adv. | ADL Adv. | % ADL Adv. | ADL Adv. | % ADL Adv. |
| FD2 | PGI 212, VR TOTAL | -0.11 | -2% | 0.03 | 0% | -0.60 | -9% | -0.17 | -3% |
| FD3 | eXclaim | 0.59 | 8% | 0.05 | 1% | -0.28 | -4% | 0.20 | 3% |
| FD3 | Legend Extra | 0.13 | 2% | -0.25 | -4% | -0.10 | -1% | -0.06 | -1% |
| FD3 | Rugged | 0.23 | 3% | 0.35 | 5% | -0.36 | -5% | 0.12 | 2% |
| FD3 | WL 319 HQ | 0.00 | 0% | -0.27 | -4% | -0.27 | -4% | -0.16 | -2% |
| FD4 | CW 054004 | 0.00 | 0% | 0.00 | 0% | 0.00 | 0% | 0.00 | 0% |
| FD4 | 54H11 | 0.70 | 10% | -0.01 | 0% | 0.63 | 8% | 0.43 | 6% |
| FD4 | A 30-06 | 0.19 | 3% | 0.45 | 6% | 0.16 | 2% | 0.25 | 3% |

TABLE 63-continued

| | | May | | June | | July | | Weighted Mean | |
|---|---|---|---|---|---|---|---|---|---|
| FD Group | Variety | ADL Adv. | % ADL Adv. | ADL Adv. | % ADL Adv. | ADL Adv. | % ADL Adv. | ADL Adv. | % ADL Adv. |
| FD4 | Ameristand 407TQ | −0.18 | −3% | −0.27 | −4% | −0.37 | −5% | −0.26 | −4% |
| FD4 | PERFORMER | −0.29 | −4% | −0.32 | −5% | −0.40 | −6% | −0.32 | −5% |
| FD4 | Sundance II, Sansar | 0.30 | 4% | −0.19 | −3% | −0.22 | −3% | 0.00 | 0% |
| FD4 | Summit | 0.24 | 4% | −0.03 | 0% | −0.16 | −2% | 0.05 | 1% |
| FD4 | SolarGold, CORNERSTONE | 0.00 | 0% | 0.15 | 2% | −0.22 | −3% | −0.01 | 0% |
| FD4 | PGI 437, Tower ST | 0.58 | 8% | 0.67 | 8% | −0.04 | −1% | 0.46 | 6% |
| FD4 | Exalt | 0.21 | 3% | 0.18 | 2% | −0.04 | −1% | 0.14 | 2% |
| FD4 | PGI 459, Quest | 0.06 | 1% | 0.01 | 0% | 0.16 | 2% | 0.07 | 1% |
| FD4 | HybriForce-400 | 0.09 | 1% | 0.38 | 5% | 0.06 | 1% | 0.18 | 2% |
| FD4 | TS 4006 | 0.02 | 0% | 0.00 | 0% | −0.04 | −1% | −0.01 | 0% |
| FD4 | TS 4007 | −0.04 | −1% | −0.11 | −2% | 0.21 | 3% | −0.03 | 0% |
| FD4 | TS 4010 | 0.57 | 8% | −0.21 | −3% | −0.01 | 0% | 0.17 | 2% |
| FD4 | TS 4013 | 0.11 | 2% | 0.31 | 4% | 0.11 | 2% | 0.17 | 2% |
| FD4 | TS 4027 | 0.35 | 5% | 0.32 | 4% | 0.41 | 5% | 0.34 | 5% |
| FD5 | 55V12 | 0.75 | 10% | 0.63 | 8% | 0.18 | 2% | 0.57 | 8% |
| FD5 | 243, STEALTH II | 0.19 | 3% | 0.28 | 4% | 0.03 | 0% | 0.18 | 2% |
| FD5 | SHOWDOWN | 0.25 | 4% | 0.33 | 4% | 0.22 | 3% | 0.27 | 4% |
| FD5 | 5010 | 0.42 | 6% | 0.11 | 2% | −0.26 | −4% | 0.16 | 2% |
| FD5 | PGI 557, LELIA | −0.12 | −2% | 0.37 | 5% | −0.41 | −6% | 0.00 | 0% |
| FD5 | Contender | 0.24 | 3% | −0.14 | −2% | −0.26 | −4% | −0.01 | 0% |

TABLE 64

Year 1—Weighted Mean (28 days)

| Variety | CP | ADF | aNDF | ADL | DM | IVTDMD | NDFD1 | RFQ | RFV | Milk/ton | Milk/acre |
|---|---|---|---|---|---|---|---|---|---|---|---|
| CW 054004 | 23.36 | 29.88 | 34.86 | 5.90 | 93.80 | 81.66 | 48.71 | 190.42 | 178.65 | 3,121.59 | 25,765.68 |
| 54H11 | 22.43 | 31.40 | 36.43 | 6.28 | 93.97 | 80.19 | 47.65 | 176.88 | 166.79 | 3,036.49 | 21,633.38 |
| PGI 215, Velvet | 23.29 | 30.09 | 35.12 | 6.00 | 94.05 | 81.26 | 48.27 | 186.27 | 175.44 | 3,103.00 | 24,961.91 |
| eXclaim | 22.90 | 30.15 | 35.02 | 5.84 | 94.00 | 81.74 | 49.39 | 190.49 | 176.67 | 3,127.67 | 26,732.55 |
| PERFORMER | 22.83 | 30.27 | 35.13 | 5.97 | 93.89 | 81.29 | 48.34 | 187.46 | 176.19 | 3,105.11 | 26,565.26 |
| Optimus | 22.96 | 30.48 | 35.39 | 6.11 | 93.83 | 81.10 | 48.19 | 184.45 | 173.35 | 3,090.23 | 25,082.05 |
| ForageGold | 22.59 | 30.85 | 35.96 | 6.18 | 93.91 | 80.52 | 47.63 | 179.51 | 169.91 | 3,056.99 | 24,751.79 |
| 243, STEALTH II | 22.54 | 30.97 | 36.27 | 6.25 | 93.73 | 80.21 | 47.12 | 177.18 | 169.00 | 3,032.03 | 23,251.72 |
| SHOWDOWN | 22.86 | 30.63 | 35.77 | 6.18 | 93.95 | 80.50 | 47.18 | 180.43 | 172.11 | 3,054.92 | 24,891.95 |
| 5010 | 22.51 | 30.86 | 35.98 | 6.23 | 93.75 | 80.28 | 47.41 | 178.05 | 168.93 | 3,053.33 | 24,985.96 |
| Summit | 22.99 | 30.60 | 35.56 | 6.09 | 93.94 | 80.79 | 48.02 | 183.24 | 172.66 | 3,079.29 | 26,535.01 |
| WinterKing III | 22.72 | 30.53 | 35.55 | 6.15 | 93.89 | 80.65 | 47.75 | 183.69 | 173.80 | 3,074.60 | 25,377.20 |
| Contender | 22.70 | 30.18 | 35.28 | 6.14 | 93.92 | 80.77 | 47.39 | 183.12 | 174.37 | 3,083.33 | 26,557.69 |
| Althea | 21.90 | 31.40 | 36.58 | 6.40 | 93.65 | 80.11 | 47.59 | 176.31 | 166.53 | 3,029.17 | 27,593.61 |
| Keystone II | 23.29 | 30.30 | 35.09 | 5.99 | 93.97 | 81.26 | 48.24 | 187.38 | 176.22 | 3,102.27 | 25,101.71 |
| Barricade SLT | 22.50 | 30.77 | 35.93 | 6.24 | 93.85 | 80.34 | 47.20 | 179.30 | 170.77 | 3,050.03 | 24,439.73 |
| PGI 529, DOMINATOR | 22.27 | 31.16 | 36.42 | 6.32 | 93.86 | 79.94 | 46.71 | 175.12 | 167.67 | 3,019.81 | 26,175.35 |
| Pillar ST | 23.08 | 30.98 | 36.15 | 6.35 | 93.78 | 80.20 | 47.46 | 178.30 | 169.17 | 3,042.28 | 24,501.36 |
| Adrenalin | 23.22 | 30.01 | 35.05 | 6.00 | 93.92 | 81.26 | 48.39 | 187.39 | 176.35 | 3,108.40 | 23,331.77 |
| Exalt | 23.16 | 30.30 | 35.31 | 6.10 | 93.76 | 80.97 | 47.69 | 183.86 | 174.26 | 3,084.32 | 25,012.05 |
| PGI 459, Qwest | 22.68 | 30.76 | 35.96 | 6.22 | 93.97 | 80.32 | 47.07 | 178.67 | 170.57 | 3,045.84 | 23,345.01 |
| WinterKing II Megan | 22.83 | 30.52 | 35.70 | 6.03 | 94.02 | 80.98 | 48.30 | 183.63 | 172.69 | 3,077.73 | 23,653.21 |
| HybriForce-400 | 22.87 | 30.93 | 36.01 | 6.21 | 93.95 | 80.69 | 48.03 | 180.28 | 169.65 | 3,059.90 | 23,009.69 |
| WL 319 HQ | 24.16 | 28.85 | 33.53 | 5.72 | 93.71 | 82.39 | 48.91 | 199.36 | 187.18 | 3,181.33 | 24,079.97 |
| Grand Mean | 22.93 | 30.50 | 35.53 | 6.11 | 93.88 | 80.88 | 47.98 | 183.64 | 173.27 | 3,080.10 | 24,960.61 |
| LSD (0.05) | 0.56 | 1.11 | 1.13 | 0.26 | 0.29 | 1.00 | 1.07 | 9.37 | 8.21 | 62.53 | 2,319.27 |
| C.V. (%) | 1.51 | 2.23 | 1.95 | 2.62 | 0.19 | 0.76 | 1.36 | 3.13 | 2.90 | 1.24 | 5.69 |
| R2 | 0.74 | 0.59 | 0.64 | 0.66 | 0.38 | 0.63 | 0.59 | 0.63 | 0.61 | 0.64 | 0.67 |

TABLE 65

| | | Cut 1 | | Cut 2 | | Cut 3 | | Cut 4 | | Cut 5 | | Weighted Average | |
|---|---|---|---|---|---|---|---|---|---|---|---|---|---|
| FD Group | Variety | ADL Adv. | % ADL Adv. | ADL Adv. | ADL Adv. | ADL Adv. | ADL Adv. | ADL Adv. | ADL Adv. | ADL Adv. | ADL Adv. | ADL Adv. | ADL Adv. |
| FD2 | PGI 215, Velvet | 0.13 | 2% | 0.05 | 1% | −0.16 | −2% | 0.30 | 4% | 0.04 | 1% | 0.10 | 2% |
| FD3 | eXclaim | −0.22 | −4% | −0.10 | −2% | −0.01 | 0% | 0.45 | 6% | −0.06 | −1% | −0.06 | −1% |

TABLE 65-continued

| | | Cut 1 | | Cut 2 | | Cut 3 | | Cut 4 | | Cut 5 | | Weighted Average | |
|---|---|---|---|---|---|---|---|---|---|---|---|---|---|
| FD Group | Variety | ADL Adv. | % ADL Adv. | ADL Adv. | ADL Adv. | ADL Adv. | ADL Adv. | ADL Adv. | ADL Adv. | ADL Adv. | ADL Adv. | ADL Adv. | ADL Adv. |
| FD3 | Keystone II | −0.29 | −5% | 0.30 | 6% | −0.12 | −2% | 0.76 | 10% | 0.16 | 2% | 0.09 | 2% |
| FD3 | WL 319 HQ | −0.31 | −6% | −0.10 | −2% | −0.45 | −7% | 0.62 | 8% | −0.62 | −11% | −0.18 | −3% |
| FD4 | CW 054004 | 0.00 | 0% | 0.00 | 0% | 0.00 | 0% | 0.00 | 0% | 0.00 | 0% | 0.00 | 0% |
| FD4 | 54H11 | 0.31 | 5% | 0.38 | 8% | 0.31 | 4% | 0.64 | 9% | 0.17 | 3% | 0.38 | 6% |
| FD4 | PERFORMER | −0.02 | 0% | 0.24 | 5% | −0.25 | −4% | 0.26 | 4% | 0.06 | 1% | 0.07 | 1% |
| FD4 | Optimus | 0.39 | 6% | 0.06 | 1% | 0.11 | 2% | 0.42 | 6% | −0.01 | 0% | 0.21 | 3% |
| FD4 | ForageGold | 0.34 | 6% | 0.38 | 8% | 0.11 | 2% | 0.37 | 5% | 0.45 | 7% | 0.28 | 5% |
| FD4 | Summit | 0.12 | 2% | 0.30 | 6% | −0.12 | −2% | 0.47 | 6% | 0.16 | 2% | 0.19 | 3% |
| FD4 | WinterKing III | −0.02 | 0% | 0.11 | 2% | 0.13 | 2% | 1.08 | 14% | 0.28 | 4% | 0.25 | 4% |
| FD4 | Barricade SLT | 0.51 | 8% | 0.16 | 3% | 0.24 | 3% | 0.45 | 6% | 0.42 | 6% | 0.34 | 5% |
| FD4 | Pillar ST | 0.52 | 8% | 0.25 | 5% | 0.21 | 3% | 0.79 | 10% | 0.41 | 6% | 0.45 | 7% |
| FD4 | Adrenalin | −0.03 | −1% | 0.33 | 7% | −0.01 | 0% | 0.21 | 3% | 0.45 | 7% | 0.10 | 2% |
| FD4 | Exalt | 0.10 | 2% | 0.41 | 8% | −0.09 | −1% | 0.54 | 7% | 0.04 | 1% | 0.20 | 3% |
| FD4 | PGI 459, Qwest | 0.24 | 4% | 0.57 | 11% | 0.05 | 1% | 0.48 | 7% | 0.57 | 8% | 0.32 | 5% |
| FD4 | WinterKing II, Megan | 0.21 | 4% | −0.03 | −1% | −0.02 | 0% | 0.43 | 6% | 0.14 | 2% | 0.13 | 2% |
| FD4 | HybriForce-400 | 0.17 | 3% | 0.46 | 9% | −0.11 | −2% | 0.79 | 10% | 0.26 | 4% | 0.31 | 5% |
| FD5 | 243, STEALTH II | 0.13 | 2% | 0.49 | 9% | 0.36 | 5% | 0.76 | 10% | 0.25 | 4% | 0.35 | 6% |
| FD5 | SHOWDOWN | 0.17 | 3% | 0.24 | 5% | −0.02 | 0% | 0.73 | 10% | 0.74 | 10% | 0.28 | 4% |
| FD5 | 5010 | 0.35 | 6% | 0.80 | 15% | −0.01 | 0% | −0.04 | −1% | 0.31 | 5% | 0.33 | 5% |
| FD5 | Contender | 0.45 | 7% | 0.34 | 7% | 0.18 | 3% | −0.29 | −4% | 0.43 | 6% | 0.24 | 4% |
| FD5 | Althea | 0.40 | 7% | 0.55 | 10% | 0.40 | 6% | 0.99 | 13% | 0.17 | 3% | 0.50 | 8% |
| FD5 | PGI 529, DOMINATOR | 0.53 | 9% | 0.40 | 8% | 0.15 | 2% | 0.70 | 9% | 0.03 | 0% | 0.42 | 7% |

TABLE 66

Year 1—Weighted Mean (35 days)

| Variety | CP | ADF | aNDF | ADL | DM | IVTDMD | NDFD1 | RFQ | RFV | Milk/ton | Milk/acre |
|---|---|---|---|---|---|---|---|---|---|---|---|
| CW 054004 | 20.91 | 33.48 | 39.03 | 6.68 | 94.72 | 78.77 | 47.15 | 152.45 | 151.08 | 2,638.83 | 18,204.44 |
| 54H11 | 18.96 | 37.15 | 43.22 | 7.60 | 94.74 | 74.81 | 43.39 | 126.43 | 129.47 | 2,474.99 | 15,662.35 |
| PGI 215, Velvet | 20.92 | 33.35 | 38.91 | 6.68 | 94.55 | 78.64 | 46.72 | 151.90 | 151.38 | 2,648.03 | 17,779.05 |
| eXclaim | 20.65 | 33.19 | 38.80 | 6.53 | 94.79 | 79.02 | 47.19 | 154.73 | 152.22 | 2,703.62 | 20,155.88 |
| PERFORMER | 20.81 | 33.50 | 38.92 | 6.70 | 94.62 | 78.76 | 46.50 | 151.05 | 151.19 | 2,629.36 | 17,426.15 |
| Optimus | 20.26 | 34.13 | 39.92 | 6.89 | 94.60 | 77.95 | 45.90 | 146.34 | 146.55 | 2,621.86 | 18,850.73 |
| ForageGold | 20.29 | 34.10 | 39.92 | 6.80 | 94.61 | 78.03 | 46.35 | 147.33 | 146.35 | 2,637.58 | 18,498.69 |
| 243, STEALTH II | 20.38 | 33.64 | 39.59 | 6.83 | 94.30 | 78.22 | 46.26 | 149.25 | 148.60 | 2,663.89 | 18,056.85 |
| SHOWDOWN | 19.89 | 35.21 | 40.98 | 7.06 | 94.61 | 76.90 | 45.60 | 138.99 | 140.47 | 2,522.59 | 16,936.60 |
| 5010 | 20.32 | 34.37 | 40.08 | 6.95 | 94.69 | 77.24 | 45.20 | 143.52 | 145.46 | 2,586.58 | 18,028.32 |
| Summit | 20.32 | 33.41 | 39.04 | 6.61 | 94.52 | 78.43 | 46.50 | 150.65 | 151.01 | 2,628.97 | 17,745.69 |
| WinterKing III | 20.40 | 33.80 | 39.58 | 6.83 | 94.68 | 78.21 | 46.68 | 149.04 | 148.65 | 2,617.81 | 16,756.27 |
| Contender | 20.31 | 34.23 | 39.72 | 7.02 | 94.62 | 77.58 | 44.92 | 144.50 | 146.96 | 2,588.41 | 18,454.57 |
| Althea | 19.86 | 35.26 | 41.08 | 7.11 | 94.85 | 77.07 | 45.62 | 140.26 | 140.67 | 2,557.87 | 17,780.77 |
| Keystone II | 20.65 | 33.45 | 39.02 | 6.53 | 94.50 | 79.05 | 47.44 | 153.22 | 150.72 | 2,670.47 | 18,246.11 |
| Barricade SLT | 19.77 | 35.43 | 41.22 | 7.21 | 94.81 | 76.80 | 45.29 | 138.58 | 139.00 | 2,563.15 | 17,381.19 |
| PGI 529, DOMINATOR | 20.46 | 33.41 | 39.20 | 6.67 | 94.33 | 78.42 | 46.27 | 150.62 | 150.29 | 2,669.67 | 19,712.72 |
| Pillar ST | 19.69 | 35.51 | 41.24 | 7.41 | 94.81 | 76.48 | 44.58 | 135.78 | 138.94 | 2,500.31 | 16,733.07 |
| Adrenalin | 20.57 | 33.86 | 39.63 | 6.84 | 94.38 | 78.14 | 46.08 | 147.72 | 147.67 | 2,636.82 | 16,897.40 |
| Exalt | 20.48 | 34.15 | 39.73 | 6.73 | 94.48 | 78.31 | 47.00 | 147.38 | 146.43 | 2,597.86 | 16,721.69 |
| PGI 459, Qwest | 19.59 | 35.38 | 41.22 | 7.09 | 94.82 | 76.94 | 45.40 | 139.38 | 140.22 | 2,538.48 | 17,065.25 |
| WinterKing II, Megan | 20.61 | 33.94 | 39.65 | 6.71 | 94.69 | 78.05 | 46.33 | 147.49 | 147.83 | 2,602.48 | 16,532.33 |
| HybriForce-400 | 20.08 | 35.03 | 40.80 | 6.84 | 94.66 | 77.44 | 46.39 | 143.12 | 141.60 | 2,592.12 | 16,910.72 |
| WL 319 HQ | 20.94 | 34.20 | 39.66 | 6.90 | 94.41 | 78.22 | 46.32 | 146.98 | 146.87 | 2,601.26 | 17,136.06 |
| Grand Mean | 20.32 | 34.22 | 39.91 | 6.87 | 94.65 | 77.90 | 46.16 | 146.19 | 146.25 | 2,604.39 | 17,479.49 |
| LSD (0.05) | 0.88 | 1.72 | 1.81 | 0.37 | 0.36 | 1.39 | 0.99 | 11.10 | 9.83 | 129.54 | 1,464.68 |
| C.V. (%) | 2.65 | 3.09 | 2.77 | 3.26 | 0.23 | 1.09 | 1.32 | 4.65 | 4.12 | 3.05 | 5.13 |
| R2 | 0.57 | 0.56 | 0.59 | 0.69 | 0.39 | 0.66 | 0.79 | 0.59 | 0.56 | 0.47 | 0.64 |

TABLE 67

| FD Group | Variety | May ADL Adv. | May % ADL Adv. | June ADL Adv. | June % ADL Adv. | July ADL Adv. | July % ADL Adv. | Weighted Mean ADL Adv. | Weighted Mean % ADL Adv. |
|---|---|---|---|---|---|---|---|---|---|
| FD2 | PGI 215, Velvet | 0.12 | 2% | 0.25 | 4% | −0.63 | −8% | 0.00 | 0% |
| FD3 | eXclaim | 0.32 | 5% | −0.26 | −4% | −0.88 | −12% | −0.15 | −2% |
| FD3 | Keystone II | 0.16 | 2% | −0.06 | −1% | −0.88 | −12% | −0.15 | −2% |
| FD3 | WL 319 HQ | 0.45 | 7% | 0.22 | 4% | −0.26 | −3% | 0.22 | 3% |
| FD4 | CW 054004 | 0.00 | 0% | 0.00 | 0% | 0.00 | 0% | 0.00 | 0% |
| FD4 | 54H11 | 1.18 | 16% | 1.34 | 18% | −0.09 | −1% | 0.92 | 12% |
| FD4 | PERFORMER | 0.14 | 2% | 0.14 | 2% | −0.45 | −6% | 0.02 | 0% |
| FD4 | Optimus | 0.38 | 6% | 0.46 | 7% | −0.51 | −7% | 0.21 | 3% |
| FD4 | ForageGold | 0.43 | 6% | 0.30 | 5% | −0.65 | −9% | 0.12 | 2% |
| FD4 | Summit | 0.29 | 4% | −0.18 | −3% | −0.51 | −7% | −0.07 | −1% |
| FD4 | WinterKing III | 0.37 | 6% | 0.22 | 3% | −0.40 | −5% | 0.15 | 2% |
| FD4 | Barricade SLT | 0.55 | 8% | 1.13 | 16% | −0.33 | −4% | 0.53 | 7% |
| FD4 | Pillar ST | 0.79 | 11% | 1.14 | 16% | 0.06 | 1% | 0.73 | 10% |
| FD4 | Adrenalin | 0.42 | 6% | 0.22 | 3% | −0.40 | −5% | 0.16 | 2% |
| FD4 | Exalt | 0.29 | 4% | 0.25 | 4% | −0.73 | −10% | 0.05 | 1% |
| FD4 | PGI 459, Qwest | 0.34 | 5% | 0.57 | 9% | 0.19 | 2% | 0.41 | 6% |
| FD4 | WinterKing II, Megan | 0.02 | 0% | 0.60 | 9% | −0.77 | −11% | 0.03 | 0% |
| FD4 | HybriForce-400 | 0.20 | 3% | 0.57 | 8% | −0.47 | −6% | 0.16 | 2% |
| FD5 | 243, STEALTH II | 0.47 | 7% | 0.15 | 2% | −0.41 | −5% | 0.15 | 2% |
| FD5 | SHOWDOWN | 0.46 | 7% | 0.66 | 10% | −0.07 | −1% | 0.38 | 5% |
| FD5 | 5010 | 0.29 | 4% | 0.61 | 9% | −0.40 | −5% | 0.27 | 4% |
| FD5 | Contender | 0.31 | 5% | 0.55 | 8% | −0.10 | −1% | 0.34 | 5% |
| FD5 | Althea | 0.58 | 8% | 0.59 | 9% | −0.14 | −2% | 0.43 | 6% |
| FD5 | PGI 529, DOMINATOR | 0.60 | 9% | −0.16 | −3% | −0.76 | −10% | −0.01 | 0% |

Example 11

CW093009

The forage quality of CW093009 was compared to various commercially available alfalfa varieties using the methods described in Example 1. CW093009 and the commercially available alfalfa varieties were harvested in May, June and July of Year 1. See Tables 68-70. The weighted mean for the three cuts is shown in Table 71.

TABLE 68

| | May Year 1—Cut 1 | | | | | | | | | | |
|---|---|---|---|---|---|---|---|---|---|---|---|
| Variety | CP | ADF | aNDF | ADL | DM | IVTDMD | NDFD1 | RFQ | RFV | Milk/ton | Milk/acre |
| CW 093009 | 23.63 | 30.45 | 35.82 | 5.16 | 93.63 | 83.48 | 54.40 | 192.19 | 169.35 | 3,101.95 | 9,417.35 |
| 54V46 | 21.92 | 33.36 | 39.26 | 5.89 | 93.69 | 80.83 | 52.56 | 170.30 | 149.14 | 2,992.43 | 7,310.41 |
| 55V12 | 20.22 | 35.09 | 41.85 | 6.44 | 94.65 | 78.28 | 49.03 | 152.12 | 137.08 | 2,914.21 | 7,642.62 |
| PGI 212, VR TOTAL | 23.91 | 31.42 | 36.93 | 5.50 | 93.97 | 82.28 | 52.91 | 184.08 | 163.63 | 3,063.16 | 7,595.76 |
| Assalt ST | 22.80 | 31.95 | 37.68 | 5.75 | 94.43 | 81.82 | 52.50 | 179.61 | 158.50 | 3,074.26 | 7,744.04 |
| PGI 557, Lelia | 24.26 | 30.44 | 35.64 | 5.46 | 93.71 | 83.01 | 53.13 | 190.63 | 170.59 | 3,091.35 | 8,035.97 |
| StarGold | 22.35 | 32.74 | 38.44 | 5.94 | 93.27 | 80.60 | 50.76 | 170.47 | 153.58 | 2,998.59 | 7,882.31 |
| Sundance III, PERFECTION | 22.60 | 31.75 | 37.91 | 5.68 | 94.27 | 81.80 | 52.43 | 178.42 | 157.47 | 3,086.29 | 8,974.81 |
| PGI 437, Tower ST | 22.03 | 32.91 | 39.02 | 5.93 | 93.89 | 80.69 | 51.86 | 171.38 | 151.24 | 3,029.57 | 7,672.02 |
| A 4330 | 22.62 | 31.92 | 38.00 | 5.66 | 94.04 | 81.80 | 52.79 | 177.86 | 156.97 | 3,054.26 | 8,308.35 |
| A 5225 | 22.65 | 32.02 | 38.09 | 5.76 | 94.41 | 81.28 | 51.97 | 175.58 | 156.19 | 3,048.14 | 7,946.55 |
| Pillar, Actis | 22.25 | 33.37 | 39.30 | 6.00 | 93.62 | 80.69 | 51.73 | 168.60 | 149.40 | 2,980.98 | 8,104.33 |
| HybriForce-2400 | 22.92 | 31.97 | 37.86 | 5.70 | 94.38 | 82.26 | 53.36 | 179.89 | 157.31 | 3,069.76 | 8,236.51 |
| HybriForce-400 | 22.30 | 32.48 | 38.73 | 5.69 | 94.41 | 81.12 | 52.30 | 173.30 | 152.81 | 3,038.46 | 7,339.63 |
| WL 319 HQ | 25.07 | 29.43 | 34.81 | 5.25 | 94.47 | 84.13 | 54.46 | 199.07 | 176.42 | 3,152.33 | 8,425.98 |
| Grand Mean | 22.78 | 31.91 | 37.68 | 5.72 | 93.93 | 81.72 | 52.26 | 178.53 | 158.62 | 3,053.68 | 7,954.13 |
| LSD (0.05) | 1.40 | 1.89 | 2.34 | 0.41 | 1.25 | 1.90 | 2.54 | 15.17 | 13.48 | 105.89 | 794.85 |
| C.V. (%) | 3.78 | 3.63 | 3.81 | 4.42 | 0.82 | 1.42 | 2.97 | 5.20 | 5.20 | 2.12 | 6.12 |
| R2 | 0.61 | 0.62 | 0.61 | 0.68 | 0.39 | 0.62 | 0.54 | 0.61 | 0.61 | 0.50 | 0.70 |

TABLE 69

June Year 1—Cut 2

| Variety | CP | ADF | aNDF | ADL | DM | IVTDMD | NDFD1 | RFQ | RFV | Milk/ton | Milk/acre |
|---|---|---|---|---|---|---|---|---|---|---|---|
| CW 093009 | 22.33 | 28.84 | 34.03 | 5.04 | 92.96 | 83.42 | 50.51 | 197.17 | 181.74 | 3,192.83 | 6,694.41 |
| 54V46 | 21.74 | 30.23 | 35.47 | 5.52 | 92.62 | 81.93 | 48.87 | 184.76 | 172.02 | 3,122.24 | 5,342.83 |
| 55V12 | 22.01 | 31.03 | 36.64 | 5.67 | 93.67 | 81.30 | 48.51 | 176.96 | 164.33 | 3,092.54 | 5,355.42 |
| PGI 212, VR TOTAL | 22.89 | 27.71 | 32.63 | 4.85 | 92.97 | 83.93 | 50.36 | 207.53 | 192.93 | 3,245.79 | 6,133.17 |
| Assalt ST | 21.70 | 30.37 | 35.79 | 5.54 | 92.79 | 81.25 | 47.37 | 181.51 | 171.90 | 3,106.51 | 5,427.02 |
| PGI 557, Lelia | 20.65 | 31.75 | 37.23 | 5.87 | 92.94 | 80.05 | 46.92 | 171.01 | 160.36 | 3,079.97 | 5,680.61 |
| StarGold | 22.16 | 28.45 | 33.87 | 5.20 | 92.79 | 82.97 | 49.19 | 197.39 | 185.33 | 3,199.07 | 6,229.52 |
| Sundance III, PERFECTION | 20.91 | 29.76 | 35.24 | 5.31 | 93.42 | 81.74 | 48.68 | 187.41 | 173.76 | 3,187.91 | 6,729.31 |
| PGI 437, Tower ST | 20.79 | 32.05 | 37.61 | 5.93 | 93.00 | 79.92 | 46.85 | 168.84 | 158.95 | 3,041.35 | 5,799.24 |
| A 4330 | 20.77 | 29.90 | 35.45 | 5.27 | 93.28 | 82.04 | 49.11 | 186.84 | 172.52 | 3,177.44 | 6,167.91 |
| A 5225 | 20.70 | 32.21 | 38.06 | 5.98 | 92.89 | 79.60 | 46.67 | 165.22 | 156.13 | 3,018.39 | 5,385.03 |
| Pillar, Actis | 20.13 | 34.10 | 39.93 | 6.37 | 92.76 | 78.32 | 46.33 | 154.62 | 145.52 | 2,929.68 | 5,795.61 |
| HybriForce-2400 | 20.64 | 30.73 | 36.50 | 5.77 | 92.90 | 80.83 | 48.15 | 177.61 | 165.61 | 3,111.33 | 5,506.17 |
| HybriForce-400 | 22.43 | 29.72 | 35.05 | 5.48 | 93.23 | 82.11 | 48.73 | 187.35 | 175.24 | 3,141.28 | 5,126.78 |
| WL 319 HQ | 21.72 | 29.30 | 34.63 | 5.23 | 93.20 | 82.24 | 48.99 | 192.78 | 178.88 | 3,203.76 | 5,409.85 |
| Grand Mean | 21.33 | 30.51 | 35.97 | 5.59 | 93.09 | 81.35 | 48.29 | 181.80 | 169.55 | 3,125.07 | 5,838.16 |
| LSD (0.05) | 1.86 | 3.35 | 3.54 | 0.76 | 0.87 | 2.66 | 2.16 | 26.57 | 25.15 | 157.73 | 595.39 |
| C.V. (%) | 5.33 | 6.73 | 6.03 | 8.34 | 0.57 | 2.00 | 2.74 | 8.95 | 9.08 | 3.09 | 6.25 |
| R2 | 0.42 | 0.43 | 0.46 | 0.49 | 0.39 | 0.50 | 0.57 | 0.47 | 0.43 | 0.48 | 0.64 |

TABLE 70

July Year 1—Cut 3

| Variety | CP | ADF | aNDF | ADL | DM | IVTDMD | NDFD1 | RFQ | RFV | Milk/ton | Milk/acre |
|---|---|---|---|---|---|---|---|---|---|---|---|
| CW 093009 | 21.94 | 32.11 | 37.60 | 5.84 | 92.39 | 79.09 | 44.65 | 160.93 | 158.27 | 2,929.22 | 5,714.51 |
| 54V46 | 21.90 | 32.34 | 37.96 | 5.81 | 91.91 | 78.77 | 43.95 | 157.94 | 156.45 | 2,918.25 | 4,903.48 |
| 55V12 | 21.87 | 30.99 | 36.68 | 5.78 | 92.48 | 79.65 | 44.43 | 166.82 | 164.96 | 2,986.28 | 5,215.41 |
| PGI 212, VR TOTAL | 23.38 | 29.28 | 34.22 | 5.24 | 91.90 | 81.36 | 45.07 | 182.60 | 180.03 | 3,077.88 | 5,227.50 |
| Assalt ST | 21.30 | 33.26 | 39.01 | 6.32 | 92.51 | 77.28 | 41.50 | 148.65 | 150.58 | 2,891.18 | 4,796.83 |
| PGI 557, Lelia | 22.70 | 30.55 | 35.99 | 5.55 | 92.30 | 80.00 | 44.50 | 170.39 | 168.36 | 3,013.04 | 5,493.98 |
| StarGold | 22.98 | 29.17 | 34.40 | 5.36 | 92.43 | 81.40 | 46.22 | 186.54 | 182.73 | 3,070.15 | 5,875.36 |
| Sundance III, PERFECTION | 21.12 | 31.80 | 37.62 | 6.04 | 92.61 | 78.90 | 43.86 | 161.34 | 159.21 | 2,980.77 | 6,047.63 |
| PGI 437, Tower ST | 21.18 | 34.06 | 40.06 | 6.48 | 92.56 | 76.99 | 42.56 | 145.00 | 144.84 | 2,851.62 | 4,916.47 |
| A 4330 | 21.95 | 32.16 | 37.90 | 5.88 | 92.40 | 78.92 | 44.90 | 160.01 | 157.19 | 2,918.76 | 5,411.03 |
| A 5225 | 22.20 | 31.59 | 37.40 | 5.91 | 92.96 | 78.96 | 43.81 | 161.84 | 160.10 | 2,982.12 | 5,449.70 |
| Pillar, Actis | 21.18 | 33.05 | 38.94 | 5.94 | 92.62 | 78.49 | 45.28 | 156.10 | 150.87 | 2,922.86 | 5,602.97 |
| HybriForce-2400 | 21.99 | 31.02 | 36.92 | 5.84 | 92.28 | 79.47 | 44.13 | 163.98 | 163.45 | 2,959.14 | 5,062.15 |
| HybriForce-400 | 22.62 | 30.39 | 36.09 | 5.52 | 93.16 | 80.36 | 46.14 | 173.71 | 168.34 | 3,038.01 | 4,680.32 |
| WL 319 HQ | 23.00 | 28.61 | 34.05 | 5.16 | 92.54 | 81.70 | 46.07 | 185.93 | 182.74 | 3,087.43 | 5,033.97 |
| Grand Mean | 21.85 | 31.66 | 37.32 | 5.84 | 92.55 | 79.30 | 44.62 | 163.63 | 160.88 | 2,963.65 | 5,311.46 |
| LSD (0.05) | 1.53 | 2.65 | 2.99 | 0.61 | 0.87 | 2.30 | 2.16 | 20.90 | 19.05 | 129.19 | 507.46 |
| C.V. (%) | 4.29 | 5.12 | 4.90 | 6.39 | 0.58 | 1.77 | 2.97 | 7.82 | 7.25 | 2.67 | 5.85 |
| R2 | 0.53 | 0.49 | 0.50 | 0.51 | 0.34 | 0.51 | 0.56 | 0.49 | 0.49 | 0.46 | 0.74 |

TABLE 71

Year 1—Weighted Mean

| Variety | CP | ADF | aNDF | ADL | DM | IVTDMD | NDFD1 | RFQ | RFV | Milk/ton | Milk/acre |
|---|---|---|---|---|---|---|---|---|---|---|---|
| CW 093009 | 22.77 | 30.41 | 35.76 | 5.31 | 93.10 | 82.27 | 50.59 | 185.19 | 170.06 | 3,082.24 | 21,826.27 |
| 54V46 | 21.87 | 32.14 | 37.76 | 5.76 | 92.86 | 80.56 | 49.00 | 171.01 | 158.00 | 3,009.39 | 17,556.72 |
| 55V12 | 21.21 | 32.76 | 38.88 | 6.03 | 93.76 | 79.54 | 47.58 | 163.48 | 152.86 | 2,986.23 | 18,213.46 |
| PGI 212, VR TOTAL | 23.43 | 29.66 | 34.85 | 5.22 | 93.08 | 82.53 | 49.90 | 190.94 | 177.35 | 3,124.30 | 18,956.43 |
| Assalt ST | 22.06 | 31.85 | 37.49 | 5.85 | 93.41 | 80.38 | 47.91 | 171.52 | 160.25 | 3,032.71 | 17,967.90 |
| PGI 557, Lelia | 22.75 | 30.86 | 36.21 | 5.61 | 93.07 | 81.26 | 48.79 | 178.95 | 166.91 | 3,065.16 | 19,210.57 |
| StarGold | 22.45 | 30.47 | 35.96 | 5.56 | 92.89 | 81.49 | 48.91 | 182.67 | 171.09 | 3,077.40 | 19,987.19 |
| Sundance III, PERFECTION | 21.66 | 31.17 | 37.03 | 5.67 | 93.54 | 80.95 | 48.84 | 176.22 | 162.86 | 3,086.38 | 21,751.75 |
| PGI 437, Tower ST | 21.40 | 32.97 | 38.88 | 6.09 | 93.25 | 79.42 | 47.72 | 163.24 | 151.81 | 2,984.40 | 18,387.73 |
| A 4330 | 21.88 | 31.39 | 37.21 | 5.61 | 93.35 | 81.05 | 49.45 | 175.45 | 161.66 | 3,052.27 | 19,887.29 |

TABLE 71-continued

| | Year 1—Weighted Mean | | | | | | | | | | |
|---|---|---|---|---|---|---|---|---|---|---|---|
| Variety | CP | ADF | aNDF | ADL | DM | IVTDMD | NDFD1 | RFQ | RFV | Milk/ton | Milk/acre |
| A 5225 | 21.97 | 31.95 | 37.89 | 5.87 | 93.55 | 80.12 | 48.06 | 168.53 | 157.29 | 3,019.62 | 18,781.28 |
| Pillar, Actis | 21.31 | 33.48 | 39.37 | 6.09 | 93.08 | 79.36 | 48.27 | 160.94 | 148.73 | 2,950.12 | 19,502.90 |
| HybriForce-2400 | 22.01 | 31.35 | 37.21 | 5.76 | 93.37 | 81.07 | 49.29 | 174.78 | 161.38 | 3,050.66 | 18,804.82 |
| HybriForce-400 | 22.42 | 31.11 | 36.94 | 5.58 | 93.72 | 81.19 | 49.55 | 177.45 | 163.58 | 3,068.47 | 17,146.72 |
| WL 319 HQ | 23.57 | 29.17 | 34.54 | 5.22 | 93.59 | 82.95 | 50.66 | 193.83 | 178.88 | 3,150.05 | 18,869.80 |
| Grand Mean | 22.08 | 31.42 | 37.07 | 5.71 | 93.29 | 80.92 | 48.90 | 175.25 | 162.51 | 3,049.35 | 19,103.74 |
| LSD (0.05) | 0.93 | 1.55 | 1.71 | 0.33 | 0.60 | 1.29 | 1.49 | 11.79 | 11.16 | 75.74 | 1,386.77 |
| C.V. (%) | 2.58 | 3.02 | 2.82 | 3.53 | 0.39 | 0.98 | 1.86 | 4.12 | 4.21 | 1.52 | 4.45 |
| R2 | 0.66 | 0.62 | 0.65 | 0.71 | 0.43 | 0.68 | 0.64 | 0.64 | 0.62 | 0.58 | 0.77 |

The ADL advantage of CW093009 compared to other commercially available alfalfa varieties is shown in Table 72.

TABLE 72

| | | May (Cut 1) | | June (Cut 2) | | July (Cut 3) | | Weighted Mean | |
|---|---|---|---|---|---|---|---|---|---|
| FD Group | Variety | ADL Adv. | % ADL Adv. | ADL Adv. | % ADL Adv. | ADL Adv. | % ADL Adv. | ADL Adv. | % ADL Adv. |
| FD2 | PGI 212, VR TOTAL | 0.34 | 6% | −0.19 | −4% | −0.60 | −11% | −0.08 | −2% |
| FD3 | CW 093009 | 0.00 | 0% | 0.00 | 0% | 0.00 | 0% | 0.00 | 0% |
| FD3 | WL 319 HQ | 0.08 | 2% | 0.19 | 4% | −0.68 | −13% | −0.09 | −2% |
| FD4 | 54V46 | 0.73 | 12% | 0.48 | 9% | −0.03 | −1% | 0.45 | 8% |
| FD4 | Assalt ST | 0.59 | 10% | 0.50 | 9% | 0.48 | 8% | 0.54 | 9% |
| FD4 | Sundance III, PERFECTION | 0.52 | 9% | 0.27 | 5% | 0.20 | 3% | 0.36 | 6% |
| FD4 | PGI 437, Tower ST | 0.77 | 13% | 0.89 | 15% | 0.64 | 10% | 0.78 | 13% |
| FD4 | A 4330 | 0.50 | 9% | 0.23 | 4% | 0.04 | 1% | 0.30 | 5% |
| FD4 | Pillar, Actis | 0.83 | 14% | 1.33 | 21% | 0.10 | 2% | 0.78 | 13% |
| FD4 | HybriForce-2400 | 0.54 | 9% | 0.73 | 13% | 0.00 | 0% | 0.45 | 8% |
| FD4 | HybriForce-400 | 0.53 | 9% | 0.44 | 8% | −0.32 | −6% | 0.28 | 5% |
| FD5 | 55V12 | 1.27 | 20% | 0.63 | 11% | −0.06 | −1% | 0.72 | 12% |
| FD5 | PGI 557, Lelia | 0.29 | 5% | 0.83 | 14% | −0.29 | −5% | 0.30 | 5% |
| FD5 | StarGold | 0.77 | 13% | 0.16 | 3% | −0.48 | −9% | 0.25 | 5% |
| FD5 | A 5225 | 0.59 | 10% | 0.95 | 16% | 0.07 | 1% | 0.56 | 10% |
| FD5 | WL 363 HQ | 0.25 | 5% | 0.27 | 5% | 0.20 | 3% | 0.25 | 4% |

CW093009 and commercially available alfalfa varieties were grown in Wisconsin and harvested at about 28, 35, and 42 days in Year 1. Table 73 shows the weighted mean of 3 cuts of 28 days. Table 75 shows the weighted mean of 3 cuts of 35 days. Table 77 shows the weighted mean of 5 cuts of 42 days. The ADL advantage of CW093009 compared to other commercially available alfalfa varieties for the data of Tables 73, 75, and 77 are shown in Tables 74, 76, and 78, respectively.

TABLE 73

| | Year 1—Weighted Mean (28 days) | | | | | | | | | |
|---|---|---|---|---|---|---|---|---|---|---|
| Variety | CP | ADF | aNDF | ADL | DM | IVTDMD | NDFD1 | RFQ | RFV | Milk/ton |
| CW 093009 | 25.04 | 25.56 | 30.80 | 5.14 | 94.23 | 84.49 | 51.90 | 222.19 | 208.77 | 3,269.79 |
| 54H11 | 24.13 | 28.92 | 34.32 | 6.10 | 94.38 | 81.09 | 49.83 | 191.88 | 180.17 | 3,115.86 |
| PGI 215, Velvet | 25.02 | 25.71 | 30.76 | 5.38 | 94.30 | 83.53 | 51.84 | 223.47 | 209.03 | 3,290.76 |
| PGI 212, VR TOTAL | 25.33 | 26.76 | 31.85 | 5.46 | 94.17 | 83.26 | 50.07 | 208.78 | 199.15 | 3,186.30 |
| Keystone II | 24.62 | 27.08 | 32.29 | 5.73 | 94.32 | 82.51 | 50.27 | 205.97 | 195.51 | 3,175.93 |
| StarGold | 24.28 | 27.68 | 33.02 | 5.86 | 94.35 | 81.92 | 50.00 | 202.70 | 192.26 | 3,161.00 |
| Caliber | 24.55 | 26.89 | 31.99 | 5.64 | 94.24 | 82.80 | 50.25 | 212.09 | 199.35 | 3,247.75 |
| SpringGold | 24.29 | 26.71 | 31.89 | 5.73 | 94.19 | 82.74 | 50.40 | 213.15 | 200.86 | 3,245.36 |
| WL 319 HQ | 24.85 | 26.52 | 31.78 | 5.48 | 94.24 | 83.29 | 50.84 | 212.38 | 200.35 | 3,221.45 |
| WL 363 HQ | 23.88 | 27.76 | 32.88 | 5.84 | 94.33 | 81.89 | 50.25 | 202.27 | 191.15 | 3,155.88 |
| Grand Mean | 24.74 | 26.94 | 32.14 | 5.61 | 94.26 | 82.77 | 50.64 | 209.29 | 197.72 | 3,197.59 |

TABLE 73-continued

| | Year 1—Weighted Mean (28 days) | | | | | | | | | |
|---|---|---|---|---|---|---|---|---|---|---|
| Variety | CP | ADF | aNDF | ADL | DM | IVTDMD | NDFD1 | RFQ | RFV | Milk/ton |
| LSD (0.05) | 0.78 | 0.92 | 1.06 | 0.25 | 0.14 | 1.09 | 1.27 | 9.79 | 8.17 | 66.71 |
| C.V. (%) | 1.92 | 2.09 | 2.02 | 2.76 | 0.09 | 0.81 | 1.54 | 2.87 | 2.53 | 1.28 |
| R2 | 0.63 | 0.79 | 0.76 | 0.78 | 0.53 | 0.71 | 0.53 | 0.75 | 0.78 | 0.72 |

TABLE 74

| | | Cut 1 | | Cut 2 | | Cut 3 | | Weighted Mean | |
|---|---|---|---|---|---|---|---|---|---|
| FD Group | Variety | ADL Adv. | % ADL Adv. | ADL Adv. | % ADL Adv. | ADL Adv. | % ADL Adv. | ADL Adv. | % ADL Adv. |
| FD2 | PGI 215, Velvet | −0.32 | −7% | 0.73 | 12% | 0.30 | 5% | 0.24 | 4% |
| FD2 | PGI 212, VR TOTAL | 0.19 | 4% | 0.66 | 11% | 0.11 | 2% | 0.32 | 6% |
| FD3 | CW 093009 | 0.00 | 0% | 0.00 | 0% | 0.00 | 0% | 0.00 | 0% |
| FD3 | Keystone II | 0.38 | 7% | 0.75 | 13% | 0.64 | 10% | 0.59 | 10% |
| FD3 | WL 319 HQ | 0.50 | 9% | 0.33 | 6% | 0.19 | 3% | 0.34 | 6% |
| FD4 | 54H11 | 1.08 | 18% | 0.86 | 14% | 0.93 | 15% | 0.96 | 16% |
| FD4 | Caliber | −0.14 | −3% | 1.28 | 20% | 0.35 | 6% | 0.50 | 9% |
| FD5 | StarGold | 0.18 | 4% | 0.69 | 12% | 1.30 | 19% | 0.72 | 12% |
| FD5 | SpringGold | −0.02 | −1% | 1.29 | 20% | 0.50 | 8% | 0.59 | 10% |
| FD5 | WL 363 HQ | 0.35 | 7% | 0.96 | 16% | 0.81 | 13% | 0.71 | 12% |

TABLE 75

| | Year 1—Weighted Mean (35 days) | | | | | | | | | |
|---|---|---|---|---|---|---|---|---|---|---|
| Variety | CP | ADF | aNDF | ADL | DM | IVTDMD | NDFD1 | RFQ | RFV | Milk/ton |
| CW 093009 | 22.32 | 29.06 | 34.77 | 6.10 | 94.16 | 80.62 | 47.48 | 183.78 | 178.48 | 3,051.46 |
| 54H11 | 21.08 | 31.67 | 37.68 | 6.87 | 94.24 | 77.59 | 45.67 | 165.43 | 161.12 | 2,953.10 |
| PGI 215, Velvet | 22.50 | 30.09 | 35.85 | 6.42 | 94.19 | 79.19 | 47.05 | 176.17 | 170.59 | 3,008.47 |
| PGI 212, VR TOTAL | 23.25 | 30.91 | 36.60 | 6.53 | 94.13 | 78.88 | 46.64 | 169.04 | 166.04 | 2,898.47 |
| Keystone II | 22.10 | 30.90 | 36.81 | 6.65 | 94.07 | 78.90 | 46.18 | 167.97 | 164.60 | 2,938.81 |
| StarGold | 21.67 | 31.66 | 37.52 | 6.76 | 94.14 | 78.23 | 45.75 | 163.80 | 160.69 | 2,913.83 |
| Caliber | 21.43 | 30.74 | 36.52 | 6.60 | 94.03 | 78.60 | 45.97 | 170.94 | 166.19 | 3,006.67 |
| SpringGold | 21.90 | 30.35 | 36.22 | 6.55 | 94.22 | 78.95 | 45.90 | 172.33 | 168.50 | 3,006.80 |
| WL 319 HQ | 22.01 | 30.69 | 36.62 | 6.53 | 93.98 | 79.00 | 46.41 | 170.04 | 166.14 | 2,957.25 |
| WL 363 HQ | 20.99 | 30.93 | 36.88 | 6.67 | 94.14 | 78.18 | 46.10 | 169.27 | 164.22 | 2,998.83 |
| Grand Mean | 22.02 | 30.69 | 36.51 | 6.53 | 94.13 | 78.94 | 46.60 | 171.56 | 166.92 | 2,971.64 |
| LSD (0.05) | 1.10 | 1.89 | 2.14 | 0.51 | 0.28 | 1.65 | 1.35 | 14.60 | 13.46 | 89.01 |
| C.V. (%) | 3.05 | 3.77 | 3.58 | 4.74 | 0.18 | 1.28 | 1.78 | 5.21 | 4.94 | 1.83 |
| R2 | 0.55 | 0.41 | 0.40 | 0.47 | 0.29 | 0.51 | 0.59 | 0.43 | 0.40 | 0.54 |

TABLE 76

| | | Cut 1 | | Cut 2 | | Cut 3 | | Weighted Mean | |
|---|---|---|---|---|---|---|---|---|---|
| FD Group | Variety | ADL Adv. | % ADL Adv. | ADL Adv. | % ADL Adv. | ADL Adv. | % ADL Adv. | ADL Adv. | % ADL Adv. |
| FD2 | PGI 215, Velvet | 0.47 | 8% | 0.94 | 13% | −0.44 | −7% | 0.32 | 5% |
| FD2 | PGI 212, VR TOTAL | 0.76 | 12% | 1.07 | 15% | −0.54 | −9% | 0.43 | 7% |
| FD3 | CW 093009 | 0.00 | 0% | 0.00 | 0% | 0.00 | 0% | 0.00 | 0% |
| FD3 | Keystone II | 0.87 | 13% | 0.97 | 14% | −0.20 | −3% | 0.55 | 8% |
| FD3 | WL 319 HQ | 0.55 | 9% | 1.02 | 14% | −0.28 | −5% | 0.43 | 7% |
| FD4 | 54H11 | 1.11 | 16% | 1.21 | 17% | −0.03 | 0% | 0.76 | 11% |
| FD4 | Caliber | 0.59 | 9% | 0.80 | 12% | 0.10 | 2% | 0.50 | 8% |
| FD5 | StarGold | 0.53 | 8% | 1.37 | 19% | 0.07 | 1% | 0.66 | 10% |
| FD5 | SpringGold | 0.58 | 9% | 0.94 | 13% | −0.19 | −3% | 0.44 | 7% |
| FD5 | WL 363 HQ | 0.65 | 10% | 0.70 | 10% | 0.34 | 5% | 0.57 | 8% |

TABLE 77

Year 1—Weighted Mean (42 days)

| Variety | CP | ADF | aNDF | ADL | DM | IVTDMD | NDFD1 | RFQ | RFV | Milk/ton |
|---|---|---|---|---|---|---|---|---|---|---|
| CW 093009 | 20.53 | 28.07 | 34.10 | 6.05 | 93.74 | 80.17 | 46.07 | 189.57 | 184.43 | 3,175.18 |
| 54H11 | 17.93 | 32.59 | 39.34 | 7.40 | 93.88 | 75.18 | 41.55 | 150.31 | 151.77 | 2,948.20 |
| PGI 215, Velvet | 20.80 | 28.92 | 34.89 | 6.32 | 93.84 | 79.32 | 45.12 | 182.78 | 179.30 | 3,128.44 |
| PGI 212, VR TOTAL | 20.83 | 29.72 | 35.77 | 6.39 | 93.76 | 79.16 | 45.33 | 175.60 | 171.97 | 3,069.57 |
| Keystone II | 20.49 | 28.73 | 34.91 | 6.32 | 93.72 | 79.68 | 45.49 | 182.52 | 178.38 | 3,138.80 |
| StarGold | 19.67 | 30.96 | 37.19 | 6.72 | 93.83 | 77.85 | 44.83 | 166.11 | 162.83 | 3,013.66 |
| Caliber | 20.23 | 29.67 | 35.71 | 6.40 | 93.70 | 78.90 | 44.83 | 174.51 | 172.26 | 3,062.59 |
| SpringGold | 19.61 | 29.77 | 35.96 | 6.53 | 93.79 | 78.45 | 44.92 | 174.34 | 170.46 | 3,099.92 |
| WL 319 HQ | 20.68 | 30.57 | 36.83 | 6.73 | 93.87 | 77.95 | 45.47 | 170.82 | 166.33 | 3,033.20 |
| WL 363 HQ | 19.94 | 28.96 | 35.03 | 6.44 | 93.86 | 78.80 | 45.08 | 180.95 | 177.31 | 3,131.52 |
| Grand Mean | 22.02 | 30.69 | 36.51 | 6.53 | 94.11 | 78.94 | 46.60 | 171.56 | 166.92 | 2,971.64 |
| LSD (0.05) | 1.10 | 1.89 | 2.14 | 0.51 | 0.28 | 1.65 | 1.35 | 14.60 | 13.46 | 89.01 |
| C.V. (%) | 3.05 | 3.77 | 3.58 | 4.74 | 0.18 | 1.28 | 1.78 | 5.21 | 4.94 | 1.83 |
| R2 | 0.55 | 0.41 | 0.40 | 0.47 | 0.29 | 0.51 | 0.59 | 0.43 | 0.40 | 0.54 |

TABLE 78

| | | May (Cut 1) | | June (Cut 2) | | July (Cut 3) | | Weighted Mean | |
|---|---|---|---|---|---|---|---|---|---|
| FD Group | Variety | ADL Adv. | % ADL Adv. | ADL Adv. | % ADL Adv. | ADL Adv. | % ADL Adv. | ADL Adv. | % ADL Adv. |
| FD2 | PGI 215, Velvet | 0.25 | 4% | 0.99 | 15% | −0.44 | −8% | 0.27 | 4% |
| FD2 | PGI 212, VR TOTAL | 0.36 | 5% | 0.68 | 11% | −0.02 | 0% | 0.34 | 5% |
| FD3 | CW 093009 | 0.00 | 0% | 0.00 | 0% | 0.00 | 0% | 0.00 | 0% |
| FD3 | Keystone II | 0.06 | 1% | 0.88 | 13% | −0.13 | −2% | 0.27 | 4% |
| FD3 | WL 319 HQ | 1.01 | 14% | 1.07 | 16% | −0.03 | −1% | 0.68 | 10% |
| FD4 | 54H11 | 1.46 | 19% | 1.91 | 25% | 0.69 | 10% | 1.35 | 18% |
| FD4 | Caliber | −0.45 | −8% | 1.22 | 17% | 0.29 | 5% | 0.35 | 6% |
| FD5 | StarGold | 0.03 | 1% | 1.36 | 19% | 0.62 | 9% | 0.67 | 10% |
| FD5 | SpringGold | −0.03 | 0% | 1.01 | 15% | 0.47 | 7% | 0.48 | 7% |
| FD5 | WL 363 HQ | 0.25 | 4% | 0.70 | 11% | 0.23 | 4% | 0.39 | 6% |

Example 12

CW104015

The forage quality of CW104015 was compared to various commercially available alfalfa varieties using the methods described in Example 1. CW104015 and the commercially available alfalfa varieties were harvested in in May, June and July in Year 1. See Tables 79-81. The weighted mean for the three cuts is shown in Table 82.

TABLE 79

May Year 1—Cut 1

| Variety | CP | ADF | aNDF | ADL | DM | IVTDMD | NDFD1 | RFQ | RFV | Milk/ton | Milk/acre |
|---|---|---|---|---|---|---|---|---|---|---|---|
| CW 104015 | 24.15 | 25.20 | 30.51 | 5.09 | 92.45 | 85.27 | 53.62 | 228.34 | 211.30 | 3,299.74 | 8,150.79 |
| 55V12 | 22.96 | 28.11 | 34.16 | 6.13 | 92.70 | 82.04 | 47.90 | 188.48 | 182.58 | 3,098.39 | 7,833.78 |
| PGI 557, Lelia | 24.34 | 26.56 | 32.24 | 5.78 | 92.69 | 83.58 | 50.87 | 208.07 | 196.96 | 3,191.90 | 7,949.76 |
| Pillar, Actis | 24.62 | 26.54 | 32.04 | 5.50 | 92.60 | 84.08 | 51.68 | 210.13 | 198.10 | 3,177.31 | 7,338.73 |
| HybriForce-400 | 23.84 | 26.38 | 31.94 | 5.32 | 92.47 | 84.44 | 51.85 | 212.87 | 199.09 | 3,226.92 | 8,480.38 |
| WL 319 HQ | 24.79 | 26.07 | 31.49 | 5.29 | 92.64 | 84.74 | 51.83 | 215.12 | 203.00 | 3,201.97 | 8,465.12 |
| Grand Mean | 24.39 | 25.86 | 31.31 | 5.43 | 92.51 | 84.43 | 51.77 | 216.76 | 204.59 | 3,220.57 | 7,945.72 |
| LSD (0.05) | 0.78 | 1.28 | 1.47 | 0.32 | 0.33 | 1.20 | 1.99 | 15.83 | 12.67 | 100.16 | 579.87 |
| C.V. (%) | 1.97 | 3.03 | 2.87 | 3.61 | 0.22 | 0.87 | 2.35 | 4.47 | 3.79 | 1.90 | 4.47 |
| R2 | 0.61 | 0.57 | 0.58 | 0.70 | 0.30 | 0.55 | 0.54 | 0.55 | 0.56 | 0.46 | 0.77 |

TABLE 80

June Year 1—Cut 2

| Variety | CP | ADF | aNDF | ADL | DM | IVTDMD | NDFD1 | RFQ | RFV | Milk/ton | Milk/acre |
|---|---|---|---|---|---|---|---|---|---|---|---|
| CW 104015 | 19.81 | 21.74 | 27.74 | 4.36 | 94.89 | 86.38 | 49.62 | 257.99 | 241.83 | 3,675.72 | 7,200.21 |
| 55V12 | 19.70 | 24.00 | 30.20 | 5.11 | 94.84 | 84.10 | 48.22 | 230.68 | 217.02 | 3,545.78 | 6,266.51 |
| PGI 557, Lelia | 20.58 | 23.39 | 29.16 | 4.91 | 94.54 | 85.13 | 49.17 | 241.23 | 226.26 | 3,568.14 | 6,467.18 |
| Pillar, Actis | 19.61 | 25.29 | 31.42 | 5.20 | 94.72 | 83.93 | 48.80 | 220.60 | 206.52 | 3,460.11 | 7,300.65 |
| HybriForce-400 | 19.79 | 22.98 | 28.95 | 4.60 | 94.63 | 85.62 | 49.75 | 245.15 | 228.31 | 3,613.22 | 5,928.72 |
| WL 319 HQ | 19.76 | 22.30 | 28.36 | 4.52 | 94.22 | 85.76 | 49.44 | 249.83 | 234.88 | 3,622.02 | 6,333.83 |
| Grand Mean | 19.89 | 23.33 | 29.35 | 4.81 | 94.48 | 85.17 | 49.28 | 240.81 | 225.46 | 3,579.49 | 6,803.83 |

TABLE 80-continued

| | June Year 1—Cut 2 | | | | | | | | | | |
|---|---|---|---|---|---|---|---|---|---|---|---|
| Variety | CP | ADF | aNDF | ADL | DM | IVTDMD | NDFD1 | RFQ | RFV | Milk/ton | Milk/acre |
| LSD (0.05) | 1.59 | 2.92 | 3.05 | 0.64 | 0.66 | 1.98 | 2.11 | 32.24 | 29.96 | 177.84 | 885.00 |
| C.V. (%) | 4.90 | 7.68 | 6.37 | 8.21 | 0.43 | 1.42 | 2.63 | 8.20 | 8.14 | 3.04 | 7.97 |
| R2 | 0.40 | 0.40 | 0.41 | 0.45 | 0.42 | 0.44 | 0.36 | 0.41 | 0.42 | 0.37 | 0.73 |

TABLE 81

| | July Year 1—Cut 3 | | | | | | | | | | |
|---|---|---|---|---|---|---|---|---|---|---|---|
| Variety | CP | ADF | aNDF | ADL | DM | IVTDMD | NDFD1 | RFQ | RFV | Milk/ton | Milk/acre |
| CW 104015 | 23.46 | 30.00 | 35.24 | 6.40 | 93.73 | 80.69 | 45.63 | 178.01 | 173.97 | 3,050.94 | 5,355.20 |
| 55V12 | 22.61 | 31.43 | 37.12 | 6.80 | 94.21 | 78.88 | 43.11 | 161.23 | 161.62 | 2,960.96 | 4,750.55 |
| PGI 557, Lelia | 23.40 | 30.33 | 35.78 | 6.64 | 94.23 | 79.88 | 44.59 | 172.23 | 170.24 | 3,020.07 | 4,802.41 |
| Pillar, Actis | 22.01 | 32.89 | 38.42 | 7.22 | 94.07 | 77.94 | 43.83 | 156.77 | 153.45 | 2,951.87 | 4,927.77 |
| HybriForce-400 | 24.77 | 28.83 | 33.78 | 6.12 | 93.29 | 81.88 | 46.73 | 188.25 | 183.25 | 3,087.80 | 4,688.20 |
| WL 319 HQ | 24.27 | 28.55 | 33.46 | 6.12 | 93.88 | 82.12 | 47.01 | 193.24 | 185.58 | 3,170.15 | 4,889.73 |
| Grand Mean | 23.23 | 30.39 | 35.74 | 6.58 | 93.93 | 80.22 | 45.01 | 174.00 | 170.35 | 3,046.40 | 5,193.02 |
| LSD (0.05) | 1.06 | 1.85 | 2.14 | 0.47 | 0.72 | 1.71 | 1.86 | 16.72 | 14.47 | 109.67 | 462.69 |
| C.V. (%) | 2.81 | 3.73 | 3.67 | 4.37 | 0.47 | 1.30 | 2.53 | 5.88 | 5.20 | 2.20 | 5.46 |
| R2 | 0.70 | 0.62 | 0.64 | 0.65 | 0.31 | 0.66 | 0.65 | 0.63 | 0.62 | 0.52 | 0.74 |

TABLE 82

| | Year 1—Weighted Mean | | | | | | | | | | |
|---|---|---|---|---|---|---|---|---|---|---|---|
| Variety | CP | ADF | aNDF | ADL | DM | IVTDMD | NDFD1 | RFQ | RFV | Milk/ton | Milk/acre |
| CW 104015 | 22.58 | 25.47 | 30.98 | 5.24 | 93.59 | 84.32 | 50.08 | 223.41 | 210.34 | 3,347.87 | 20,706.21 |
| 55V12 | 21.87 | 27.79 | 33.78 | 6.01 | 93.75 | 81.79 | 46.68 | 193.61 | 187.12 | 3,194.88 | 18,850.84 |
| PGI 557, Lelia | 22.93 | 26.60 | 32.25 | 5.74 | 93.67 | 83.06 | 48.65 | 208.64 | 198.78 | 3,261.68 | 19,219.34 |
| Pillar, Actis | 22.21 | 27.96 | 33.69 | 5.90 | 93.71 | 82.27 | 48.50 | 199.09 | 188.77 | 3,212.78 | 19,567.16 |
| HybriForce-400 | 22.93 | 26.06 | 31.58 | 5.33 | 93.30 | 84.10 | 49.91 | 215.55 | 203.20 | 3,299.89 | 19,097.30 |
| WL 319 HQ | 23.18 | 25.61 | 31.08 | 5.28 | 93.42 | 84.36 | 49.88 | 219.65 | 207.85 | 3,316.90 | 19,688.68 |
| Grand Mean | 22.65 | 26.36 | 31.96 | 5.56 | 93.53 | 83.47 | 49.09 | 212.12 | 201.35 | 3,283.16 | 19,942.58 |
| LSD (0.05) | 0.59 | 1.33 | 1.46 | 0.31 | 0.31 | 1.04 | 1.31 | 14.60 | 12.84 | 87.60 | 1,551.20 |
| C.V. (%) | 1.60 | 3.10 | 2.79 | 3.46 | 0.20 | 0.77 | 1.64 | 4.22 | 3.91 | 1.63 | 4.76 |
| R2 | 0.71 | 0.53 | 0.55 | 0.64 | 0.44 | 0.60 | 0.58 | 0.52 | 0.51 | 0.47 | 0.68 |

The ADL advantage of CW104015 compared to other commercially available alfalfa varieties is shown in Table 83.

TABLE 83

| | | May (Cut 1) | | June (Cut 2) | | July (Cut 3) | | Weighted Mean | |
|---|---|---|---|---|---|---|---|---|---|
| FD Group | Variety | ADL Adv. | % ADL Adv. | ADL Adv. | % ADL Adv. | ADL Adv. | % ADL Adv. | ADL Adv. | % ADL Adv. |
| FD3 | WL 319 HQ | 0.19 | 4% | 0.16 | 4% | −0.28 | −5% | 0.04 | 1% |
| FD4 | CW 104015 | 0.00 | 0% | 0.00 | 0% | 0.00 | 0% | 0.00 | 0% |
| FD4 | Pillar, Actis | 0.41 | 7% | 0.84 | 16% | 0.82 | 11% | 0.66 | 11% |
| FD4 | HybriForce-400 | 0.22 | 4% | 0.24 | 5% | −0.28 | −5% | 0.09 | 2% |
| FD5 | 55V12 | 1.03 | 17% | 0.75 | 15% | 0.40 | 6% | 0.77 | 13% |
| FD5 | PGI 557, Lelia | 0.69 | 12% | 0.55 | 11% | 0.23 | 3% | 0.51 | 9% |

CW104015 and commercially available alfalfa varieties were grown in Wisconsin and harvested at 28 and 35 days in Year 1. Table 84 shows the weighted mean of 2 cuts of 28 days. Table 85 shows the weighted mean of 2 cuts of 35 days. The ADL advantage of CW104015 compared to other commercially available alfalfa varieties for the data of Tables 84 and 85 are shown in Tables 86 and 87, respectively.

TABLE 84

| | Year 1—Weighted Mean (28 days) | | | | | | | | | | |
|---|---|---|---|---|---|---|---|---|---|---|---|
| Variety | CP | ADF | aNDF | ADL | DM | IVTDMD | NDFD1 | RFQ | RFV | Milk/ton | Milk/acre |
| CW 104015 | 22.30 | 28.59 | 33.96 | 5.93 | 94.54 | 82.46 | 51.55 | 200.57 | 182.77 | 3,219.81 | 5,854.55 |
| 54H11 | 21.14 | 29.98 | 35.78 | 6.39 | 94.72 | 80.20 | 50.09 | 187.71 | 170.71 | 3,198.42 | 7,658.14 |

TABLE 84-continued

Year 1—Weighted Mean (28 days)

| Variety | CP | ADF | aNDF | ADL | DM | IVTDMD | NDFD1 | RFQ | RFV | Milk/ton | Milk/acre |
|---|---|---|---|---|---|---|---|---|---|---|---|
| 55V50 | 21.00 | 32.32 | 38.19 | 6.75 | 94.74 | 78.74 | 49.31 | 169.77 | 155.43 | 3,025.36 | 6,405.25 |
| PGI 459, Qwest | 21.29 | 31.25 | 36.97 | 6.54 | 94.60 | 79.84 | 49.90 | 178.10 | 162.57 | 3,091.26 | 5,928.26 |
| WL 319 HQ | 22.44 | 29.04 | 34.43 | 6.06 | 94.53 | 81.79 | 50.79 | 195.30 | 179.38 | 3,180.09 | 5,793.20 |
| WL 354 HQ | 22.21 | 29.88 | 35.57 | 6.27 | 94.69 | 80.58 | 50.07 | 186.69 | 171.78 | 3,140.79 | 6,100.39 |
| Grand Mean | 21.93 | 29.88 | 35.49 | 6.26 | 94.62 | 80.87 | 50.51 | 188.73 | 172.61 | 3,153.84 | 6,236.41 |
| LSD (0.05) | 0.65 | 1.01 | 1.07 | 0.20 | 0.12 | 0.86 | 0.95 | 8.50 | 7.21 | 73.01 | 1,600.32 |
| C.V. (%) | 2.10 | 2.40 | 2.14 | 2.30 | 0.09 | 0.75 | 1.32 | 3.18 | 2.95 | 1.64 | 18.15 |
| R2 | 0.75 | 0.83 | 0.85 | 0.85 | 0.55 | 0.86 | 0.65 | 0.82 | 0.84 | 0.72 | 0.28 |

TABLE 85

Year 1—Weighted Mean (35 days)

| Variety | CP | ADF | aNDF | ADL | DM | IVTDMD | NDFD1 | RFQ | RFV | Milk/ton | Milk/acre |
|---|---|---|---|---|---|---|---|---|---|---|---|
| CW 104015 | 21.40 | 31.13 | 36.99 | 6.46 | 93.82 | 79.22 | 49.28 | 175.66 | 163.53 | 3,025.57 | 11,269.31 |
| 54H11 | 19.70 | 32.51 | 39.06 | 7.17 | 94.02 | 76.60 | 45.99 | 159.81 | 151.73 | 3,012.96 | 12,380.61 |
| 55V50 | 20.01 | 35.23 | 41.75 | 7.55 | 94.05 | 75.41 | 47.34 | 145.81 | 137.96 | 2,755.76 | 11,751.56 |
| PGI 459, Qwest | 21.07 | 32.36 | 38.40 | 6.95 | 93.93 | 77.43 | 47.93 | 164.02 | 154.75 | 2,940.39 | 11,398.22 |
| WL 319 HQ | 21.40 | 31.52 | 37.65 | 6.66 | 93.83 | 78.49 | 48.54 | 169.98 | 160.04 | 2,976.59 | 10,278.17 |
| WL 354 HQ | 21.23 | 32.61 | 38.86 | 6.93 | 93.93 | 77.38 | 47.81 | 161.08 | 152.46 | 2,912.25 | 11,211.38 |
| Grand Mean | 20.88 | 32.36 | 38.58 | 6.90 | 93.93 | 77.59 | 48.07 | 164.06 | 154.58 | 2,938.07 | 11,429.24 |
| LSD (0.05) | 0.92 | 2.31 | 2.44 | 0.42 | 0.27 | 1.77 | 0.93 | 13.80 | 13.89 | 136.78 | 920.58 |
| C.V. (%) | 3.10 | 5.05 | 4.48 | 4.31 | 0.20 | 1.61 | 1.37 | 5.95 | 6.36 | 3.29 | 5.70 |
| R2 | 0.57 | 0.49 | 0.54 | 0.67 | 0.24 | 0.58 | 0.79 | 0.60 | 0.51 | 0.59 | 0.61 |

TABLE 86

| FD Group | Variety | Cut 1 ADL Adv. | Cut 1 % ADL Adv. | Cut 2 ADL Adv. | Cut 2 % ADL Adv. | Weighted Mean ADL Adv. | Weighted Mean % ADL Adv. |
|---|---|---|---|---|---|---|---|
| FD3 | WL 319 HQ | 0.25 | 4% | 0.04 | 1% | 0.13 | 2% |
| FD4 | CW 104015 | 0.00 | 0% | 0.00 | 0% | 0.00 | 0% |
| FD4 | 54H11 | 0.42 | 6% | 0.50 | 8% | 0.46 | 7% |
| FD4 | PGI 459, Qwest | 0.49 | 8% | 0.70 | 11% | 0.61 | 9% |
| FD4 | WL 354 HQ | 0.39 | 6% | 0.28 | 5% | 0.34 | 5% |
| FD5 | 55V50 | 0.97 | 14% | 0.68 | 10% | 0.82 | 12% |

TABLE 87

| FD Group | Variety | Cut 1 ADL Adv. | Cut 1 % ADL Adv. | Cut 2 ADL Adv. | Cut 2 % ADL Adv. | Weighted Mean ADL Adv. | Weighted Mean % ADL Adv. |
|---|---|---|---|---|---|---|---|
| FD3 | WL 319 HQ | 0.11 | 2% | 0.30 | 4% | 0.20 | 3% |
| FD4 | CW 104015 | 0.00 | 0% | 0.00 | 0% | 0.00 | 0% |
| FD4 | 54H11 | 1.03 | 14% | 0.45 | 6% | 0.72 | 10% |
| FD4 | PGI 459, Qwest | 0.74 | 10% | 0.27 | 4% | 0.49 | 7% |
| FD4 | WL 354 HQ | 0.74 | 10% | 0.22 | 3% | 0.47 | 7% |
| FD5 | 55V50 | 1.30 | 17% | 0.90 | 12% | 1.09 | 14% |

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

For reasons of completeness, various aspects of the invention are set out in the following numbered clauses:

Clause 1. An alfalfa variety that has at least about 5.0% less lignin content as a percent of dry matter, compared to a control alfalfa variety grown under the same field growing conditions.

Clause 2. The alfalfa variety of clause 1, wherein the alfalfa variety has at least about 5.0% to at least about 25.0% less total lignin content.

Clause 3. The alfalfa variety of clause 1 or 2, wherein the alfalfa variety has about 5.0% to about 25% less acid detergent lignin content.

Clause 4. The alfalfa variety of clause 3, wherein the alfalfa variety has at least about 6.0% to at least about 10.0% less acid detergent lignin content.

Clause 5. The alfalfa variety of any one of clauses 1-4, wherein the lignin content is measured about 21 days after clipping, about 22 days after clipping, about 28 days after clipping, about 29 days after clipping, about 35 days after clipping, or about 42 days after clipping.

Clause 6. The alfalfa variety of any one of clauses 1-5, wherein the lignin content is measured in the lower stems or in the whole plant of the alfalfa plant.

Clause 7. The alfalfa variety of any one of clause 1-6, wherein the alfalfa variety has at least about 5.0% to about 25.0% more total digestible nutrient, about 5.0% to about 25.0% more relative forage quality, about 5.0% to about 25.0% more relative forage value, or about 5.0% to about 25.0% more milk per ton of dry mass compared to a control alfalfa variety grown under the same field growing conditions.

Clause 8. The alfalfa variety of clause 7, wherein the total digestible nutrient is measured as in vitro total dry matter digestibility, neutral detergent fiber digestibility, or total tract neutral detergent fiber digestibility.

Clause 9. The alfalfa variety of clause 8, wherein the total digestibility nutrient is measured about 21 days after clipping, about 22 days after clipping, about 28 days after clipping, about 29 days after clipping, about 35 days after clipping, or about 42 days after clipping.

Clause 10. The alfalfa variety of any one of clauses 1-9, wherein the control alfalfa variety is a commercial alfalfa variety.

Clause 11. The alfalfa variety of any one of clauses 1-10, wherein the control alfalfa variety is a commercial alfalfa variety in the same fall dormancy group as the alfalfa variety or a commercial alfalfa variety in a different fall dormancy group as the alfalfa variety.

Clause 12. The alfalfa variety of clause 11, wherein the commercial alfalfa variety is selected from the group consisting of 55V12, 56S82, Althea, Cisco II, Cornerstone, CW 1010, Del Rio, Fertilac 10, HybriForce 2600, HybriForce 700, HybriForce-2400, HybriForce-3400, Keystone II, Magnum 7, Magnum 7-Wet, Mecca III, N-R-Gee, P58N57, PGI 212, VR TOTAL, PGI 529 (DOMINATOR), PGI 557 (LELIA), PGI 608, PGI 709, PGI 801, PGI 909, PILLAR ST, ROBUST, Sedona, StarGold, SW7410, WL 319 HQ, WL 440HQ, 5010, 243 STEALTH II, 4N900, 53Q6 54H11, 54H91, 54V46, 55V50, 59N59, A 30-06, A 4330, A 5225, Adrenalin, Ameristand 403T, Ameristand 407TQ, Ascend, Assalt ST, Barricade SLT, Caliber, Contender, Croplan 9, CUF 101, CW 054004, CW 090075, CW 093009, CW 096043, CW 099079, CW 103009, CW 104015, CW 197, DS 1020, DS 598, Exalt, eXclaim, ForageGold, Foremost II, Valid, GH 717, HybriForce-400, Legend Extra, Magna 995, Optimus, P59N59, PERFORMER, PGI 1007 BA, PGI 215, Velvet, PGI 437, PGI 437, Tower ST, PGI 459, PGI 459, Quest, PGI 459, Qwest, PGI 908S, Pillar, Actis, Rugged, SHOWDOWN, SolarGold, CORNERSTONE, SpringGold, SummerGold, Summit, Sundance II, Sansar, Super 10, SW 1, SW 9720, TS 4006, TS 4007, TS 4010, TS 4013, TS 4027, WinterKing II, Megan, WinterKing III, WL 357 HQ, WL 363 HQ, and WL440.

Clause 13. The alfalfa variety of any one of clauses 1-12 comprising:
i) about 12.5% germplasm from alfalfa variety PGI 608, about 12.5% germplasm from alfalfa variety CW 26071, about 12.5% germplasm from alfalfa variety CW 056080, about 37.5% germplasm from alfalfa variety CW 066081, about 12.5% germplasm from alfalfa variety 06-7-514, and about 12.5% germplasm from alfalfa variety 06-7-525;
ii) about 50% germplasm from alfalfa variety CW 10-017 and about 50% germplasm from alfalfa variety CW10-018;
iii) about 9% germplasm from DK 194, about 9% germplasm from SPS9000, about 4% germplasm from WL 625, about 4% germplasm from SW9628, about 3% germplasm from CW 195, about 1% germplasm from Millenia, about 1% germplasm from CW 194 Premium, and about 69% germplasm from miscellaneous Alforex Seeds breeding populations;
iv) about 26% germplasm from PGI 1007BA, about 10% germplasm from Mirage, about 9% germplasm from CW 1010, about 4% germplasm from DK 189, about 2% germplasm from Super 10, about 2% germplasm from Millenia, about 2% germplasm from DK 194, about 1% germplasm from DK 191, and about 44% germplasm from miscellaneous Alforex Seeds breeding populations;
v) about 100% germplasm from CW D4-005;
vi) about 50% germplasm from CW 09-014 and about 50% germplasm from CW 09-015; or
vii) about 6% germplasm from Adrenalin, about 6% germplasm from WinterKing III, about 18% germplasm from SolarGold, and about 35% germplasm from CW 09-039, and about 35% germplasm from CW 09-040.

Clause 14. The alfalfa variety of any one of clauses 1-13, wherein the alfalfa variety is designated CW096043, a sample of said seed has been deposited as ATCC Accession Number PTA-122473.

Clause 15. The alfalfa variety of any one of clauses 1-13, wherein the alfalfa variety is designated CW103009, a sample of said seed has been deposited as ATCC Accession Number PTA-122475.

Clause 16. The alfalfa variety of any one of clauses 1-13, wherein the alfalfa variety is designated CW099079, a sample of said seed has been deposited as ATCC Accession Number PTA-122474.

Clause 17. The alfalfa variety of any one of clauses 1-13, wherein the alfalfa variety is designated CW090075, a sample of said seed has been deposited as ATCC Accession Number PTA-122471.

Clause 18. The alfalfa variety of any one of clauses 1-13, wherein the alfalfa variety is designated CW054004, a sample of said seed has been deposited as ATCC Accession Number PTA-122470.

Clause 19. The alfalfa variety of any one of clauses 1-13, wherein the alfalfa variety is designated CW093009, a sample of said seed has been deposited as ATCC Accession Number PTA-122472.

Clause 20. The alfalfa variety of any one of clauses 1-13, wherein the alfalfa variety is designated CW104015, a sample of said seed has been deposited as ATCC Accession Number PTA-122476, Clause 21. A seed of the alfalfa variety of any one of clauses 1-20 or regenerable parts of said seed.

Clause 22. A plant, or a part thereof, produced by growing the seed of clause 21.

Clause 23. A pollen from the plant of clause 22.

Clause 24. An ovule from the plant of clause 22.

Clause 25. An alfalfa plant having all the physiological and morphological characteristics of the plant of clause 22.

Clause 26. A tissue culture of regenerable cells from the plant, or the part thereof, of clause 22.

Clause 27. The tissue culture of regenerable cells of clause 26, wherein the regenerable cells are selected from the group consisting of protoplasts and calli, and wherein the regenerable cells are from a leaf, pollen, ovule, cotyledon, hypocotyl, embryo, root, pod, flower, shoot or stalk.

Clause 28. A protoplast produced from the tissue culture of clause 26 or 27.

Clause 29. The tissue culture of clause 26 or 27, wherein the culture is a callus culture.

Clause 30. An alfalfa plant regenerated from the tissue culture of clause 26 or 27, wherein the alfalfa plant has all of the physiological and morphological characteristics of a plant produced by growing a seed designated CW096043 and deposited under ATCC Accession No. PTA-122473.

Clause 31. An alfalfa plant regenerated from the tissue culture of clause 26, wherein the alfalfa plant has all of the physiological and morphological characteristics of a plant produced by growing a seed designated CW103009 and deposited under ATCC Accession No. PTA-122475.

Clause 32. An alfalfa plant regenerated from the tissue culture of clause 26, wherein the alfalfa plant has all of the physiological and morphological characteristics of a plant produced by growing a seed designated CW099079 and deposited under ATCC Accession No. PTA-122474.

Clause 33. An alfalfa plant regenerated from the tissue culture of clause 26, wherein the alfalfa plant has all of the physiological and morphological characteristics of a plant produced by growing a seed designated CW090075 and deposited under ATCC Accession No. PTA-122471.

Clause 34. An alfalfa plant regenerated from the tissue culture of clause 26, wherein the alfalfa plant has all of the physiological and morphological characteristics of a plant produced by growing a seed designated CW054004 and deposited under ATCC Accession No. PTA-122470.

Clause 35. An alfalfa plant regenerated from the tissue culture of clause 26, wherein the alfalfa plant has all of the physiological and morphological characteristics of a plant produced by growing a seed designated CW093009 and deposited under ATCC Accession No. PTA-122472.

Clause 36. An alfalfa plant regenerated from the tissue culture of clause 26, wherein the alfalfa plant has all of the physiological and morphological characteristics of a plant produced by growing a seed designated CW104015 and deposited under ATCC Accession No. PTA-122476.

Clause 37. A tissue culture of regenerable cells from the plant, or the part thereof, of any one of clauses 30-36.

Clause 38. The tissue culture of clause 37, wherein said regenerable cells are selected from the group consisting of protoplasts and calli, and wherein the regenerable cells are from a leaf, pollen, ovule, cotyledon, hypocotyl, embryo, root, pod, flower, shoot or stalk.

Clause 39. A protoplast produced from the tissue culture of clause 37 or 38.

Clause 40. The tissue culture of clause 37 or 38, wherein the culture is a callus culture.

Clause 41. An alfalfa plant regenerated from the tissue culture of clause 37 or 38, wherein the plant has all of the physiological and morphological characteristics of a plant produced by growing a seed designated CW096043 and deposited under ATCC Accession No. PTA-122473, a plant produced by growing a seed designated CW103009 and deposited under ATCC Accession No. PTA-122475, a plant produced by growing a seed designated CW099079 and deposited under ATCC Accession No. PTA-122474, a plant produced by growing a seed designated CW090075 and deposited under ATCC Accession No. PTA-122471, a plant produced by growing a seed designated CW054004 and deposited under ATCC Accession No. PTA-122470, a plant produced by growing a seed designated CW093009 and deposited under ATCC Accession No. PTA-122472, or a plant produced by growing a seed designated CW104015 and deposited under ATCC Accession No. PTA-122476.

Clause 42. A *Medicago sativa* seed designated as CW096043, wherein a sample of said seed has been deposited as ATCC Accession Number PTA-122473.

Clause 43. A *Medicago sativa* seed designated as CW103009, wherein a sample of said seed has been deposited as ATCC Accession Number PTA-122475.

Clause 44. A *Medicago sativa* seed designated as CW099079, wherein a sample of said seed has been deposited as ATCC Accession Number PTA-122474.

Clause 45. A *Medicago sativa* seed designated as CW090075, wherein a sample of said seed has been deposited as ATCC Accession Number PTA-122471.

Clause 46. A *Medicago sativa* seed designated as CW054004, wherein a sample of said seed has been deposited as ATCC Accession Number PTA-122470.

Clause 47. A *Medicago sativa* seed designated as CW093009, wherein a sample of said seed has been deposited as ATCC Accession Number PTA-122472.

Clause 48. A *Medicago sativa* seed designated as CW104015, wherein a sample of said seed has been deposited as ATCC Accession Number PTA-122476.

Clause 49. A plant, or a part thereof, produced by growing the seed of any one of clauses 42-48.

Clause 50. A pollen from the plant of clause 49.

Clause 51. An ovule from the plant of clause 50.

Clause 52. An alfalfa plant having all the physiological and morphological characteristics of the plant of clause 49.

Clause 53. A tissue culture of regenerable cells from the plant, or the part thereof, of clause 49.

Clause 54. The tissue culture of regenerable cells of clause 53, wherein the regenerable cells are selected from the group consisting of protoplasts and calli, and wherein the regenerable cells are from a leaf, pollen, ovule, cotyledon, hypocotyl, embryo, root, pod, flower, shoot or stalk.

Clause 55. A protoplast produced from the tissue culture of clause 53 or 54.

Clause 56. The tissue culture of clause 53 or 54, wherein the culture is a callus culture.

Clause 57. An alfalfa plant regenerated from the tissue culture of clause 53 or 54, wherein the alfalfa plant has all of the physiological and morphological characteristics of a plant produced by growing a seed designated CW096043 and deposited under ATCC Accession No. PTA-122473, a plant produced by growing a seed designated CW103009 and deposited under ATCC Accession No. PTA-122475, a plant produced by growing a seed designated CW099079 and deposited under ATCC Accession No. PTA-122474, a plant produced by growing a seed designated CW090075 and deposited under ATCC Accession No. PTA-122471, a plant produced by growing a seed designated CW054004 and deposited under ATCC Accession No. PTA-122470, a plant produced by growing a seed designated CW093009 and deposited under ATCC Accession No. PTA-122472, or a plant produced by growing a seed designated CW104015 and deposited under ATCC Accession No. PTA-122476.

Clause 58. A tissue culture of regenerable cells from the plant, or the part thereof, of clause 57.

Clause 59. The tissue culture of clause 58, wherein said regenerable cells are selected from the group consisting of protoplasts and calli, and wherein the regenerable cells are from a leaf, pollen, ovule, cotyledon, hypocotyl, embryo, root, pod, flower, shoot or stalk.

Clause 60. A protoplast produced from the tissue culture of clause 58 or 59.

Clause 61. The tissue culture of clause 58 or 59, wherein the culture is a callus culture.

Clause 62. An alfalfa plant regenerated from the tissue culture of clause 58 or 59, wherein the alfalfa plant has all of the physiological and morphological characteristics of a plant produced by growing a seed designated CW096043 and deposited under ATCC Accession No. PTA-122473, a plant produced by growing a seed designated CW103009 and deposited under ATCC Accession No. PTA-122475, a plant produced by growing a seed designated CW099079 and deposited under ATCC Accession No. PTA-122474, a plant produced by growing a seed designated CW090075 and deposited under ATCC Accession No. PTA-122471, a plant produced by growing a seed designated CW054004 and deposited under ATCC Accession No. PTA-122470, a plant produced by growing a seed designated CW093009 and deposited under ATCC Accession No. PTA-122472, or a plant produced by growing a seed designated CW104015 and deposited under ATCC Accession No. PTA-122476.

Clause 63. A method for producing an alfalfa cultivar CW096043-derived alfalfa plant, the method comprising: (a) crossing CW096043 plants grown from CW096043 seed, representative seed of which has been deposited under ATCC Accession No: PTA-122473, with a second alfalfa plant to yield progeny alfalfa seed; and (b) growing the progeny seed to yield an alfalfa cultivar CW096043-derived alfalfa plant.

Clause 64. The method of clause 63, further comprising: (c) crossing the alfalfa cultivar CW096043-derived alfalfa plant of (b) with itself or a third alfalfa plant to yield a second alfalfa CW096043-derived alfalfa progeny seed; and (d) growing the second alfalfa progeny seed of (c) to yield a second alfalfa cultivar CW096043-derived alfalfa plant.

Clause 65. The method of clause 64, wherein (c) and (d) are repeated at least one time to generate an additional alfalfa cultivar CW096043-derived alfalfa plant.

Clause 66. A method for producing an alfalfa cultivar CW103009-derived alfalfa plant, the method comprising: (a) crossing CW103009 plants grown from CW103009 seed, representative seed of which has been deposited under ATCC Accession No: PTA-122475, with a second alfalfa plant to yield progeny alfalfa seed; and (b) growing the progeny seed to yield an alfalfa cultivar CW103009-derived alfalfa plant.

Clause 67. The method of clause 66, further comprising: (c) crossing the alfalfa cultivar CW103009-derived alfalfa plant of (b) with itself or a third alfalfa plant to yield a second alfalfa CW103009-derived alfalfa progeny seed; and (d) growing the second alfalfa progeny seed of (c) to yield a second alfalfa cultivar CW103009-derived alfalfa plant.

Clause 68. The method of clause 67, wherein (c) and (d) are repeated at least one time to generate an additional alfalfa cultivar CW103009-derived alfalfa plant.

Clause 69. A method for producing an alfalfa cultivar CW099079-derived alfalfa plant, the method comprising: (a) crossing CW099079 plants grown from CW099079 seed, representative seed of which has been deposited under ATCC Accession No: PTA-122474, with a second alfalfa plant to yield progeny alfalfa seed; and (b) growing the progeny seed to yield an alfalfa cultivar CW099079-derived alfalfa plant.

Clause 70. The method of clause 69, further comprising: (c) crossing the alfalfa cultivar CW099079-derived alfalfa plant of (b) with itself or a third alfalfa plant to yield a second alfalfa CW099079-derived alfalfa progeny seed; and (d) growing the second alfalfa progeny seed of (c) to yield a second alfalfa cultivar CW099079-derived alfalfa plant.

Clause 71. The method of clause 70, wherein (c) and (d) are repeated at least one time to generate an additional alfalfa cultivar CW099079-derived alfalfa plant.

Clause 72. A method for producing an alfalfa cultivar CW090075-derived alfalfa plant, the method comprising: (a) crossing CW090075 plants grown from CW090075 seed, representative seed of which has been deposited under ATCC Accession No: PTA-122471, with a second alfalfa plant to yield progeny alfalfa seed; and (b) growing the progeny seed to yield an alfalfa cultivar CW090075-derived alfalfa plant.

Clause 73. The method of clause 72, further comprising: (c) crossing the alfalfa cultivar CW090075-derived alfalfa plant of (b) with itself or a third alfalfa plant to yield a second alfalfa CW090075-derived alfalfa progeny seed; and (d) growing the second alfalfa progeny seed of (c) to yield a second alfalfa cultivar CW090075-derived alfalfa plant.

Clause 74. The method of clause 73, wherein (c) and (d) are repeated at least one time to generate an additional alfalfa cultivar CW090075-derived alfalfa plant.

Clause 75. A method for producing an alfalfa cultivar CW054004-derived alfalfa plant, the method comprising: (a) crossing CW054004 plants grown from CW054004 seed, representative seed of which has been deposited under ATCC Accession No: PTA-122470, with a second alfalfa plant to yield progeny alfalfa seed; and (b) growing the progeny seed to yield an alfalfa cultivar CW054004-derived alfalfa plant.

Clause 76. The method of clause 75, further comprising: (c) crossing the alfalfa cultivar CW054004-derived alfalfa plant of (b) with itself or a third alfalfa plant to yield a second alfalfa CW054004-derived alfalfa progeny seed; and (d) growing the second alfalfa progeny seed of (c) to yield a second alfalfa cultivar CW054004-derived alfalfa plant.

Clause 77. The method of clause 76, wherein (c) and (d) are repeated at least one time to generate an additional alfalfa cultivar CW054004-derived alfalfa plant.

Clause 78. A method for producing an alfalfa cultivar CW093009-derived alfalfa plant, the method comprising: (a) crossing CW093009 plants grown from CW093009 seed, representative seed of which has been deposited under ATCC Accession No: PTA-122472, with a second alfalfa plant to yield progeny alfalfa seed; and (b) growing the progeny seed to yield an alfalfa cultivar CW093009-derived alfalfa plant.

Clause 79. The method of clause 78, further comprising: (c) crossing the alfalfa cultivar CW093009-derived alfalfa plant of (b) with itself or a third alfalfa plant to yield a second alfalfa CW093009-derived alfalfa progeny seed; and (d) growing the second alfalfa progeny seed of (c) to yield a second alfalfa cultivar CW093009-derived alfalfa plant.

Clause 80. The method of clause 79, wherein (c) and (d) are repeated at least one time to generate an additional alfalfa cultivar CW093009-derived alfalfa plant.

Clause 81. A method for producing an alfalfa cultivar CW104015-derived alfalfa plant, the method comprising: (a) crossing CW104015 plants grown from CW104015 seed, representative seed of which has been deposited under ATCC Accession No: PTA-122476, with a second alfalfa plant to yield progeny alfalfa seed; and (b) growing the progeny seed to yield an alfalfa cultivar CW104015-derived alfalfa plant.

Clause 82. The method of clause 81, further comprising: (c) crossing the alfalfa cultivar CW104015-derived alfalfa plant of (b) with itself or a third alfalfa plant to yield a second alfalfa CW104015-derived alfalfa progeny seed; and (d) growing the second alfalfa progeny seed of (c) to yield a second alfalfa cultivar CW104015-derived alfalfa plant.

Clause 83. The method of clause 82, wherein (c) and (d) are repeated at least one time to generate an additional alfalfa cultivar CW104015-derived alfalfa plant.

Clause 84. A method of introducing a desired trait into alfalfa CW096043, CW103009, CW099079, CW090075, CW054004, CW093009, or CW104015, the method comprising:
(a) crossing CW096043, CW103009, CW099079, CW090075, CW054004, CW093009, or CW104015 plants grown from CW096043 seed, representative seed of which has been deposited under ATCC Accession No: PTA-122473, CW103009 seed, representative seed of which has been deposited under ATCC Accession No: PTA-122475, CW099079 seed, representative seed of which has been deposited under ATCC Accession No: PTA-122474, CW099079 seed, representative seed of which has been deposited under ATCC Accession No: PTA-122471, CW054004 seed, representative seed of which has been deposited under ATCC Accession No: PTA-122470, CW093009 seed, representative seed of which has been deposited under ATCC Accession No: PTA-122472, or CW104015 seed, representative seed of which has been deposited under ATCC Accession No: PTA-122476, with plants of a second alfalfa variety that comprise a desired trait to produce F1 progeny plants, wherein the desired trait is selected from the group consisting of male sterility, site-specific recombination, increased transformability, abiotic stress tolerance, herbicide resistance, insect resistance, disease resistance, altered phosphorus, altered antioxidants, altered fatty acids, altered essential amino acids and altered carbohydrates;

(b) selecting F1 progeny plants that have the desired trait to produce selected F1 progeny plants;

(c) crossing the selected progeny plants with the CW096043, CW103009, CW099079, CW090075, CW054004, CW093009, or CW104015 plants to produce backcross progeny plants;

(d) selecting for backcross progeny plants that have the desired trait and physiological and morphological characteristics of alfalfa variety CW096043, CW103009, CW099079, CW090075, CW054004, CW093009, or CW104015 to produce selected backcross progeny plants; and (e) repeating steps (c) and (d) three or more times in succession to produce selected fourth or higher backcross progeny plants that comprise the desired trait and all the physiological and morphological characteristics of alfalfa variety CW096043, CW103009, CW099079, CW090075, CW054004, CW093009, or CW104015.

Clause 85. A plant produced by the method of clause 84, wherein the plant has the desired trait and all of the physiological and all morphological characteristics of alfalfa variety CW096043, CW103009, CW099079, CW090075, CW054004, CW093009, or CW104015.

Clause 86. A method for producing an alfalfa plant having an altered agronomic trait, the method comprising introducing a polynucleotide into a CW096043 plant grown from CW096043 seed, representative seed of which has been deposited under ATCC Accession No: PTA-122473, a CW103009 plant grown from CW103009 seed, representative seed of which has been deposited under ATCC Accession No: PTA-122475, a CW099079 plant grown from CW099079 seed, representative seed of which has been deposited under ATCC Accession No: PTA-122474, a CW090075 plant grown from CW090075 seed, representative seed of which has been deposited under ATCC Accession No: PTA-122471, a CW054004 plant grown from CW054004 seed, representative seed of which has been deposited under ATCC Accession No: PTA-122470, a CW093009 plant grown from CW093009 seed, representative seed of which has been deposited under ATCC Accession No: PTA-122472, or a CW104015 plant grown from CW104015 seed, representative seed of which has been deposited under ATCC Accession No: PTA-122476, wherein the polynucleotide confers an altered agronomic trait to the plant selected from the group consisting of insect resistance, disease resistance, herbicide resistance, abiotic stress resistance, fatty acid metabolism, starch metabolism, carbohydrate metabolism, amino acid metabolism, phosphorus metabolism, antioxidant metabolism, male sterility, site specific DNA integration, plant growth, forage yield and flowering, and wherein the polynucleotide is expressed in the plant.

Clause 87. An alfalfa plant produced by the method of clause 86.

Clause 88. A composition comprising a mixture of alfalfa seed, the mixture of alfalfa seed comprises between about 75% to about 95% of CW096043 seed, representative seed of CW096043 has been deposited under ATCC Accession No: PTA-122473, between about 75% to about 95% of CW103009 seed, representative seed of CW103009 has been deposited under ATCC Accession No: PTA-122475, between about 75% to about 95% of CW099079 seed, representative seed of CW099079 has been deposited under ATCC Accession No: PTA-122474, between about 75% to about 95% of CW090075 seed, representative seed of CW090075 has been deposited under ATCC Accession No: PTA-122471, between about 75% to about 95% of CW054004 seed, representative seed of CW054004 has been deposited under ATCC Accession No: PTA-122470, between about 75% to about 95% of CW093009 seed, representative seed of CW093009 has been deposited under ATCC Accession No: PTA-122472, or between about 75% to about 95% of CW104015 seed, representative seed of CW104015 has been deposited under ATCC Accession No: PTA-122476.

Clause 89. A method for producing an alfalfa-derived alfalfa plant of the alfalfa variety of claim 1, the method comprising: (a) crossing a plant grown from the seed of the alfalfa variety of claim 1 with a second alfalfa plant to yield progeny alfalfa seed; and (b) growing the progeny seed to yield an alfalfa-derived alfalfa plant of the alfalfa variety of claim 1.

Clause 90. The method of claim 89, further comprising: (c) crossing the alfalfa-derived alfalfa plant of the alfalfa variety of claim 1 of (b) with itself or a third alfalfa plant to yield a second alfalfa-derived alfalfa progeny seed; and (d) growing the second alfalfa-derived alfalfa progeny seed of (c) to yield a second alfalfa-derived alfalfa plant of the alfalfa variety of claim 1.

Clause 91. The method of claim 90, wherein (c) and (d) are repeated at least one time to generate an additional alfalfa-derived alfalfa plant of the alfalfa variety of claim 1.

Clause 92. The method of claim 89, wherein the alfalfa-derived alfalfa plant is:

i) an alfalfa cultivar CW096043-derived alfalfa plant and the alfalfa variety of claim 1 is designated CW096043, a sample of said seed has been deposited as ATCC Accession Number PTA-122473, ii) an alfalfa cultivar CW096043-derived alfalfa plant and the alfalfa variety of claim 1 is designated CW096043, a sample of said seed has been deposited as ATCC Accession Number PTA-122473, iii) an alfalfa cultivar CW103009-derived alfalfa plant and the alfalfa variety is designated CW103009, a sample of said seed has been deposited as ATCC Accession Number PTA-122475, iv) an alfalfa cultivar CW099079-derived alfalfa plant and the alfalfa variety is designated CW099079, a sample of said seed has been deposited as ATCC Accession Number PTA-122474, v) an alfalfa cultivar CW090075-derived alfalfa plant and the alfalfa variety is designated CW090075, a sample of said seed has been deposited as ATCC Accession Number PTA-122471, vi) an alfalfa cultivar CW054004-derived alfalfa plant and the alfalfa variety is designated CW054004, a sample of said seed has been deposited as ATCC Accession Number PTA-122470, vii) an alfalfa cultivar CW093009-derived alfalfa plant and the alfalfa variety is designated CW093009, a sample of said seed has been deposited as ATCC Accession Number PTA-122472, or viii) an alfalfa cultivar CW104015-derived alfalfa plant and the alfalfa variety is designated CW104015, a sample of said seed has been deposited as ATCC Accession Number PTA-122476.

What is claimed is:

1. A *Medicago sativa* seed designated as CW 099079, wherein a sample of said seed has been deposited as ATCC Accession Number PTA-122474.

2. A plant, or a part thereof, produced by growing the seed of claim 1.

3. A pollen from the plant of claim 2.

4. An ovule from the plant of claim 2.

5. An alfalfa plant having all the physiological and morphological characteristics of the plant of claim 2.

6. A tissue culture of regenerable cells from the plant, or the part thereof, of claim 2.

7. The tissue culture of regenerable cells of claim 6, wherein the regenerable cells are selected from the group consisting of protoplasts and calli, and wherein the regenerable cells are from a leaf, pollen, ovule, cotyledon, hypocotyl, embryo, root, pod, flower, shoot or stalk.

8. A protoplast produced from the tissue culture of claim 7.

9. An alfalfa plant regenerated from the tissue culture of claim 7, wherein the plant has all of the physiological and morphological characteristics of a plant produced by growing a seed designated CW 099079 and deposited under ATCC Accession No. PTA-122474.

10. A tissue culture of regenerable cells from the plant, or the part thereof, of claim 6.

11. The tissue culture of claim 10, wherein said regenerable cells are selected from the group consisting of protoplasts and calli, and wherein the regenerable cells are from a leaf, pollen, ovule, cotyledon, hypocotyl, embryo, root, pod, flower, shoot or stalk.

12. A protoplast produced from the tissue culture of claim 10.

13. An alfalfa plant regenerated from the tissue culture of claim 10, wherein the plant has all of the physiological and morphological characteristics of a plant produced by growing a seed designated CW 099079 and deposited under ATCC Accession No. PTA-122474.

14. A method for producing an alfalfa cultivar CW 099079-derived alfalfa plant, comprising: (a) crossing CW 099079 plants grown from the seed of claim 1 with a second alfalfa plant to yield progeny alfalfa seed; and (b) growing the progeny seed to yield an alfalfa cultivar CW 099079-derived alfalfa plant.

15. The method of claim 14, further comprising: (c) crossing the alfalfa cultivar CW 099079-derived alfalfa plant of (b) with itself or a third alfalfa plant to yield a second alfalfa CW 099079-derived alfalfa progeny seed; and (d) growing the second alfalfa progeny seed of (c) to yield a second alfalfa cultivar CW 099079-derived alfalfa plant.

16. The method of claim 15, wherein (c) and (d) are repeated at least one time to generate an additional alfalfa cultivar CW 099079-derived alfalfa plant.

17. A method of introducing a desired trait into alfalfa CW 099079 comprising: (a) crossing CW 099079 plants grown from CW 099079 seed, representative seed of which has been deposited under ATCC Accession No: PTA-122474, with plants of a second alfalfa variety that comprise a desired trait to produce F1 progeny plants, wherein the desired trait is selected from the group consisting of male sterility, site-specific recombination, increased transformability, abiotic stress tolerance, herbicide resistance, insect resistance, disease resistance, altered phosphorus, altered antioxidants, altered fatty acids, altered essential amino acids and altered carbohydrates; (b) selecting F1 progeny plants that have the desired trait to produce selected F1 progeny plants; (c) crossing the selected progeny plants with the CW 099079 plants to produce backcross progeny plants; (d) selecting for backcross progeny plants that have the desired trait and physiological and morphological characteristics of alfalfa variety CW 099079 to produce selected backcross progeny plants; and (e) repeating steps (c) and (d) three or more times in succession to produce selected fourth or higher backcross progeny plants that comprise the desired trait and all the physiological and morphological characteristics of alfalfa variety CW 099079.

18. A plant produced by the method of claim 17, wherein the plant has the desired trait and otherwise all of the physiological and all morphological characteristics of said alfalfa variety CW 099079.

19. A method for producing an alfalfa plant having an altered agronomic trait comprising introducing a polynucleotide into the seed of claim 1, wherein the polynucleotide confers an altered agronomic trait to the plant selected from the group consisting of insect resistance, disease resistance, herbicide resistance, abiotic stress resistance, fatty acid metabolism, starch metabolism, carbohydrate metabolism, amino acid metabolism, phosphorus metabolism, antioxidant metabolism, male sterility, site specific DNA integration, plant growth, forage yield and flowering, and wherein the polynucleotide is expressed in the plant.

20. Seed of an alfalfa variety CW 099079, representative seed of alfalfa variety CW 099079 having been deposited under ATCC Accession Number PTA-122474, wherein the seed further comprises an altered agronomic trait, and wherein the seed produces a plant expressing the altered agronomic trait and otherwise having all of the physiological and all morphological characteristics as CW 099079 when grown under the same environmental conditions.

* * * * *